US012472111B2

(12) United States Patent
Bianchi et al.

(10) Patent No.: US 12,472,111 B2
(45) **Date of Patent: *Nov. 18, 2025**

(54) ABSORBENT CORE WITH PROFILED DISTRIBUTION OF ABSORBENT MATERIAL

(71) Applicant: The Procter & Gamble Company, Cincinnati, OH (US)

(72) Inventors: Ernesto Gabriel Bianchi, Oberursel (DE); Bruno Johannes Ehrnsperger, Bad Soden (DE); Joerg Endres, Frankfurt am Main (DE); Julien René Garcia, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 1100 days.

This patent is subject to a terminal disclaimer.

(21) Appl. No.: 17/072,406

(22) Filed: Oct. 16, 2020

(65) Prior Publication Data

US 2021/0030603 A1 Feb. 4, 2021

Related U.S. Application Data

(63) Continuation of application No. 15/499,948, filed on Apr. 28, 2017, now Pat. No. 10,842,690.

(30) Foreign Application Priority Data

Apr. 29, 2016 (EP) .................................... 16167637

(51) Int. Cl.
*A61F 13/537* (2006.01)
*A61F 13/15* (2006.01)
(Continued)

(52) U.S. Cl.
CPC ........ *A61F 13/5376* (2013.01); *A61F 13/532* (2013.01); *A61F 2013/15487* (2013.01);
(Continued)

(58) Field of Classification Search
CPC .................. A61F 13/536; A61F 13/532; A61F 2013/15487; A61F 2013/530051;
(Continued)

(56) References Cited

U.S. PATENT DOCUMENTS 1,733,997 A 10/1929 Marr
1,734,499 A 11/1929 Marinsky
(Continued)

FOREIGN PATENT DOCUMENTS

CA 2001370 4/1990
CA 2291997 6/2000
(Continued)

OTHER PUBLICATIONS

All Office Actions, U.S. Appl. No. 15/499,948.
(Continued)

*Primary Examiner* — Travis M Figg
(74) *Attorney, Agent, or Firm* — Daniel S. Albrecht

(57) ABSTRACT

An absorbent core for absorbent articles such as diapers comprising a core wrap comprising a top side and a bottom side, an absorbent material between the top side and the bottom side of the core wrap, a first and second longitudinally-extending channel-forming areas disposed on opposite sides of the longitudinal axis and substantially free of absorbent material preferably through which the top side of the core wrap is preferably attached to the bottom side of the core wrap. The core has a central absorbent zone between the first and the second channel-forming areas and a first and second lateral absorbent zones disposed laterally outwardly. The basis weight of the absorbent material in the central absorbent zone is higher than the basis weight of the absorbent material in each of the lateral absorbent zones for at least a first transversal section (S1). This relation is inverted along a second transversal section (S2) of the core.
(Continued)

The first and second sections have each a length in the longitudinal direction of at least 10 mm.

14 Claims, 10 Drawing Sheets

(51) Int. Cl.
*A61F 13/53* (2006.01)
*A61F 13/532* (2006.01)

(52) U.S. Cl.
CPC ............ *A61F 2013/530051* (2013.01); *A61F 2013/530124* (2013.01); *A61F 2013/530189* (2013.01); *A61F 2013/530233* (2013.01); *A61F 2013/530481* (2013.01); *A61F 2013/530715* (2013.01)

(58) Field of Classification Search
CPC ........ A61F 2013/530124; A61F 2013/530189; A61F 2013/530233; A61F 2013/530481; A61F 2013/530715
See application file for complete search history.

(56) References Cited

U.S. PATENT DOCUMENTS

| | | | |
|---|---|---|---|
| 1,989,283 | A | 1/1935 | Limacher |
| 2,058,509 | A | 10/1936 | Rose |
| 2,271,676 | A | 2/1942 | Bjornbak |
| 2,450,789 | A | 10/1948 | Frieman |
| 2,508,811 | A | 5/1950 | Best et al. |
| 2,568,910 | A | 9/1951 | Condylis |
| 2,570,796 | A | 10/1951 | Gross |
| 2,570,963 | A | 10/1951 | Mesmer |
| 2,583,553 | A | 1/1952 | Faure |
| 2,705,957 | A | 4/1955 | Mauro |
| 2,788,003 | A | 4/1957 | Morin |
| 2,788,786 | A | 4/1957 | Dexter |
| 2,798,489 | A | 7/1957 | Behrman |
| 2,807,263 | A | 9/1957 | Newton |
| 2,830,589 | A | 4/1958 | Doner |
| 2,890,700 | A | 6/1959 | Lönberg-Holm |
| 2,890,701 | A | 6/1959 | Weinman |
| 2,898,912 | A | 8/1959 | Adams |
| 2,931,361 | A | 4/1960 | Sostsrin |
| 2,977,957 | A | 4/1961 | Clyne |
| 3,071,138 | A | 1/1963 | Gustavo |
| 3,180,335 | A | 4/1965 | Duncan et al. |
| 3,207,158 | A | 9/1965 | Yoshitake et al. |
| 3,227,160 | A | 1/1966 | Joy |
| 3,386,442 | A | 6/1968 | Sabee |
| 3,561,446 | A | 2/1971 | Jones |
| 3,572,342 | A | 3/1971 | Lindquist et al. |
| 3,572,432 | A | 3/1971 | Burton |
| 3,575,174 | A | 4/1971 | Mogor |
| 3,578,155 | A | 5/1971 | Small et al. |
| 3,606,887 | A | 9/1971 | Roeder |
| 3,610,244 | A | 10/1971 | Jones |
| 3,618,608 | A | 11/1971 | Brink |
| 3,642,001 | A | 2/1972 | Sabee |
| 3,653,381 | A | 4/1972 | Warnken |
| 3,670,731 | A | 6/1972 | Harmon |
| 3,688,767 | A | 9/1972 | Goldstein |
| 3,710,797 | A | 1/1973 | Marsan |
| 3,731,688 | A | 5/1973 | Litt et al. |
| 3,756,878 | A | 9/1973 | Willot |
| 3,774,241 | A | 11/1973 | Zerkle |
| 3,776,233 | A | 12/1973 | Schaar |
| 3,814,100 | A | 6/1974 | Nystrand et al. |
| 3,828,784 | A | 8/1974 | Zoephel |
| 3,840,418 | A | 10/1974 | Sabee |
| 3,847,702 | A | 11/1974 | Jones |
| 3,848,594 | A | 11/1974 | Buell |
| 3,848,595 | A | 11/1974 | Endres |
| 3,848,597 | A | 11/1974 | Endres |
| 3,860,003 | A | 1/1975 | Buell |
| 3,863,637 | A | 2/1975 | MacDonald et al. |
| 3,882,870 | A | 5/1975 | Hathaway |
| 3,884,234 | A | 5/1975 | Taylor |
| 3,900,032 | A | 8/1975 | Heurlen |
| 3,911,173 | A | 10/1975 | Sprague, Jr. |
| 3,920,017 | A | 11/1975 | Karami |
| 3,924,626 | A | 12/1975 | Lee et al. |
| 3,926,189 | A | 12/1975 | Taylor |
| 3,929,134 | A | 12/1975 | Karami |
| 3,929,135 | A | 12/1975 | Thompson |
| 3,930,501 | A | 1/1976 | Schaar |
| 3,938,523 | A | 2/1976 | Gilliland et al. |
| 3,968,799 | A | 7/1976 | Schrading |
| 3,978,861 | A | 9/1976 | Schaar |
| 3,981,306 | A | 9/1976 | Krusko |
| 3,987,794 | A | 10/1976 | Schaar |
| 3,995,637 | A | 12/1976 | Schaar |
| 3,995,640 | A | 12/1976 | Schaar |
| 3,999,547 | A | 12/1976 | Hernandez |
| 4,014,338 | A | 3/1977 | Schaar |
| 4,034,760 | A | 7/1977 | Amirsakis |
| 4,055,180 | A | 10/1977 | Karami |
| 4,074,508 | A | 2/1978 | Reid |
| 4,079,739 | A | 3/1978 | Whitehead |
| 4,084,592 | A | 4/1978 | Tritsch |
| 4,100,922 | A | 7/1978 | Hernandez |
| 4,232,674 | A | 11/1980 | Melican |
| 4,257,418 | A | 3/1981 | Hessner |
| 4,259,220 | A | 3/1981 | Bunnelle et al. |
| 4,296,750 | A | 10/1981 | Woon et al. |
| 4,315,508 | A | 2/1982 | Bolick |
| 4,324,246 | A | 4/1982 | Mullane et al. |
| 4,340,706 | A | 7/1982 | Obayashi et al. |
| 4,341,216 | A | 7/1982 | Obenour |
| 4,342,314 | A | 8/1982 | Radel et al. |
| 4,360,021 | A | 11/1982 | Stima |
| 4,381,783 | A | 5/1983 | Elias |
| 4,388,075 | A | 6/1983 | Mesek et al. |
| 4,410,571 | A | 10/1983 | Korpman |
| 4,461,621 | A | 7/1984 | Karami et al. |
| 4,463,045 | A | 7/1984 | Ahr et al. |
| 4,469,710 | A | 9/1984 | Rielley et al. |
| 4,475,912 | A | 10/1984 | Coates |
| 4,490,148 | A | 12/1984 | Beckeström |
| 4,507,438 | A | 3/1985 | Obayashi et al. |
| 4,515,595 | A | 5/1985 | Kievet et al. |
| 4,527,990 | A | 7/1985 | Sigl |
| 4,541,871 | A | 9/1985 | Obayashi et al. |
| 4,551,191 | A | 11/1985 | Kock et al. |
| 4,573,986 | A | 3/1986 | Minetola et al. |
| 4,578,072 | A | 3/1986 | Lancaster |
| 4,578,702 | A | 3/1986 | Campbell |
| 4,585,448 | A | 4/1986 | Enloe |
| 4,585,450 | A | 4/1986 | Rosch et al. |
| 4,589,878 | A | 5/1986 | Mitrani |
| 4,596,568 | A | 6/1986 | Flug |
| 4,601,717 | A | 7/1986 | Blevins |
| 4,606,964 | A | 8/1986 | Wideman |
| 4,609,518 | A | 9/1986 | Curro et al. |
| 4,610,678 | A | 9/1986 | Weisman et al. |
| 4,623,342 | A | 11/1986 | Ito et al. |
| 4,624,666 | A | 11/1986 | Derossett |
| 4,629,643 | A | 12/1986 | Curro et al. |
| 4,636,207 | A | 1/1987 | Buell |
| 4,641,381 | A | 2/1987 | Heran et al. |
| 4,646,510 | A | 3/1987 | McIntyre |
| 4,662,875 | A | 5/1987 | Hirotsu et al. |
| 4,666,983 | A | 5/1987 | Tsubakimoto et al. |
| 4,670,011 | A | 6/1987 | Mesek |
| 4,670,012 | A | 6/1987 | Johnson |
| 4,680,030 | A | 7/1987 | Coates et al. |
| 4,681,579 | A | 7/1987 | Toussant et al. |
| 4,681,581 | A | 7/1987 | Coates |
| 4,681,793 | A | 7/1987 | Linman et al. |
| 4,685,915 | A | 8/1987 | Hasse |
| 4,690,680 | A | 9/1987 | Higgins |
| 4,695,278 | A | 9/1987 | Lawson |

(56) References Cited

U.S. PATENT DOCUMENTS

| | | | |
|---|---|---|---|
| 4,699,622 | A | 10/1987 | Toussant et al. |
| 4,704,115 | A | 11/1987 | Buell |
| 4,704,116 | A | 11/1987 | Enloe |
| 4,710,189 | A | 12/1987 | Lash |
| 4,720,321 | A | 1/1988 | Smith |
| 4,731,066 | A | 3/1988 | Korpman |
| 4,731,070 | A | 3/1988 | Koci |
| RE32,649 | E | 4/1988 | Brandt et al. |
| 4,741,941 | A | 5/1988 | Englebert et al. |
| 4,747,846 | A | 5/1988 | Boland et al. |
| 4,753,648 | A | 6/1988 | Jackson |
| 4,773,905 | A | 9/1988 | Molee |
| 4,784,892 | A | 11/1988 | Storey et al. |
| 4,785,996 | A | 11/1988 | Ziecker et al. |
| 4,787,896 | A | 11/1988 | Houghton et al. |
| 4,795,454 | A | 1/1989 | Dragoo |
| 4,800,102 | A | 1/1989 | Takada |
| 4,802,884 | A | 2/1989 | Fröidh et al. |
| 4,806,408 | A | 2/1989 | Pierre et al. |
| 4,806,598 | A | 2/1989 | Morman |
| 4,808,176 | A | 2/1989 | Kielpikowski |
| 4,808,178 | A | 2/1989 | Aziz |
| 4,826,880 | A | 5/1989 | Lesniak et al. |
| 4,834,735 | A | 5/1989 | Alemany et al. |
| 4,834,740 | A | 5/1989 | Suzuki et al. |
| 4,834,742 | A | 5/1989 | Wilson et al. |
| 4,838,886 | A | 6/1989 | Kent |
| 4,842,666 | A | 6/1989 | Werenicz |
| 4,846,815 | A | 7/1989 | Scripps |
| 4,846,825 | A | 7/1989 | Enloe et al. |
| 4,848,815 | A | 7/1989 | Molloy |
| 4,861,652 | A | 8/1989 | Lippert et al. |
| 4,869,724 | A | 9/1989 | Scripps |
| 4,886,697 | A | 12/1989 | Perdelwitz, Jr. et al. |
| 4,888,231 | A | 12/1989 | Angstadt |
| 4,892,528 | A | 1/1990 | Suzuki et al. |
| 4,892,535 | A | 1/1990 | Bjornberg |
| 4,892,536 | A | 1/1990 | DesMarais et al. |
| 4,894,060 | A | 1/1990 | Nestegard |
| 4,894,277 | A | 1/1990 | Akasaki |
| 4,900,317 | A | 2/1990 | Buell |
| 4,904,251 | A | 2/1990 | Igaue et al. |
| 4,909,802 | A | 3/1990 | Ahr et al. |
| 4,909,803 | A | 3/1990 | Aziz et al. |
| 4,936,839 | A | 6/1990 | Molee |
| 4,940,463 | A | 7/1990 | Leathers et al. |
| 4,940,464 | A | 7/1990 | Van Gompel et al. |
| 4,946,527 | A | 8/1990 | Battrell |
| 4,950,264 | A | 8/1990 | Osborn |
| 4,960,477 | A | 10/1990 | Mesek |
| 4,963,140 | A | 10/1990 | Robertson et al. |
| 4,966,809 | A | 10/1990 | Tanaka et al. |
| 4,968,313 | A | 11/1990 | Sabee |
| 4,990,147 | A | 2/1991 | Freeland |
| 4,994,053 | A | 2/1991 | Lang |
| 5,006,394 | A | 4/1991 | Baird |
| 5,019,063 | A | 5/1991 | Marsan et al. |
| 5,019,072 | A | 5/1991 | Polski |
| 5,021,051 | A | 6/1991 | Hiuke |
| 5,030,314 | A | 7/1991 | Lang |
| 5,032,120 | A | 7/1991 | Freeland et al. |
| 5,034,008 | A | 7/1991 | Breitkopf |
| 5,037,416 | A | 8/1991 | Allen et al. |
| 5,071,414 | A | 12/1991 | Elliott |
| 5,072,687 | A | 12/1991 | Mitchell |
| 5,085,654 | A | 2/1992 | Buell |
| 5,087,255 | A | 2/1992 | Sims et al. |
| 5,092,861 | A | 3/1992 | Nomura et al. |
| 5,102,597 | A | 4/1992 | Roe et al. |
| 5,114,420 | A | 5/1992 | Igaue et al. |
| 5,124,188 | A | 6/1992 | Roe et al. |
| 5,135,522 | A | 8/1992 | Fahrenkrug et al. |
| 5,137,537 | A | 8/1992 | Herron et al. |
| D329,697 | S | 9/1992 | Fahrenkrug et al. |
| 5,143,679 | A | 9/1992 | Weber et al. |
| 5,147,343 | A | 9/1992 | Kellenberger |
| 5,147,345 | A | 9/1992 | Young et al. |
| 5,149,334 | A | 9/1992 | Roe et al. |
| 5,149,335 | A | 9/1992 | Kellenberger et al. |
| 5,151,091 | A | 9/1992 | Glaug |
| 5,151,092 | A | 9/1992 | Buell et al. |
| 5,156,793 | A | 10/1992 | Buell et al. |
| 5,167,653 | A | 12/1992 | Igaue et al. |
| 5,167,897 | A | 12/1992 | Weber et al. |
| 5,175,046 | A | 12/1992 | Nguyen |
| 5,180,622 | A | 1/1993 | Berg et al. |
| 5,190,563 | A | 3/1993 | Herron et al. |
| 5,190,606 | A | 3/1993 | Merkatoris et al. |
| 5,204,997 | A | 4/1993 | Suzuki et al. |
| 5,213,817 | A | 5/1993 | Pelley |
| 5,221,274 | A | 6/1993 | Buell et al. |
| 5,235,515 | A | 8/1993 | Ungpiyakul et al. |
| 5,242,436 | A | 9/1993 | Weil et al. |
| 5,246,431 | A | 9/1993 | Minetola et al. |
| 5,246,432 | A | 9/1993 | Suzuki et al. |
| 5,246,433 | A | 9/1993 | Hasse et al. |
| 5,248,309 | A | 9/1993 | Serbiak et al. |
| 5,260,345 | A | 11/1993 | Desmarais et al. |
| 5,269,775 | A | 12/1993 | Freeland et al. |
| 5,281,683 | A | 1/1994 | Yano et al. |
| H1298 | H | 4/1994 | Ahr |
| 5,300,565 | A | 4/1994 | Berg et al. |
| 5,312,386 | A | 5/1994 | Correa et al. |
| 5,331,059 | A | 7/1994 | Engelhardt et al. |
| 5,336,552 | A | 8/1994 | Strack et al. |
| 5,348,547 | A | 9/1994 | Payne et al. |
| 5,358,500 | A | 10/1994 | LaVon et al. |
| 5,366,782 | A | 11/1994 | Curro et al. |
| 5,382,610 | A | 1/1995 | Harada et al. |
| 5,387,207 | A | 2/1995 | Dyer et al. |
| 5,387,208 | A | 2/1995 | Ashton et al. |
| 5,387,209 | A | 2/1995 | Yamamoto et al. |
| 5,389,095 | A | 2/1995 | Suzuki |
| 5,397,316 | A | 3/1995 | Lavon et al. |
| 5,397,317 | A | 3/1995 | Thomas |
| 5,399,175 | A | 3/1995 | Glaug |
| 5,401,792 | A | 3/1995 | Babu et al. |
| 5,409,771 | A | 4/1995 | Dahmen et al. |
| H1440 | H | 5/1995 | New et al. |
| 5,411,497 | A | 5/1995 | Tanzer et al. |
| 5,415,644 | A | 5/1995 | Enloe |
| 5,425,725 | A | 6/1995 | Tanzer et al. |
| 5,429,630 | A | 7/1995 | Beal et al. |
| 5,433,715 | A | 7/1995 | Tanzer et al. |
| 5,451,219 | A | 9/1995 | Suzuki |
| 5,451,442 | A | 9/1995 | Pieniak |
| 5,460,622 | A | 10/1995 | Dragoo et al. |
| 5,460,623 | A | 10/1995 | Emenaker et al. |
| 5,462,541 | A | 10/1995 | Bruemmer et al. |
| 5,476,458 | A | 12/1995 | Glaug et al. |
| 5,486,166 | A | 1/1996 | Bishop et al. |
| 5,486,167 | A | 1/1996 | Dragoo et al. |
| 5,490,846 | A | 2/1996 | Ellis et al. |
| 5,492,962 | A | 2/1996 | Lahrman et al. |
| 5,494,622 | A | 2/1996 | Heath et al. |
| 5,499,978 | A | 3/1996 | Buell et al. |
| 5,507,736 | A | 4/1996 | Clear et al. |
| 5,507,895 | A | 4/1996 | Suekane |
| 5,509,915 | A | 4/1996 | Hanson et al. |
| 5,514,104 | A | 5/1996 | Cole |
| 5,518,801 | A | 5/1996 | Chappell et al. |
| 5,520,674 | A | 5/1996 | Hines et al. |
| 5,522,810 | A | 6/1996 | Allen, Jr. |
| 5,527,300 | A | 6/1996 | Sauer |
| 5,531,730 | A | 7/1996 | Dreier |
| 5,532,323 | A | 7/1996 | Yano et al. |
| 5,542,943 | A | 8/1996 | Sageser |
| 5,549,592 | A | 8/1996 | Fries et al. |
| 5,549,593 | A | 8/1996 | Ygge et al. |
| 5,549,791 | A | 8/1996 | Herron et al. |
| 5,554,145 | A | 9/1996 | Roe et al. |
| 5,559,335 | A | 9/1996 | Zing et al. |
| 5,560,878 | A | 10/1996 | Dragoo et al. |
| 5,562,634 | A | 10/1996 | Flumene et al. |

(56) References Cited

U.S. PATENT DOCUMENTS

| | | | |
|---|---|---|---|
| 5,562,646 | A | 10/1996 | Goldman et al. |
| 5,569,234 | A | 10/1996 | Buell et al. |
| 5,571,096 | A | 11/1996 | Dobrin et al. |
| 5,574,121 | A | 11/1996 | Irie et al. |
| 5,575,783 | A | 11/1996 | Clear et al. |
| 5,580,411 | A | 12/1996 | Nease et al. |
| 5,584,829 | A | 12/1996 | Lavash et al. |
| 5,586,979 | A | 12/1996 | Thomas |
| 5,591,152 | A | 1/1997 | Buell et al. |
| 5,591,155 | A | 1/1997 | Nishikawa et al. |
| 5,593,399 | A | 1/1997 | Tanzer et al. |
| 5,599,335 | A | 2/1997 | Goldman et al. |
| 5,601,542 | A | 2/1997 | Melius et al. |
| 5,607,414 | A | 3/1997 | Richards et al. |
| 5,607,416 | A | 3/1997 | Yamamoto et al. |
| 5,607,537 | A | 3/1997 | Johnson et al. |
| 5,607,760 | A | 3/1997 | Roe et al. |
| 5,609,587 | A | 3/1997 | Roe |
| 5,609,588 | A | 3/1997 | DiPalma et al. |
| 5,611,879 | A | 3/1997 | Morman |
| 5,613,959 | A | 3/1997 | Roessler et al. |
| 5,613,960 | A | 3/1997 | Mizutani |
| 5,614,283 | A | 3/1997 | Potnis et al. |
| 5,622,589 | A | 4/1997 | Johnson et al. |
| 5,624,423 | A | 4/1997 | Anjur |
| 5,624,424 | A | 4/1997 | Saisaka et al. |
| 5,625,222 | A | 4/1997 | Yoneda et al. |
| 5,626,571 | A | 5/1997 | Young et al. |
| 5,628,741 | A | 5/1997 | Buell et al. |
| 5,628,845 | A | 5/1997 | Murray et al. |
| 5,635,191 | A | 6/1997 | Roe et al. |
| 5,635,271 | A | 6/1997 | Zafiroglu |
| 5,637,106 | A | 6/1997 | Mitchell |
| 5,643,238 | A | 7/1997 | Baker |
| 5,643,243 | A | 7/1997 | Klemp |
| 5,643,588 | A | 7/1997 | Roe et al. |
| 5,649,914 | A | 7/1997 | Glaug |
| 5,650,214 | A | 7/1997 | Anderson |
| H1674 | H | 8/1997 | Ames et al. |
| 5,658,268 | A | 8/1997 | Johns et al. |
| 5,662,634 | A | 9/1997 | Yamamoto et al. |
| 5,662,638 | A | 9/1997 | Johnson et al. |
| 5,662,758 | A | 9/1997 | Hamilton et al. |
| 5,669,894 | A | 9/1997 | Goldman et al. |
| 5,674,215 | A | 10/1997 | Ronnberg |
| 5,681,300 | A | 10/1997 | Ahr |
| 5,683,374 | A | 11/1997 | Yamamoto |
| 5,685,874 | A | 11/1997 | Buell et al. |
| 5,690,624 | A | 11/1997 | Sasaki et al. |
| 5,690,627 | A | 11/1997 | Clear et al. |
| 5,691,035 | A | 11/1997 | Chappell et al. |
| 5,691,036 | A | 11/1997 | Chappell et al. |
| 5,695,488 | A | 12/1997 | Sosalla |
| 5,700,254 | A | 12/1997 | McDowall et al. |
| 5,702,376 | A | 12/1997 | Glaug |
| 5,714,156 | A | 2/1998 | Schmidt et al. |
| 5,723,087 | A | 3/1998 | Chappell et al. |
| 5,733,275 | A | 3/1998 | Davis et al. |
| 5,749,866 | A | 5/1998 | Roe et al. |
| 5,752,947 | A | 5/1998 | Awolin |
| 5,756,039 | A | 5/1998 | Mcfall et al. |
| H1732 | H | 6/1998 | Johnson |
| 5,762,641 | A | 6/1998 | Bewick et al. |
| 5,766,388 | A | 6/1998 | Pelley |
| 5,766,389 | A | 6/1998 | Brandon et al. |
| 5,772,825 | A | 6/1998 | Schmitz |
| 5,776,121 | A | 7/1998 | Roe et al. |
| 5,779,831 | A | 7/1998 | Schmitz |
| 5,788,684 | A | 8/1998 | Abuto et al. |
| 5,795,345 | A | 8/1998 | Mizutani |
| 5,797,892 | A | 8/1998 | Glaug |
| 5,797,894 | A | 8/1998 | Cadieux et al. |
| 5,807,365 | A | 9/1998 | Luceri |
| 5,810,796 | A | 9/1998 | Kimura et al. |
| 5,810,800 | A | 9/1998 | Hunter et al. |
| 5,814,035 | A | 9/1998 | Gryskiewicz et al. |
| 5,820,618 | A | 10/1998 | Roberts et al. |
| 5,827,257 | A | 10/1998 | Fujioka |
| 5,830,202 | A | 11/1998 | Bogdanski et al. |
| 5,833,678 | A | 11/1998 | Ashton et al. |
| 5,837,789 | A | 11/1998 | Stockhausen et al. |
| 5,840,404 | A | 11/1998 | Graff |
| 5,843,059 | A | 12/1998 | Niemeyer et al. |
| 5,846,231 | A | 12/1998 | Fujioka et al. |
| 5,846,232 | A | 12/1998 | Serbiak et al. |
| 5,849,816 | A | 12/1998 | Suskind et al. |
| 5,851,204 | A | 12/1998 | Mitzutani |
| 5,855,572 | A | 1/1999 | Schmidt |
| 5,858,013 | A | 1/1999 | Kling |
| 5,858,515 | A | 1/1999 | Stokes et al. |
| 5,865,823 | A | 2/1999 | Curro |
| 5,865,824 | A | 2/1999 | Chen |
| 5,873,868 | A | 2/1999 | Nakahata |
| 5,876,391 | A | 3/1999 | Roe et al. |
| 5,879,751 | A | 3/1999 | Bogdanski |
| 5,891,118 | A | 4/1999 | Toyoshima |
| 5,891,544 | A | 4/1999 | Chappell et al. |
| 5,897,545 | A | 4/1999 | Kline et al. |
| 5,904,673 | A | 5/1999 | Roe et al. |
| 5,925,439 | A | 7/1999 | Haubach |
| 5,928,184 | A | 7/1999 | Etheredge |
| 5,931,825 | A | 8/1999 | Kuen et al. |
| 5,938,648 | A | 8/1999 | Lavon et al. |
| 5,938,650 | A | 8/1999 | Baer et al. |
| 5,941,862 | A | 8/1999 | Haynes et al. |
| 5,944,706 | A | 8/1999 | Palumbo et al. |
| 5,947,949 | A | 9/1999 | Inoue et al. |
| 5,951,536 | A | 9/1999 | Osborn, III et al. |
| 5,957,908 | A | 9/1999 | Kline et al. |
| 5,968,025 | A | 10/1999 | Roe et al. |
| 5,968,029 | A | 10/1999 | Chappell et al. |
| 5,980,500 | A | 11/1999 | Shimizu et al. |
| 5,981,824 | A | 11/1999 | Luceri |
| 5,989,236 | A | 11/1999 | Roe et al. |
| 6,004,306 | A | 12/1999 | Roe et al. |
| 6,010,490 | A | 1/2000 | Freeland et al. |
| 6,022,430 | A | 2/2000 | Blenke et al. |
| 6,022,431 | A | 2/2000 | Blenke et al. |
| 6,042,673 | A | 3/2000 | Johnson et al. |
| 6,050,984 | A | 4/2000 | Fujioka |
| 6,054,631 | A | 4/2000 | Gent |
| 6,056,732 | A | 5/2000 | Fujioka et al. |
| 6,060,115 | A | 5/2000 | Borowski et al. |
| 6,068,620 | A | 5/2000 | Chmielewski |
| 6,080,909 | A | 6/2000 | Osterdahl et al. |
| 6,083,210 | A | 7/2000 | Young et al. |
| 6,090,994 | A | 7/2000 | Chen |
| 6,091,336 | A | 7/2000 | Zand |
| 6,093,474 | A | 7/2000 | Sironi |
| 6,099,515 | A | 8/2000 | Sugito |
| 6,102,892 | A | 8/2000 | Putzer et al. |
| 6,103,814 | A | 8/2000 | Van Drongelen et al. |
| 6,107,537 | A | 8/2000 | Elder et al. |
| 6,110,157 | A | 8/2000 | Schmidt |
| 6,117,121 | A | 9/2000 | Faulks et al. |
| 6,117,803 | A | 9/2000 | Morman et al. |
| 6,120,486 | A | 9/2000 | Toyoda et al. |
| 6,120,487 | A | 9/2000 | Ashton |
| 6,120,489 | A | 9/2000 | Johnson et al. |
| 6,120,866 | A | 9/2000 | Arakawa et al. |
| 6,121,509 | A | 9/2000 | Ashraf et al. |
| 6,129,717 | A | 10/2000 | Fujioka et al. |
| 6,129,720 | A | 10/2000 | Blenke et al. |
| 6,132,411 | A | 10/2000 | Huber et al. |
| 6,139,912 | A | 10/2000 | Onuschak |
| 6,143,821 | A | 11/2000 | Houben |
| 6,152,908 | A | 11/2000 | Widlund |
| 6,156,023 | A | 12/2000 | Yoshioka |
| 6,156,424 | A | 12/2000 | Taylor |
| 6,160,197 | A | 12/2000 | Lassen |
| 6,165,160 | A | 12/2000 | Suzuki et al. |
| 6,174,302 | B1 | 1/2001 | Kumasaka |
| 6,177,606 | B1 | 1/2001 | Etheredge |
| 6,177,607 | B1 | 1/2001 | Blaney et al. |

(56) References Cited

U.S. PATENT DOCUMENTS

| | | | |
|---|---|---|---|
| 6,186,996 | B1 | 2/2001 | Martin |
| 6,210,386 | B1 | 4/2001 | Inoue |
| 6,210,390 | B1 | 4/2001 | Karlsson |
| 6,231,556 | B1 | 5/2001 | Osborn, III |
| 6,231,566 | B1 | 5/2001 | Lai |
| 6,238,380 | B1 | 5/2001 | Sasaki |
| 6,241,716 | B1 | 6/2001 | Rönnberg |
| 6,254,294 | B1 | 7/2001 | Muhar |
| 6,258,996 | B1 | 7/2001 | Goldman |
| 6,265,488 | B1 | 7/2001 | Fujino et al. |
| 6,290,686 | B1 | 9/2001 | Tanzer et al. |
| 6,306,122 | B1 | 10/2001 | Narawa et al. |
| 6,315,765 | B1 | 11/2001 | Datta |
| 6,319,239 | B1 | 11/2001 | Daniels et al. |
| 6,322,552 | B1 | 11/2001 | Blenke et al. |
| 6,325,787 | B1 | 12/2001 | Roe et al. |
| 6,326,525 | B1 | 12/2001 | Hamajima |
| 6,330,735 | B1 | 12/2001 | Hahn et al. |
| 6,334,858 | B1 | 1/2002 | Rönnberg et al. |
| 6,336,922 | B1 | 1/2002 | Van Gompel et al. |
| 6,340,611 | B1 | 1/2002 | Shimizu |
| 6,342,715 | B1 | 1/2002 | Shimizu |
| 6,350,332 | B1 | 2/2002 | Thomas et al. |
| 6,368,687 | B1 | 4/2002 | Joseph et al. |
| 6,371,948 | B1 | 4/2002 | Mizutani |
| 6,372,952 | B1 | 4/2002 | Lash et al. |
| 6,375,644 | B2 | 4/2002 | Mizutani |
| 6,376,034 | B1 | 4/2002 | Brander |
| 6,383,431 | B1 | 5/2002 | Dobrin et al. |
| 6,383,960 | B1 | 5/2002 | Everett et al. |
| 6,394,989 | B2 | 5/2002 | Mizutani |
| 6,402,729 | B1 | 6/2002 | Boberg et al. |
| 6,402,731 | B1 | 6/2002 | Suprise et al. |
| 6,403,857 | B1 | 6/2002 | Gross et al. |
| 6,406,467 | B1 | 6/2002 | Dilnik et al. |
| 6,409,883 | B1 | 6/2002 | Makolin |
| 6,410,820 | B1 | 6/2002 | McFall et al. |
| 6,410,822 | B1 | 6/2002 | Mizutani |
| 6,413,248 | B1 | 7/2002 | Mizutani |
| 6,413,249 | B1 | 7/2002 | Turi et al. |
| 6,414,214 | B1 | 7/2002 | Engelhardt et al. |
| 6,416,502 | B1 | 7/2002 | Connelly et al. |
| 6,416,697 | B1 | 7/2002 | Venturino et al. |
| 6,419,667 | B1 | 7/2002 | Avalon et al. |
| 6,423,046 | B1 | 7/2002 | Fujioka et al. |
| 6,423,048 | B1 | 7/2002 | Suzuki et al. |
| 6,423,884 | B1 | 7/2002 | Oehmen |
| 6,429,350 | B1 | 8/2002 | Tanzer et al. |
| 6,432,094 | B1 | 8/2002 | Fujioka et al. |
| 6,432,098 | B1 | 8/2002 | Kline et al. |
| 6,432,099 | B2 | 8/2002 | Rönnberg |
| 6,437,214 | B1 | 8/2002 | Everett et al. |
| 6,441,268 | B1 | 8/2002 | Edwardsson |
| 6,443,933 | B1 | 9/2002 | Suzuki et al. |
| 6,444,064 | B1 | 9/2002 | Henry et al. |
| 6,447,496 | B1 | 9/2002 | Mizutani |
| 6,458,111 | B1 | 10/2002 | Onishi et al. |
| 6,458,877 | B1 | 10/2002 | Ahmed et al. |
| 6,459,016 | B1 | 10/2002 | Rosenfeld et al. |
| 6,461,034 | B1 | 10/2002 | Schaefer et al. |
| 6,461,342 | B2 | 10/2002 | Tanji et al. |
| 6,461,343 | B1 | 10/2002 | Schaefer et al. |
| 6,472,478 | B1 | 10/2002 | Funk et al. |
| 6,475,201 | B2 | 11/2002 | Saito et al. |
| 6,494,872 | B1 | 12/2002 | Suzuki et al. |
| 6,494,873 | B2 | 12/2002 | Karlsson et al. |
| 6,500,159 | B1 | 12/2002 | Carvalho |
| 6,503,233 | B1 | 1/2003 | Chen |
| 6,503,979 | B1 | 1/2003 | Funk et al. |
| 6,506,186 | B1 | 1/2003 | Roessler |
| 6,506,961 | B1 | 1/2003 | Levy |
| 6,515,195 | B1 | 2/2003 | Lariviere |
| 6,517,525 | B1 | 2/2003 | Berthou |
| 6,518,479 | B1 | 2/2003 | Graef |
| 6,520,947 | B1 | 2/2003 | Tilly et al. |
| 6,521,811 | B1 | 2/2003 | Lassen |
| 6,521,812 | B1 | 2/2003 | Graef |
| 6,524,294 | B1 | 2/2003 | Hilston et al. |
| 6,525,240 | B1 | 2/2003 | Graef |
| 6,528,698 | B2 | 3/2003 | Mizutani et al. |
| 6,529,860 | B1 | 3/2003 | Strumolo et al. |
| 6,531,025 | B1 | 3/2003 | Lender et al. |
| 6,531,027 | B1 | 3/2003 | Lender et al. |
| 6,534,149 | B1 | 3/2003 | Daley et al. |
| 6,559,081 | B1 | 5/2003 | Erspamer |
| 6,559,239 | B1 | 5/2003 | Riegel et al. |
| 6,562,168 | B1 | 5/2003 | Schmitt et al. |
| 6,562,192 | B1 | 5/2003 | Hamilton |
| 6,569,137 | B2 | 5/2003 | Suzuki et al. |
| 6,573,422 | B1 | 6/2003 | Rosenfeld |
| 6,585,713 | B1 | 7/2003 | LaMahieu et al. |
| 6,585,858 | B1 | 7/2003 | Otto et al. |
| 6,602,234 | B2 | 8/2003 | Klemp et al. |
| 6,605,070 | B2 | 8/2003 | Ludwig et al. |
| 6,605,172 | B1 | 8/2003 | Anderson et al. |
| 6,605,752 | B2 | 8/2003 | Magnusson et al. |
| 6,610,900 | B1 | 8/2003 | Tanzer |
| 6,630,054 | B1 | 10/2003 | Graef |
| 6,632,209 | B1 | 10/2003 | Chmielewski |
| 6,632,504 | B1 | 10/2003 | Gillespie et al. |
| 6,645,569 | B2 | 11/2003 | Cramer et al. |
| 6,646,180 | B1 | 11/2003 | Chmielewski |
| 6,648,869 | B1 | 11/2003 | Gillies et al. |
| 6,648,870 | B2 | 11/2003 | Itoh et al. |
| 6,648,871 | B2 | 11/2003 | Kusibojoska et al. |
| 6,649,807 | B2 | 11/2003 | Mizutani |
| 6,649,810 | B1 | 11/2003 | Minato et al. |
| 6,657,015 | B1 | 12/2003 | Riegel et al. |
| 6,657,102 | B2 | 12/2003 | Furuya |
| 6,667,424 | B1 | 12/2003 | Hamilton |
| 6,670,522 | B1 | 12/2003 | Graef |
| 6,673,982 | B1 | 1/2004 | Chen |
| 6,673,983 | B1 | 1/2004 | Graef |
| 6,673,985 | B2 | 1/2004 | Mizutani |
| 6,682,515 | B1 | 1/2004 | Mizutani et al. |
| 6,682,516 | B2 | 1/2004 | Johnston |
| 6,689,115 | B1 | 2/2004 | Popp et al. |
| 6,689,934 | B2 | 2/2004 | Dodge, II et al. |
| 6,695,827 | B2 | 2/2004 | Chen |
| 6,700,034 | B1 | 3/2004 | Lindsay et al. |
| 6,703,538 | B2 | 3/2004 | Lassen |
| 6,705,465 | B2 | 3/2004 | Ling et al. |
| 6,706,129 | B2 | 3/2004 | Ando et al. |
| 6,706,943 | B2 | 3/2004 | Onishi |
| 6,710,224 | B2 | 3/2004 | Chmielewski et al. |
| 6,710,225 | B1 | 3/2004 | Everett et al. |
| 6,716,205 | B2 | 4/2004 | Popp et al. |
| 6,716,441 | B1 | 4/2004 | Roe et al. |
| 6,717,029 | B2 | 4/2004 | Baker |
| 6,726,668 | B2 | 4/2004 | Underhill et al. |
| 6,726,792 | B1 | 4/2004 | Johnson et al. |
| 6,730,387 | B2 | 5/2004 | Rezai et al. |
| 6,734,335 | B1 | 5/2004 | Graef |
| 6,746,976 | B1 | 6/2004 | Urankar et al. |
| 6,790,798 | B1 | 9/2004 | Suzuki et al. |
| 6,802,834 | B2 | 10/2004 | Melius et al. |
| 6,809,158 | B2 | 10/2004 | Ikeuchi et al. |
| 6,811,642 | B2 | 11/2004 | Ochi |
| 6,818,083 | B2 | 11/2004 | Mcamish et al. |
| 6,818,166 | B2 | 11/2004 | Edwardson et al. |
| 6,830,800 | B2 | 12/2004 | Curro et al. |
| 6,832,905 | B2 | 12/2004 | Delzer et al. |
| 6,840,929 | B2 | 1/2005 | Kurata |
| 6,846,374 | B2 | 1/2005 | Popp |
| 6,858,771 | B2 | 2/2005 | Yoshimasa |
| 6,863,933 | B2 | 3/2005 | Cramer et al. |
| 6,863,960 | B2 | 3/2005 | Curro et al. |
| 6,867,345 | B2 | 3/2005 | Shimoe et al. |
| 6,867,346 | B1 | 3/2005 | Dopps |
| 6,878,433 | B2 | 4/2005 | Curro et al. |
| 6,878,647 | B1 | 4/2005 | Rezai |
| 6,880,211 | B2 | 4/2005 | Jackson et al. |
| 6,891,080 | B2 | 5/2005 | Minato |
| 6,904,865 | B2 | 6/2005 | Klofta |

(56) References Cited

U.S. PATENT DOCUMENTS 6,911,574 B1 6/2005 Mizutani
6,923,797 B2 8/2005 Shinohara et al.
6,923,926 B2 8/2005 Walter et al.
6,926,703 B2 8/2005 Sugito
6,929,629 B2 8/2005 Drevik et al.
6,939,914 B2 9/2005 Qin et al.
6,946,585 B2 9/2005 Brown
6,953,451 B2 10/2005 Berba
6,955,733 B2 10/2005 Henry et al.
6,962,578 B1 11/2005 Lavon
6,962,645 B2 11/2005 Graef
6,965,058 B1 11/2005 Raidel
6,969,781 B2 11/2005 Graef
6,972,010 B2 12/2005 Pesce et al.
6,972,011 B2 12/2005 Maeda et al.
6,979,564 B2 12/2005 Glucksmann et al.
6,982,052 B2 1/2006 Daniels et al.
7,001,167 B2 2/2006 Venturino
7,014,632 B2 3/2006 Takino et al.
7,015,370 B2 3/2006 Watanabe
7,037,299 B2 5/2006 Turi et al.
7,037,571 B2 5/2006 Fish et al.
7,048,726 B2 5/2006 Kusagawa et al.
7,056,311 B2 6/2006 Kinoshita
7,067,711 B2 6/2006 Kinoshita et al.
7,073,373 B2 7/2006 La Fortune
7,078,583 B2 7/2006 Kudo
7,090,665 B2 8/2006 Ohashi
7,108,759 B2 9/2006 You
7,108,916 B2 9/2006 Ehrnsperger et al.
7,112,621 B2 9/2006 Rohrbaugh et al.
7,122,713 B2 10/2006 Komatsu
7,125,470 B2 10/2006 Graef
7,132,585 B2 11/2006 Kudo
7,147,628 B2 12/2006 Drevik
7,150,729 B2 12/2006 Shimada
7,154,019 B2 12/2006 Mishima et al.
7,160,281 B2 1/2007 Leminh et al.
7,163,528 B2 1/2007 Christon et al.
7,166,190 B2 1/2007 Graef
7,169,136 B2 1/2007 Otsubo
7,176,149 B2 2/2007 Dutkiewicz
7,183,360 B2 2/2007 Daniel et al.
7,189,888 B2 3/2007 Wang et al.
7,196,241 B2 3/2007 Kinoshita
7,199,211 B2 4/2007 Popp et al.
7,204,830 B2 4/2007 Mishima
7,207,978 B2 4/2007 Takino
7,219,403 B2 5/2007 Miyamoto et al.
7,220,251 B2 5/2007 Otsubo et al.
7,241,280 B2 7/2007 Christen et al.
7,249,570 B1 7/2007 Roberson
7,250,481 B2 7/2007 Jaworek et al.
7,252,657 B2 8/2007 Mishima
7,265,258 B2 9/2007 Hamilton
7,270,651 B2 9/2007 Adams et al.
7,285,178 B2 10/2007 Mischler et al.
7,306,582 B2 12/2007 Adams et al.
7,311,696 B2 12/2007 Christen et al.
7,311,968 B2 12/2007 Ehrnsperger et al.
7,312,372 B2 12/2007 Miyama
7,318,820 B2 1/2008 LaVon et al.
7,329,244 B2 2/2008 Otsubo
7,329,246 B2 2/2008 Kinoshita
7,335,810 B2 2/2008 Yoshimasa et al.
7,377,914 B2 5/2008 LaVon
7,429,689 B2 9/2008 Chen
7,435,244 B2 10/2008 Schroer et al.
7,465,373 B2 12/2008 Graef
7,500,969 B2 3/2009 Mishima
7,504,552 B2 3/2009 Tamura
7,521,109 B2 4/2009 Suzuki et al.
7,521,587 B2 4/2009 Busam et al.
7,537,832 B2 5/2009 Carlucci et al.
7,547,815 B2 6/2009 Ohashi
7,550,646 B2 6/2009 Tamura
7,563,257 B2 7/2009 Nakajima
7,588,561 B2 9/2009 Kenmochi
7,594,904 B2 9/2009 Rosenfeld
7,598,428 B2 10/2009 Gustavsson et al.
7,625,363 B2 12/2009 Yoshimasa
7,641,642 B2 1/2010 Murai et al.
7,648,490 B2 1/2010 Kuroda
7,652,111 B2 1/2010 Hermeling et al.
7,666,173 B2 2/2010 Mishima
7,666,174 B2 2/2010 Kawakami et al.
7,686,790 B2 3/2010 Rasmussen et al.
7,687,596 B2 3/2010 Hermeling et al.
7,695,461 B2 4/2010 Rosenfeld
7,696,402 B2 4/2010 Nishikawa
7,708,725 B2 5/2010 Tamagawa
7,717,150 B2 5/2010 Manabe
7,718,844 B2 5/2010 Olson
7,722,587 B2 5/2010 Suzuki et al.
7,722,590 B2 5/2010 Tsuji
7,727,217 B2 6/2010 Hancock-Cooke
7,732,039 B2 6/2010 Chavravarty et al.
7,736,351 B2 6/2010 Nigam
7,737,324 B2 6/2010 LaVon et al.
7,744,576 B2 6/2010 Busam et al.
7,744,578 B2 6/2010 Tanio et al.
7,750,203 B2 7/2010 Busam et al.
7,754,822 B2 7/2010 Daniel et al.
7,754,940 B2 7/2010 Brisebois
7,759,540 B2 7/2010 Litvay et al.
7,763,004 B2 7/2010 Beck
7,767,875 B2 8/2010 Olson
7,767,876 B2 8/2010 Davis et al.
7,767,878 B2 8/2010 Suzuki
7,772,420 B2 8/2010 Hermeling et al.
7,786,341 B2 8/2010 Schneider et al.
7,795,492 B2 9/2010 Vartiainen
7,803,145 B2 9/2010 Rosenfeld
7,825,291 B2 11/2010 Elfsberg et al.
7,838,722 B2 11/2010 Blessing et al.
7,850,672 B2 12/2010 Guidotti et al.
7,851,667 B2 12/2010 Becker et al.
7,855,314 B2 12/2010 Hanao
7,857,797 B2 12/2010 Kudo
7,858,842 B2 12/2010 Komatsu
7,884,259 B2 2/2011 Hanao
7,888,549 B2 2/2011 Jansson et al.
7,910,797 B2 3/2011 Nandrea
7,931,636 B2 4/2011 LaVon et al.
7,935,207 B2 5/2011 Zhao
7,935,861 B2 5/2011 Suzuki
7,938,813 B2 5/2011 Wang et al.
7,942,858 B2 5/2011 Francoeur
7,951,126 B2 5/2011 Nanjyo
7,956,236 B2 6/2011 Ponomarenko et al.
7,959,620 B2 6/2011 Miura et al.
7,982,091 B2 7/2011 Konawa
7,993,319 B2 8/2011 Sperl
8,017,827 B2 9/2011 Hundorf et al.
8,029,486 B2 10/2011 Nakajima
8,030,536 B2 10/2011 Ponomarenko et al.
8,034,991 B2 10/2011 Bruzadin et al.
8,039,684 B2 10/2011 Guidotti et al.
8,052,454 B2 11/2011 Polnyi
8,057,620 B2 11/2011 Perego et al.
8,109,915 B2 2/2012 Shimoe
8,124,828 B2 2/2012 Kline et al.
8,133,212 B2 3/2012 Takada
8,148,598 B2 4/2012 Tsang et al.
8,163,124 B2 4/2012 Moriura et al.
8,167,862 B2 5/2012 Digiacomantonio et al.
8,173,858 B2 5/2012 Kuroda
8,178,747 B2 5/2012 Venturino et al.
8,183,430 B2 5/2012 Hakansson et al.
8,186,296 B2 5/2012 Brown et al.
8,187,239 B2 5/2012 LaVon et al.
8,187,240 B2 5/2012 Busam et al.
8,198,506 B2 6/2012 Venturino et al.
8,211,815 B2 7/2012 Baker

(56) References Cited

U.S. PATENT DOCUMENTS

| | | | | |
|---|---|---|---|---|
| 8,236,715 | B2 | 8/2012 | Schmidt et al. | |
| 8,237,012 | B2 | 8/2012 | Miyama | |
| 8,246,594 | B2 | 8/2012 | Sperl | |
| 8,258,367 | B2 | 9/2012 | Lawson et al. | |
| 8,268,424 | B1 | 9/2012 | Suzuki | |
| 8,273,943 | B2 | 9/2012 | Noda | |
| 8,282,617 | B2 | 10/2012 | Kaneda | |
| 8,283,516 | B2 | 10/2012 | Litvay | |
| 8,317,766 | B2 | 11/2012 | Naoto | |
| 8,317,768 | B2 | 11/2012 | Larsson | |
| 8,319,005 | B2 | 11/2012 | Becker et al. | |
| 8,343,123 | B2 | 1/2013 | Noda | |
| 8,343,296 | B2 | 1/2013 | Blessing et al. | |
| 8,360,977 | B2 | 1/2013 | Marttila | |
| 8,361,047 | B2 | 1/2013 | Mukai | |
| 8,377,025 | B2 | 2/2013 | Nakajima | |
| 8,450,555 | B2 | 5/2013 | Nahn et al. | |
| 8,496,637 | B2 | 7/2013 | Hundorf et al. | |
| 8,519,213 | B2 | 8/2013 | Venturino et al. | |
| 8,524,355 | B2 | 9/2013 | Nakaoka | |
| 8,552,252 | B2 | 10/2013 | Hundorf et al. | |
| 8,568,566 | B2 | 10/2013 | Jackels et al. | |
| 8,569,571 | B2 | 10/2013 | Kline et al. | |
| 8,581,019 | B2 | 11/2013 | Carlucci et al. | |
| 8,603,058 | B2 | 12/2013 | Sperl et al. | |
| 8,604,270 | B2 | 12/2013 | Venturino et al. | |
| 8,633,347 | B2 | 1/2014 | Bianco et al. | |
| 8,664,468 | B2 | 3/2014 | Lawson et al. | |
| 8,674,170 | B2 | 3/2014 | Busam et al. | |
| 8,734,417 | B2 | 5/2014 | LaVon et al. | |
| 8,766,031 | B2 | 7/2014 | Becker et al. | |
| 8,772,570 | B2 | 7/2014 | Kawakami et al. | |
| 8,784,594 | B2 | 7/2014 | Blessing et al. | |
| 8,785,715 | B2 | 7/2014 | Wright et al. | |
| 8,791,318 | B2 | 7/2014 | Becker et al. | |
| 8,936,584 | B2 | 1/2015 | Zander et al. | |
| 9,056,034 | B2 | 6/2015 | Akiyama | |
| 9,326,896 | B2 | 5/2016 | Schaefer et al. | |
| 9,375,358 | B2 | 6/2016 | Ehrnsperger et al. | |
| 10,842,690 | B2 * | 11/2020 | Bianchi ................. | A61F 13/532 |
| 2001/0007065 | A1 | 7/2001 | Blanchard | |
| 2001/0008964 | A1 | 7/2001 | Kurata et al. | |
| 2001/0016548 | A1 | 8/2001 | Kugler et al. | |
| 2001/0020157 | A1 | 9/2001 | Mizutani | |
| 2001/0037101 | A1 | 11/2001 | Allan et al. | |
| 2001/0044610 | A1 | 11/2001 | Kim | |
| 2002/0007167 | A1 | 1/2002 | Dan | |
| 2002/0007169 | A1 | 1/2002 | Graef et al. | |
| 2002/0016122 | A1 | 2/2002 | Curro et al. | |
| 2002/0016579 | A1 | 2/2002 | Stenberg | |
| 2002/0045881 | A1 | 4/2002 | Kusibojoska et al. | |
| 2002/0056516 | A1 | 5/2002 | Ochi | |
| 2002/0058919 | A1 | 5/2002 | Hamilton et al. | |
| 2002/0062112 | A1 | 5/2002 | Mizutani | |
| 2002/0062115 | A1 | 5/2002 | Wada et al. | |
| 2002/0062116 | A1 | 5/2002 | Mizutani et al. | |
| 2002/0065498 | A1 | 5/2002 | Ohashi | |
| 2002/0072471 | A1 | 6/2002 | Ikeuchi et al. | |
| 2002/0082575 | A1 | 6/2002 | Dan | |
| 2002/0087139 | A1 | 7/2002 | Popp et al. | |
| 2002/0095127 | A1 | 7/2002 | Fish et al. | |
| 2002/0102392 | A1 | 8/2002 | Fish et al. | |
| 2002/0115969 | A1 | 8/2002 | Maeda et al. | |
| 2002/0123728 | A1 | 9/2002 | Graef et al. | |
| 2002/0123848 | A1 | 9/2002 | Schneiderman et al. | |
| 2002/0151634 | A1 | 10/2002 | Rohrbaugh et al. | |
| 2002/0151861 | A1 | 10/2002 | Klemp et al. | |
| 2002/0173767 | A1 | 11/2002 | Popp et al. | |
| 2002/0192366 | A1 | 12/2002 | Cramer et al. | |
| 2002/0197695 | A1 | 12/2002 | Glucksmann et al. | |
| 2003/0023215 | A1 * | 1/2003 | Baker .................. | A61F 13/532<br>604/367 |
| 2003/0036741 | A1 | 2/2003 | Abba et al. | |
| 2003/0078553 | A1 | 4/2003 | Wada | |
| 2003/0084983 | A1 | 5/2003 | Rangachari et al. | |
| 2003/0088223 | A1 | 5/2003 | Vogt et al. | |
| 2003/0105190 | A1 | 6/2003 | Diehl et al. | |
| 2003/0109839 | A1 | 6/2003 | Costae et al. | |
| 2003/0114811 | A1 | 6/2003 | Christen et al. | |
| 2003/0114816 | A1 | 6/2003 | Underhill | |
| 2003/0114818 | A1 | 6/2003 | Benecke et al. | |
| 2003/0115969 | A1 | 6/2003 | Koyano et al. | |
| 2003/0119401 | A1 * | 6/2003 | Chakravarty ......... | A61F 13/536<br>442/327 |
| 2003/0120235 | A1 | 6/2003 | Boulanger | |
| 2003/0120249 | A1 | 6/2003 | Wulz et al. | |
| 2003/0135176 | A1 | 7/2003 | Delzer et al. | |
| 2003/0135181 | A1 | 7/2003 | Chen et al. | |
| 2003/0135182 | A1 | 7/2003 | Woon et al. | |
| 2003/0139712 | A1 | 7/2003 | Dodge | |
| 2003/0139715 | A1 | 7/2003 | Dodge | |
| 2003/0139718 | A1 | 7/2003 | Graef | |
| 2003/0144642 | A1 | 7/2003 | Dopps | |
| 2003/0144644 | A1 | 7/2003 | Murai et al. | |
| 2003/0148684 | A1 | 8/2003 | Cramer et al. | |
| 2003/0148694 | A1 | 8/2003 | Ghiam | |
| 2003/0158530 | A1 | 8/2003 | Diehl et al. | |
| 2003/0158531 | A1 | 8/2003 | Chmielewski | |
| 2003/0158532 | A1 | 8/2003 | Magee et al. | |
| 2003/0167045 | A1 | 9/2003 | Graef | |
| 2003/0171727 | A1 | 9/2003 | Graef | |
| 2003/0208175 | A1 | 11/2003 | Gross | |
| 2003/0225385 | A1 | 12/2003 | Glaug | |
| 2003/0233082 | A1 | 12/2003 | Kline et al. | |
| 2003/0236512 | A1 | 12/2003 | Baker | |
| 2004/0019338 | A1 | 1/2004 | Litvay et al. | |
| 2004/0022998 | A1 | 2/2004 | Miyamoto et al. | |
| 2004/0033750 | A1 | 2/2004 | Everett | |
| 2004/0063367 | A1 | 4/2004 | Dodge | |
| 2004/0064113 | A1 | 4/2004 | Erdman | |
| 2004/0064115 | A1 | 4/2004 | Arora | |
| 2004/0064116 | A1 | 4/2004 | Arora | |
| 2004/0064125 | A1 | 4/2004 | Justmann et al. | |
| 2004/0065420 | A1 | 4/2004 | Graef | |
| 2004/0082928 | A1 | 4/2004 | Pesce et al. | |
| 2004/0097895 | A1 | 5/2004 | Busam et al. | |
| 2004/0122411 | A1 | 6/2004 | Hancock-Cooke | |
| 2004/0127131 | A1 | 7/2004 | Potnis | |
| 2004/0127871 | A1 | 7/2004 | Odorzynski | |
| 2004/0127872 | A1 | 7/2004 | Petryk | |
| 2004/0134596 | A1 | 7/2004 | Rosati et al. | |
| 2004/0138633 | A1 | 7/2004 | Mishima et al. | |
| 2004/0147890 | A1 | 7/2004 | Nakahata et al. | |
| 2004/0158212 | A1 | 8/2004 | Ponomarenko et al. | |
| 2004/0162536 | A1 | 8/2004 | Busam et al. | |
| 2004/0167486 | A1 | 8/2004 | Busam et al. | |
| 2004/0167489 | A1 | 8/2004 | Kellenberger et al. | |
| 2004/0170813 | A1 | 9/2004 | Digiacomantonio et al. | |
| 2004/0193127 | A1 | 9/2004 | Hansson | |
| 2004/0204698 | A1 * | 10/2004 | Zenker .............. | A61F 13/15203<br>604/385.01 |
| 2004/0214499 | A1 | 10/2004 | Qin et al. | |
| 2004/0215160 | A1 | 10/2004 | Chmielewski | |
| 2004/0220541 | A1 | 11/2004 | Suzuki et al. | |
| 2004/0225271 | A1 | 11/2004 | Datta et al. | |
| 2004/0231065 | A1 | 11/2004 | Daniel et al. | |
| 2004/0236299 | A1 | 11/2004 | Tsang et al. | |
| 2004/0236455 | A1 | 11/2004 | Woltman et al. | |
| 2004/0249355 | A1 | 12/2004 | Tanio et al. | |
| 2004/0260259 | A1 | 12/2004 | Baker | |
| 2005/0001929 | A1 | 1/2005 | Waksmundzki et al. | |
| 2005/0004543 | A1 | 1/2005 | Schroer et al. | |
| 2005/0004548 | A1 | 1/2005 | Otsubo et al. | |
| 2005/0008839 | A1 | 1/2005 | Cramer et al. | |
| 2005/0018258 | A1 | 1/2005 | Miyagi | |
| 2005/0038401 | A1 | 2/2005 | Suzuki et al. | |
| 2005/0070867 | A1 | 3/2005 | Beruda et al. | |
| 2005/0085784 | A1 | 4/2005 | LeMinh et al. | |
| 2005/0090789 | A1 | 4/2005 | Graef | |
| 2005/0101929 | A1 | 5/2005 | Waksmundzki et al. | |
| 2005/0148258 | A1 | 7/2005 | Chakravarty | |
| 2005/0148961 | A1 | 7/2005 | Sosalla et al. | |
| 2005/0148990 | A1 | 7/2005 | Shimoe | |
| 2005/0154363 | A1 | 7/2005 | Minato | |

(56) References Cited

U.S. PATENT DOCUMENTS

2005/0159720 A1 7/2005 Gentilcore
2005/0165208 A1 7/2005 Popp et al.
2005/0171499 A1 8/2005 Nigam et al.
2005/0176910 A1 8/2005 Jaworek et al.
2005/0203475 A1 9/2005 LaVon et al.
2005/0215752 A1 9/2005 Popp et al.
2005/0217791 A1 10/2005 Costello et al.
2005/0229543 A1 10/2005 Tippey
2005/0234414 A1 10/2005 Liu et al.
2005/0245684 A1 11/2005 Daniel et al.
2005/0288645 A1 12/2005 LaVon
2005/0288646 A1 12/2005 LaVon
2006/0004334 A1 1/2006 Schlinz et al.
2006/0021695 A1 2/2006 Blessing et al.
2006/0024433 A1 2/2006 Blessing et al.
2006/0069367 A1 3/2006 Waksmundzki et al.
2006/0069371 A1 3/2006 Ohashi et al.
2006/0073969 A1 4/2006 Torli et al.
2006/0081348 A1 4/2006 Graef
2006/0129114 A1 6/2006 Mason et al.
2006/0142724 A1 6/2006 Watanabe
2006/0155057 A1 7/2006 Hermeling et al.
2006/0155254 A1 7/2006 Sanz et al.
2006/0167215 A1 7/2006 Hermeling et al.
2006/0177647 A1 8/2006 Schmidt et al.
2006/0178071 A1 8/2006 Schmidt et al.
2006/0184146 A1 8/2006 Suzuki
2006/0184149 A1 8/2006 Kasai et al.
2006/0189954 A1 8/2006 Kudo
2006/0202380 A1 9/2006 Bentley
2006/0206091 A1 9/2006 Cole
2006/0211828 A1 9/2006 Daniel et al.
2006/0240229 A1 10/2006 Ehrnsperger et al.
2006/0264860 A1 11/2006 Beck
2006/0264861 A1 11/2006 Lavon et al.
2006/0271010 A1 11/2006 LaVon et al.
2007/0027436 A1 2/2007 Nakagawa et al.
2007/0043191 A1 2/2007 Hermeling et al.
2007/0043330 A1 2/2007 Lankhof et al.
2007/0044903 A1 3/2007 Wisneski et al.
2007/0049892 A1 3/2007 Lord et al.
2007/0049897 A1 3/2007 LaVon et al.
2007/0073253 A1 3/2007 Miyama
2007/0078422 A1 4/2007 Glaug
2007/0088308 A1 4/2007 Ehrnsperger et al.
2007/0093164 A1 4/2007 Nakaoka
2007/0093767 A1 4/2007 Carlucci et al.
2007/0100307 A1 5/2007 Nomoto
2007/0106013 A1 5/2007 Adachi et al.
2007/0118087 A1 5/2007 Flohr et al.
2007/0123834 A1 5/2007 McDowall et al.
2007/0156108 A1 7/2007 Becker et al.
2007/0167928 A1 7/2007 Becker et al.
2007/0179464 A1 8/2007 Becker et al.
2007/0179469 A1 8/2007 Takahashi et al.
2007/0191798 A1 8/2007 Glaug
2007/0219521 A1 9/2007 Hird et al.
2007/0219523 A1 9/2007 Bruun
2007/0239125 A9 10/2007 Erdman et al.
2007/0244455 A1* 10/2007 Hansson ............. A61F 13/4704
604/385.28
2007/0246147 A1 10/2007 Venturino et al.
2007/0255245 A1 11/2007 Asp et al.
2007/0282288 A1 12/2007 Noda
2007/0282290 A1 12/2007 Cole
2007/0282291 A1 12/2007 Cole
2008/0027402 A1 1/2008 Schmidt et al.
2008/0032035 A1 2/2008 Schmidt et al.
2008/0091159 A1 4/2008 Carlucci et al.
2008/0119810 A1 5/2008 Kuroda
2008/0125735 A1 5/2008 Busam et al.
2008/0132864 A1 6/2008 Lawson et al.
2008/0208154 A1 8/2008 Oetjen et al.
2008/0221538 A1 9/2008 Zhao
2008/0221539 A1 9/2008 Zhao
2008/0228158 A1 9/2008 Sue et al.
2008/0262459 A1 10/2008 Kamoto
2008/0268194 A1 10/2008 Kim et al.
2008/0274227 A1 11/2008 Boatman et al.
2008/0281287 A1 11/2008 Marcelo
2008/0312617 A1 12/2008 Hundorf et al.
2008/0312618 A1 12/2008 Hundorf et al.
2008/0312619 A1 12/2008 Hundorf et al.
2008/0312620 A1 12/2008 Ashton et al.
2008/0312621 A1 12/2008 Hundorf et al.
2008/0312622 A1 12/2008 Hundorf et al.
2008/0312623 A1 12/2008 Hundorf et al.
2008/0312624 A1 12/2008 Hundorf et al.
2008/0312625 A1 12/2008 Hundorf et al.
2008/0312627 A1 12/2008 Takeuchi
2008/0312628 A1 12/2008 Hundorf et al.
2009/0056867 A1 3/2009 Moriura et al.
2009/0058994 A1 3/2009 Kao et al.
2009/0062760 A1 3/2009 Wright et al.
2009/0112173 A1 4/2009 Bissah
2009/0112175 A1 4/2009 Bissah et al.
2009/0157022 A1 6/2009 Macdonald
2009/0192035 A1 7/2009 Stueven et al.
2009/0240220 A1 9/2009 Macdonald
2009/0247977 A1 10/2009 Takeuchi
2009/0258994 A1 10/2009 Stueven et al.
2009/0270825 A1 10/2009 Wciorka et al.
2009/0298963 A1 12/2009 Matsumoto et al.
2009/0299312 A1 12/2009 Macdonald
2009/0306618 A1 12/2009 Kudo
2009/0318884 A1 12/2009 Meyer et al.
2009/0326494 A1 12/2009 Uchida et al.
2009/0326497 A1 12/2009 Schmidt
2010/0004614 A1 1/2010 Ashton et al.
2010/0051166 A1 3/2010 Hundorf et al.
2010/0062165 A1 3/2010 Suzuki
2010/0062934 A1 3/2010 Suzuki
2010/0063470 A1 3/2010 Suzuki
2010/0068520 A1 3/2010 Stueven et al.
2010/0100065 A1 4/2010 Bianco
2010/0115237 A1 5/2010 Brewer et al.
2010/0121296 A1 5/2010 Noda
2010/0137773 A1 6/2010 Gross
2010/0137823 A1 6/2010 Corneliusson
2010/0198179 A1 8/2010 Noda
2010/0228210 A1 9/2010 Busam et al.
2010/0241096 A1 9/2010 LaVon et al.
2010/0241097 A1 9/2010 Nigam et al.
2010/0262099 A1 10/2010 Klofta
2010/0262104 A1 10/2010 Carlucci et al.
2010/0274208 A1 10/2010 Gabrielii
2010/0274210 A1 10/2010 Noda
2010/0305537 A1 12/2010 Ashton et al.
2010/0312208 A1 12/2010 Bond et al.
2010/0324521 A1 12/2010 Mukai
2010/0324523 A1 12/2010 Mukai
2011/0034603 A1 2/2011 Fujino et al.
2011/0041999 A1 2/2011 Hundorf et al.
2011/0060301 A1 3/2011 Nishikawa et al.
2011/0060303 A1 3/2011 Bissah
2011/0066127 A1 3/2011 Kuwano
2011/0071486 A1 3/2011 Harada
2011/0092944 A1 4/2011 Sagisaka
2011/0112498 A1 5/2011 Nhan et al.
2011/0125120 A1 5/2011 Nishitani
2011/0130732 A1 6/2011 Jackels et al.
2011/0130737 A1 6/2011 Sagisaka
2011/0137276 A1 6/2011 Yoshikawa
2011/0144602 A1 6/2011 Long
2011/0144604 A1 6/2011 Noda
2011/0144606 A1 6/2011 Nandrea
2011/0152813 A1 6/2011 Ellingson
2011/0166540 A1 7/2011 Yang et al.
2011/0172630 A1 7/2011 Nomoto
2011/0174430 A1 7/2011 Zhao
2011/0196330 A1 8/2011 Hammons et al.
2011/0208147 A1 8/2011 Kawakami et al.
2011/0250413 A1 10/2011 Lu et al.
2011/0268932 A1 11/2011 Catalan et al.

(56) References Cited

U.S. PATENT DOCUMENTS

| | | | | |
|---|---|---|---|---|
| 2011/0274834 | A1 | 11/2011 | Brown et al. | |
| 2011/0288513 | A1 | 11/2011 | Hundorf et al. | |
| 2011/0288514 | A1 | 11/2011 | Kuroda | |
| 2011/0295222 | A1 | 12/2011 | Becker et al. | |
| 2011/0319846 | A1 | 12/2011 | Rinnert et al. | |
| 2011/0319848 | A1 | 12/2011 | McKiernan et al. | |
| 2011/0319851 | A1 | 12/2011 | Kudo | |
| 2012/0004633 | A1 | 1/2012 | R Marcelo | |
| 2012/0016326 | A1 | 1/2012 | Brennan et al. | |
| 2012/0022479 | A1 | 1/2012 | Cotton | |
| 2012/0035566 | A1 | 2/2012 | Sagisaka | |
| 2012/0035576 | A1 | 2/2012 | Ichikawa | |
| 2012/0064792 | A1 | 3/2012 | Bauduin | |
| 2012/0071848 | A1 | 3/2012 | Zhang | |
| 2012/0165771 | A1 | 6/2012 | Ruman et al. | |
| 2012/0165776 | A1 | 6/2012 | Rinnert et al. | |
| 2012/0170779 | A1 | 7/2012 | Hildebrandt | |
| 2012/0175056 | A1 | 7/2012 | Tsang | |
| 2012/0184934 | A1 | 7/2012 | Venturino | |
| 2012/0220972 | A1 | 8/2012 | Kawamura et al. | |
| 2012/0232514 | A1 | 9/2012 | Baker | |
| 2012/0238977 | A1 | 9/2012 | Oku | |
| 2012/0253306 | A1 | 10/2012 | Otsubo | |
| 2012/0256750 | A1 | 10/2012 | Novak | |
| 2012/0271262 | A1 | 10/2012 | Venturino | |
| 2012/0312491 | A1 | 12/2012 | Jackels et al. | |
| 2012/0316046 | A1 | 12/2012 | Jackels et al. | |
| 2012/0316523 | A1 | 12/2012 | Hippe et al. | |
| 2012/0316526 | A1 | 12/2012 | Rosati et al. | |
| 2012/0316527 | A1 | 12/2012 | Rosati et al. | |
| 2012/0316528 | A1 | 12/2012 | Kreuzer et al. | |
| 2012/0316529 | A1* | 12/2012 | Kreuzer ................ | A61F 13/536 604/366 |
| 2012/0316530 | A1* | 12/2012 | Armstrong-Ostle ........................ | A61F 13/539 604/366 |
| 2012/0323195 | A1 | 12/2012 | Ehrnsperger et al. | |
| 2012/0323201 | A1 | 12/2012 | Bissah | |
| 2012/0323202 | A1 | 12/2012 | Bissah | |
| 2013/0035656 | A1 | 2/2013 | Moriya et al. | |
| 2013/0041334 | A1 | 2/2013 | Prioleau | |
| 2013/0053808 | A1 | 2/2013 | Hill | |
| 2013/0178811 | A1 | 7/2013 | Kikuchi et al. | |
| 2013/0211354 | A1 | 8/2013 | Tsuji et al. | |
| 2013/0211358 | A1 | 8/2013 | Kikkawa et al. | |
| 2013/0218115 | A1 | 8/2013 | Katsuragawa et al. | |
| 2013/0226119 | A1 | 8/2013 | Katsuragawa et al. | |
| 2013/0226120 | A1 | 8/2013 | Van De Maele | |
| 2013/0310784 | A1 | 11/2013 | Bryant et al. | |
| 2013/0331806 | A1* | 12/2013 | Rosati ............... | A61F 13/53743 604/366 |
| 2014/0005622 | A1 | 1/2014 | Wirtz et al. | |
| 2014/0005623 | A1 | 1/2014 | Wirtz et al. | |
| 2014/0027066 | A1 | 1/2014 | Jackels et al. | |
| 2014/0039437 | A1 | 2/2014 | Van De Maele | |
| 2014/0102183 | A1 | 4/2014 | Agami et al. | |
| 2014/0121623 | A1 | 5/2014 | Kirby et al. | |
| 2014/0121625 | A1 | 5/2014 | Kirby et al. | |
| 2014/0135726 | A1 | 5/2014 | Busam et al. | |
| 2014/0142531 | A1 | 5/2014 | Sasayama et al. | |
| 2014/0163500 | A1 | 6/2014 | Roe et al. | |
| 2014/0163501 | A1 | 6/2014 | Ehrnsperger et al. | |
| 2014/0163502 | A1 | 6/2014 | Arizti et al. | |
| 2014/0163503 | A1 | 6/2014 | Arizti et al. | |
| 2014/0163504 | A1 | 6/2014 | Bianchi | |
| 2014/0163506 | A1 | 6/2014 | Roe et al. | |
| 2014/0163511 | A1 | 6/2014 | Roe et al. | |
| 2014/0171893 | A1 | 6/2014 | Lawson et al. | |
| 2014/0299815 | A1 | 10/2014 | Ueda et al. | |
| 2014/0318694 | A1 | 10/2014 | Blessing et al. | |
| 2014/0324007 | A1 | 10/2014 | Hundorf et al. | |
| 2014/0324008 | A1 | 10/2014 | Hundorf et al. | |
| 2014/0371701 | A1 | 12/2014 | Bianchi et al. | |
| 2015/0065975 | A1 | 3/2015 | Roe et al. | |
| 2015/0065981 | A1 | 3/2015 | Roe et al. | |
| 2015/0065986 | A1 | 3/2015 | Blessing et al. | |
| 2015/0073366 | A1* | 3/2015 | Ehrnsperger .......... | A61F 13/534 604/374 |
| 2015/0080821 | A1 | 3/2015 | Peri et al. | |
| 2015/0080837 | A1 | 3/2015 | Rosati et al. | |
| 2015/0080839 | A1 | 3/2015 | Tapp et al. | |
| 2015/0173959 | A1* | 6/2015 | Carlucci ............. | A61F 13/4758 604/367 |
| 2015/0173967 | A1 | 6/2015 | Kreuzer et al. | |
| 2015/0173968 | A1 | 6/2015 | Joseph | |
| 2015/0173979 | A1* | 6/2015 | Carlucci ............... | A61F 13/532 604/385.201 |
| 2015/0250662 | A1 | 9/2015 | Isele et al. | |
| 2015/0250663 | A1 | 9/2015 | Wagner et al. | |
| 2015/0273433 | A1 | 10/2015 | Nakatsuru et al. | |
| 2015/0342796 | A1 | 12/2015 | Bianchi | |
| 2016/0235596 | A1* | 8/2016 | Ehrnsperger .......... | A61F 13/537 |
| 2016/0235597 | A1* | 8/2016 | Ehrnsperger ...... | A61F 13/55115 |
| 2016/0235602 | A1* | 8/2016 | Ehrnsperger ............ | A61F 13/49 |
| 2016/0235603 | A1* | 8/2016 | Ehrnsperger ...... | A61F 13/55115 |
| 2016/0235604 | A1* | 8/2016 | Ehrnsperger ............ | A61F 13/53 |
| 2016/0235605 | A1* | 8/2016 | Ehrnsperger .......... | A61F 13/532 |
| 2017/0049636 | A1* | 2/2017 | Hardie ................ | A61F 13/4758 |
| 2017/0135872 | A1* | 5/2017 | Moriya ............. | A61F 13/51108 |
| 2017/0273833 | A1* | 9/2017 | Umemoto ......... | A61F 13/49406 |
| 2017/0312145 | A1* | 11/2017 | Bianchi ............... | A61F 13/5376 |
| 2017/0312146 | A1* | 11/2017 | Bianchi ................... | A61F 13/49 |
| 2017/0312147 | A1* | 11/2017 | Bianchi ............... | A61F 13/1565 |

FOREIGN PATENT DOCUMENTS

| | | | |
|---|---|---|---|
| CA | 2308961 | | 11/2000 |
| CA | 2487027 | | 12/2003 |
| CA | 2561521 | | 3/2007 |
| CA | 2630713 | | 11/2008 |
| CA | 2636673 | | 1/2009 |
| CA | 2712563 | | 8/2010 |
| CA | 2702001 | | 10/2010 |
| CN | 1238171 | A | 12/1999 |
| CN | 2362468 | Y | 2/2000 |
| CN | 1371671 | | 2/2001 |
| CN | 2527254 | Y | 12/2002 |
| CN | 2535020 | Y | 2/2003 |
| CN | 2548609 | Y | 5/2003 |
| CN | 1539391 | | 10/2004 |
| CN | 1939242 | | 4/2007 |
| CN | 1988864 | A | 6/2007 |
| CN | 101292930 | | 10/2008 |
| CN | 201263750 | | 7/2009 |
| CN | 201591689 | | 9/2010 |
| CN | 102076297 | A | 5/2011 |
| CN | 201855366 | U | 6/2011 |
| CN | 103648462 | A | 3/2014 |
| CN | 104837453 | A | 8/2015 |
| DE | 3205931 | C2 | 9/1983 |
| DE | 3608114 | A1 | 9/1987 |
| DE | 19732499 | | 2/1999 |
| DE | 10204937 | A1 | 8/2003 |
| EP | 083022 | | 7/1983 |
| EP | 149880 | | 7/1985 |
| EP | 0149880 | A2 | 7/1985 |
| EP | 203289 | | 12/1986 |
| EP | 0203289 | A2 | 12/1986 |
| EP | 0206208 | | 12/1986 |
| EP | 209561 | B1 | 1/1987 |
| EP | 297411 | B1 | 1/1989 |
| EP | 304957 | | 3/1989 |
| EP | 374542 | | 6/1990 |
| EP | 0403832 | | 12/1990 |
| EP | 481322 | B1 | 4/1992 |
| EP | 530438 | | 3/1993 |
| EP | 547847 | | 6/1993 |
| EP | 555346 | | 8/1993 |
| EP | 559476 | | 9/1993 |
| EP | 591647 | B2 | 4/1994 |
| EP | 597273 | B1 | 5/1994 |
| EP | 601610 | B2 | 6/1994 |
| EP | 632068 | | 1/1995 |
| EP | 0640330 | A1 | 3/1995 |

(56) References Cited

FOREIGN PATENT DOCUMENTS

| | | | |
|---|---|---|---|
| EP | 0668066 | | 9/1995 |
| EP | 685214 | | 12/1995 |
| EP | 687453 | | 12/1995 |
| EP | 0689817 | | 1/1996 |
| EP | 0691133 | | 1/1996 |
| EP | 0700673 | | 3/1996 |
| EP | 0394274 | | 7/1996 |
| EP | 725615 | | 8/1996 |
| EP | 758543 | | 2/1997 |
| EP | 0761194 | | 3/1997 |
| EP | 769284 | | 4/1997 |
| EP | 0781537 | | 7/1997 |
| EP | 783877 | B1 | 7/1997 |
| EP | 787472 | | 8/1997 |
| EP | 788874 | B1 | 8/1997 |
| EP | 799004 | | 10/1997 |
| EP | 822794 | B1 | 2/1998 |
| EP | 826351 | | 3/1998 |
| EP | 844861 | | 6/1998 |
| EP | 0737055 | | 8/1998 |
| EP | 863733 | | 9/1998 |
| EP | 971751 | | 9/1998 |
| EP | 0875224 | | 11/1998 |
| EP | 875224 | A1 | 11/1998 |
| EP | 880955 | | 12/1998 |
| EP | 891758 | | 1/1999 |
| EP | 0893115 | | 1/1999 |
| EP | 0724418 | | 3/1999 |
| EP | 0725613 | | 3/1999 |
| EP | 0725616 | | 3/1999 |
| EP | 904755 | | 3/1999 |
| EP | 0916327 | | 5/1999 |
| EP | 925769 | A2 | 6/1999 |
| EP | 933074 | | 8/1999 |
| EP | 937736 | | 8/1999 |
| EP | 941157 | | 9/1999 |
| EP | 947549 | | 10/1999 |
| EP | 951887 | B1 | 10/1999 |
| EP | 0951890 | | 10/1999 |
| EP | 2295493 | | 10/1999 |
| EP | 2305749 | | 10/1999 |
| EP | 2330152 | | 10/1999 |
| EP | 953326 | | 11/1999 |
| EP | 0978263 | A1 | 2/2000 |
| EP | 985397 | B1 | 3/2000 |
| EP | 0988846 | | 3/2000 |
| EP | 0778762 | | 4/2000 |
| EP | 1005847 | | 6/2000 |
| EP | 1008333 | | 6/2000 |
| EP | 1013252 | B1 | 6/2000 |
| EP | 1018999 | | 7/2000 |
| EP | 1019002 | B1 | 7/2000 |
| EP | 1019003 | B1 | 7/2000 |
| EP | 1022008 | | 7/2000 |
| EP | 1023884 | | 8/2000 |
| EP | 1053729 | | 11/2000 |
| EP | 1059072 | A2 | 12/2000 |
| EP | 1063954 | | 1/2001 |
| EP | 1071388 | | 1/2001 |
| EP | 1078618 | | 2/2001 |
| EP | 1088537 | A2 | 4/2001 |
| EP | 0796068 | | 5/2001 |
| EP | 752892 | | 7/2001 |
| EP | 1116479 | A2 | 7/2001 |
| EP | 0790839 | | 8/2001 |
| EP | 1132069 | | 9/2001 |
| EP | 1173128 | | 1/2002 |
| EP | 1175194 | B1 | 1/2002 |
| EP | 1184018 | | 3/2002 |
| EP | 1192312 | B1 | 4/2002 |
| EP | 1196122 | B2 | 4/2002 |
| EP | 1199059 | | 4/2002 |
| EP | 1199327 | | 4/2002 |
| EP | 1208824 | | 5/2002 |
| EP | 0793469 | | 6/2002 |
| EP | 1210925 | | 6/2002 |
| EP | 1224922 | | 7/2002 |
| EP | 1225857 | | 7/2002 |
| EP | 1253231 | | 10/2002 |
| EP | 1262531 | A1 | 12/2002 |
| EP | 1263374 | B1 | 12/2002 |
| EP | 0737056 | | 1/2003 |
| EP | 1275358 | | 1/2003 |
| EP | 1275361 | | 1/2003 |
| EP | 1293187 | | 3/2003 |
| EP | 1304986 | B1 | 5/2003 |
| EP | 1332742 | B1 | 8/2003 |
| EP | 1339368 | | 9/2003 |
| EP | 1374817 | | 1/2004 |
| EP | 1388334 | | 2/2004 |
| EP | 1402863 | | 3/2004 |
| EP | 962208 | | 8/2004 |
| EP | 1447066 | | 8/2004 |
| EP | 1447067 | | 8/2004 |
| EP | 1460987 | | 9/2004 |
| EP | 963749 | | 11/2004 |
| EP | 1495739 | | 1/2005 |
| EP | 1524955 | | 4/2005 |
| EP | 1920743 | | 4/2005 |
| EP | 1541103 | | 6/2005 |
| EP | 1551344 | | 7/2005 |
| EP | 1586289 | | 10/2005 |
| EP | 1588723 | | 10/2005 |
| EP | 1605882 | | 12/2005 |
| EP | 1609448 | | 12/2005 |
| EP | 1621166 | | 2/2006 |
| EP | 1621167 | | 2/2006 |
| EP | 1632206 | | 3/2006 |
| EP | 1642556 | | 4/2006 |
| EP | 1403419 | | 5/2006 |
| EP | 1656162 | | 5/2006 |
| EP | 1669046 | | 6/2006 |
| EP | 1688114 | | 8/2006 |
| EP | 2314265 | | 8/2006 |
| EP | 1723939 | | 11/2006 |
| EP | 1738727 | | 1/2007 |
| EP | 1754461 | | 2/2007 |
| EP | 1787611 | | 5/2007 |
| EP | 1813238 | | 8/2007 |
| EP | 2008626 | | 12/2008 |
| EP | 2055279 | A1 | 5/2009 |
| EP | 2093049 | | 8/2009 |
| EP | 2130522 | | 12/2009 |
| EP | 1621165 | | 4/2010 |
| EP | 2444046 | | 4/2012 |
| EP | 2532328 | | 12/2012 |
| EP | 2532329 | A1 | 12/2012 |
| EP | 2532332 | A1 | 12/2012 |
| EP | 2656826 | | 10/2013 |
| EP | 2679210 | A1 | 1/2014 |
| EP | 2740449 | | 6/2014 |
| EP | 2740450 | | 6/2014 |
| EP | 2740452 | | 6/2014 |
| ES | 2213491 | | 8/2004 |
| FR | 2566631 | | 1/1986 |
| FR | 2583377 | | 12/1986 |
| FR | 2612770 | | 9/1988 |
| FR | 2810234 | | 12/2001 |
| GB | 1333081 | A | 8/1971 |
| GB | 1307441 | | 2/1973 |
| GB | 1513055 | | 6/1978 |
| GB | 2101468 | | 1/1983 |
| GB | 2170108 | | 7/1986 |
| GB | 2262873 | | 7/1993 |
| GB | 2288540 | A | 6/1994 |
| GB | 2354449 | | 3/2001 |
| GB | 2452260 | A | 10/2007 |
| GR | 851769 | | 11/1985 |
| IN | 0984/KOL/1999 | | 10/2005 |
| IN | 212479 | B | 3/2007 |
| IN | 208543 | B | 8/2007 |
| IN | 0980/MUM/2009 | | 6/2009 |
| JP | 5572928 | U | 5/1980 |
| JP | 598322 | U | 1/1984 |

(56) References Cited

FOREIGN PATENT DOCUMENTS

| | | | |
|---|---|---|---|
| JP | 630148323 | U | 9/1988 |
| JP | 2107250 | | 4/1990 |
| JP | 03224481 | B2 | 10/1991 |
| JP | 04122256 | | 4/1992 |
| JP | 04341368 | | 11/1992 |
| JP | 06191505 | | 7/1994 |
| JP | 06269475 | A | 9/1994 |
| JP | 07124193 | | 5/1995 |
| JP | 08215629 | | 8/1996 |
| JP | H10295728 | | 11/1998 |
| JP | 10328232 | | 12/1998 |
| JP | 11033056 | A | 2/1999 |
| JP | 11318980 | | 11/1999 |
| JP | 11320742 | | 11/1999 |
| JP | 2000232985 | | 8/2000 |
| JP | 2000238161 | | 9/2000 |
| JP | 2001037810 | | 2/2001 |
| JP | 2001046435 | A | 2/2001 |
| JP | 2001120597 | | 5/2001 |
| JP | 2001158074 | | 6/2001 |
| JP | 2001178768 | A | 7/2001 |
| JP | 2001198157 | | 7/2001 |
| JP | 2001224626 | A | 8/2001 |
| JP | 2001277394 | | 10/2001 |
| JP | 2001301857 | | 10/2001 |
| JP | 03420481 | B2 | 11/2001 |
| JP | 2001321397 | | 11/2001 |
| JP | 2001353174 | A | 12/2001 |
| JP | 2002052042 | A | 2/2002 |
| JP | 2002065718 | | 3/2002 |
| JP | 2002113800 | A | 4/2002 |
| JP | 2002165832 | | 6/2002 |
| JP | 2002165836 | | 6/2002 |
| JP | 2002178429 | | 6/2002 |
| JP | 2002272769 | A | 9/2002 |
| JP | 2002320641 | | 11/2002 |
| JP | 2002325792 | A | 11/2002 |
| JP | 2002325799 | A | 11/2002 |
| JP | 2002369841 | A | 12/2002 |
| JP | 2003126140 | | 5/2003 |
| JP | 2003153955 | A | 5/2003 |
| JP | 2003265523 | | 9/2003 |
| JP | 2003265524 | A | 9/2003 |
| JP | 2003275237 | | 9/2003 |
| JP | 2003325563 | | 11/2003 |
| JP | 2004089269 | | 3/2004 |
| JP | 03566012 | B2 | 6/2004 |
| JP | 03568146 | B2 | 6/2004 |
| JP | 03616077 | B2 | 11/2004 |
| JP | 2004337314 | A | 12/2004 |
| JP | 2004337385 | A | 12/2004 |
| JP | 2004350864 | | 12/2004 |
| JP | 03640475 | B2 | 1/2005 |
| JP | 2005000312 | A | 1/2005 |
| JP | 03660816 | B2 | 3/2005 |
| JP | 03676219 | B2 | 5/2005 |
| JP | 2005118339 | | 5/2005 |
| JP | 03688403 | B2 | 6/2005 |
| JP | 03705943 | B2 | 8/2005 |
| JP | 03719819 | B2 | 9/2005 |
| JP | 03724963 | B2 | 9/2005 |
| JP | 03725008 | B2 | 9/2005 |
| JP | 03737376 | B2 | 11/2005 |
| JP | 2006014792 | A | 1/2006 |
| JP | 03781617 | B2 | 3/2006 |
| JP | 2006110329 | | 4/2006 |
| JP | 2006513824 | T | 4/2006 |
| JP | 03801449 | B2 | 5/2006 |
| JP | 2006116036 | A | 5/2006 |
| JP | 03850102 | B2 | 9/2006 |
| JP | 03850207 | B2 | 9/2006 |
| JP | 03856941 | B2 | 9/2006 |
| JP | 03868628 | B2 | 10/2006 |
| JP | 03874499 | B2 | 11/2006 |
| JP | 03877702 | B2 | 11/2006 |
| JP | 2006325639 | A | 12/2006 |
| JP | 2006346021 | | 12/2006 |
| JP | 03904356 | B2 | 1/2007 |
| JP | 2007007455 | A | 1/2007 |
| JP | 2007007456 | A | 1/2007 |
| JP | 03926042 | B2 | 3/2007 |
| JP | 03934855 | B2 | 3/2007 |
| JP | 2007089906 | A | 4/2007 |
| JP | 2007105198 | A | 4/2007 |
| JP | 2007130504 | | 5/2007 |
| JP | 2007152033 | A | 6/2007 |
| JP | 03986210 | B2 | 7/2007 |
| JP | 03986222 | B2 | 7/2007 |
| JP | 2007167453 | | 7/2007 |
| JP | 2007175515 | A | 7/2007 |
| JP | 2007195665 | A | 8/2007 |
| JP | 2007267763 | A | 10/2007 |
| JP | 2007275491 | A | 10/2007 |
| JP | 04035341 | B2 | 11/2007 |
| JP | 04058281 | B2 | 12/2007 |
| JP | 04061086 | B2 | 12/2007 |
| JP | 04092319 | B2 | 3/2008 |
| JP | 2008080150 | A | 4/2008 |
| JP | 2008093289 | A | 4/2008 |
| JP | 04124322 | B2 | 5/2008 |
| JP | 2008119081 | A | 5/2008 |
| JP | 2008136739 | A | 6/2008 |
| JP | 2008136877 | A | 6/2008 |
| JP | 04148594 | B2 | 7/2008 |
| JP | 04148620 | B2 | 7/2008 |
| JP | 2008154606 | A | 7/2008 |
| JP | 04162609 | B2 | 8/2008 |
| JP | 04162637 | B2 | 8/2008 |
| JP | 04166923 | B2 | 8/2008 |
| JP | 04167406 | B2 | 8/2008 |
| JP | 04173723 | B2 | 8/2008 |
| JP | 04190675 | B2 | 9/2008 |
| JP | 04190693 | B2 | 9/2008 |
| JP | 04208338 | B2 | 10/2008 |
| JP | 2008246089 | | 10/2008 |
| JP | 4177770 | B2 | 11/2008 |
| JP | 04230971 | B2 | 12/2008 |
| JP | 2008295475 | A | 12/2008 |
| JP | 2008295713 | A | 12/2008 |
| JP | 04261593 | B2 | 2/2009 |
| JP | 2009028186 | | 2/2009 |
| JP | 2009112590 | | 5/2009 |
| JP | 04322228 | B2 | 6/2009 |
| JP | 2009136601 | | 6/2009 |
| JP | 2009142401 | A | 7/2009 |
| JP | 2009201878 | A | 9/2009 |
| JP | 04392936 | B2 | 10/2009 |
| JP | 2009232987 | A | 10/2009 |
| JP | 2009261777 | A | 11/2009 |
| JP | 2009291473 | A | 12/2009 |
| JP | 2009297048 | A | 12/2009 |
| JP | 2010017342 | | 1/2010 |
| JP | 04458702 | B2 | 2/2010 |
| JP | 04459013 | B2 | 2/2010 |
| JP | 2010022560 | | 2/2010 |
| JP | 04481325 | B2 | 3/2010 |
| JP | 2010046155 | | 3/2010 |
| JP | 2010051654 | A | 3/2010 |
| JP | 2010063814 | A | 3/2010 |
| JP | 2010063944 | A | 3/2010 |
| JP | 04492957 | B2 | 4/2010 |
| JP | 2010068954 | A | 4/2010 |
| JP | 2010075462 | A | 4/2010 |
| JP | 2010082059 | A | 4/2010 |
| JP | 2010104545 | A | 5/2010 |
| JP | 2010104547 | A | 5/2010 |
| JP | 2010110535 | A | 5/2010 |
| JP | 2010119454 | A | 6/2010 |
| JP | 2010119605 | A | 6/2010 |
| JP | 2010119743 | A | 6/2010 |
| JP | 2010131131 | A | 6/2010 |
| JP | 2010131132 | A | 6/2010 |
| JP | 2010131206 | | 6/2010 |
| JP | 2010131297 | A | 6/2010 |

(56) References Cited

FOREIGN PATENT DOCUMENTS

| | | | |
|---|---|---|---|
| JP | 2010136917 | A | 6/2010 |
| JP | 2010136973 | A | 6/2010 |
| JP | 04540563 | B2 | 7/2010 |
| JP | 04587947 | B2 | 9/2010 |
| JP | 2010194124 | A | 9/2010 |
| JP | 2010194218 | | 9/2010 |
| JP | 2010201093 | | 9/2010 |
| JP | 2010221067 | | 10/2010 |
| JP | 4577766 | B2 | 11/2010 |
| JP | 04620299 | B2 | 11/2010 |
| JP | 04627472 | B2 | 11/2010 |
| JP | 04627473 | B2 | 11/2010 |
| JP | 04638087 | B2 | 12/2010 |
| JP | 04652626 | B2 | 12/2010 |
| JP | 2010273842 | A | 12/2010 |
| JP | 2010284418 | A | 12/2010 |
| JP | 2011000480 | A | 1/2011 |
| JP | 2011030700 | | 2/2011 |
| JP | 04693574 | B2 | 3/2011 |
| JP | 2011067484 | A | 4/2011 |
| JP | 2011072720 | A | 4/2011 |
| JP | 2011104014 | | 6/2011 |
| JP | 2011104122 | A | 6/2011 |
| JP | 2011120661 | A | 6/2011 |
| JP | 2011125360 | A | 6/2011 |
| JP | 2011125537 | | 6/2011 |
| JP | 04776516 | B2 | 7/2011 |
| JP | 2011130797 | A | 7/2011 |
| JP | 2011130799 | A | 7/2011 |
| JP | 2011156032 | A | 8/2011 |
| JP | 2011156070 | A | 8/2011 |
| JP | 2011156254 | | 8/2011 |
| JP | 04824882 | B2 | 9/2011 |
| JP | 4850272 | B2 | 10/2011 |
| JP | 04855533 | B2 | 11/2011 |
| JP | 2011239858 | | 12/2011 |
| JP | 2011240050 | | 12/2011 |
| JP | 04931572 | B2 | 2/2012 |
| JP | 04937225 | B2 | 3/2012 |
| JP | 04953618 | B2 | 3/2012 |
| JP | 04969437 | B2 | 4/2012 |
| JP | 04969640 | B2 | 4/2012 |
| JP | 4971491 | B2 | 4/2012 |
| JP | 04974524 | B2 | 4/2012 |
| JP | 04979780 | B2 | 4/2012 |
| JP | 05016020 | B2 | 6/2012 |
| JP | 05027364 | B2 | 6/2012 |
| JP | 2012115378 | | 6/2012 |
| JP | 05031082 | B2 | 7/2012 |
| JP | 05042351 | B2 | 7/2012 |
| JP | 05043569 | B2 | 7/2012 |
| JP | 05043591 | B2 | 7/2012 |
| JP | 05046488 | B2 | 7/2012 |
| JP | 2012125452 | | 7/2012 |
| JP | 2012125625 | A | 7/2012 |
| JP | 05053765 | B2 | 8/2012 |
| JP | 05070275 | B2 | 8/2012 |
| JP | 05079931 | B1 | 9/2012 |
| JP | 05080189 | B2 | 9/2012 |
| JP | 05084442 | B2 | 9/2012 |
| JP | 05084476 | B2 | 9/2012 |
| JP | 5085770 | B2 | 9/2012 |
| JP | 05089269 | B2 | 9/2012 |
| JP | 2012179286 | | 9/2012 |
| JP | 05113146 | B2 | 10/2012 |
| JP | 05129536 | B2 | 11/2012 |
| JP | 2012223230 | | 11/2012 |
| JP | 2012223231 | | 11/2012 |
| JP | 05105884 | B2 | 12/2012 |
| JP | 5715806 | B2 | 5/2015 |
| KR | 20010005620 | | 1/2001 |
| KR | 20020035634 | | 5/2002 |
| KR | 20080028771 | | 4/2008 |
| SE | 9400916 | | 3/1994 |
| SE | 9704893 | | 12/1997 |
| WO | WO90/15830 | | 12/1990 |
| WO | WO9219198 | | 11/1992 |
| WO | WO93/21237 | | 10/1993 |
| WO | WO9321879 | | 11/1993 |
| WO | WO9510996 | | 4/1995 |
| WO | WO9511652 | | 5/1995 |
| WO | WO95/16746 | | 6/1995 |
| WO | WO9514453 | | 6/1995 |
| WO | WO9515139 | | 6/1995 |
| WO | WO9516424 | | 6/1995 |
| WO | WO9519753 | | 7/1995 |
| WO | WO95/21596 | | 8/1995 |
| WO | WO95/24173 | | 9/1995 |
| WO | WO9526209 | | 10/1995 |
| WO | WO9529657 | | 11/1995 |
| WO | WO95/34329 | | 12/1995 |
| WO | WO9532698 | | 12/1995 |
| WO | WO9616624 | | 6/1996 |
| WO | WO9619173 | | 6/1996 |
| WO | WO96029967 | | 10/1996 |
| WO | WO9711659 | | 4/1997 |
| WO | WO9717922 | | 5/1997 |
| WO | WO9724096 | | 7/1997 |
| WO | WO9816179 | | 4/1998 |
| WO | WO9816180 | | 4/1998 |
| WO | WO9843684 | | 10/1998 |
| WO | WO9913813 | | 3/1999 |
| WO | WO99/34841 | | 7/1999 |
| WO | WO9951178 | | 10/1999 |
| WO | WO200000235 | | 1/2000 |
| WO | WO200032145 | | 6/2000 |
| WO | WO200059430 | | 10/2000 |
| WO | WO200115647 | | 3/2001 |
| WO | WO200126596 | | 4/2001 |
| WO | WO0135886 | | 5/2001 |
| WO | WO200207663 | | 1/2002 |
| WO | WO200232962 | | 4/2002 |
| WO | WO2002064877 | | 8/2002 |
| WO | WO2002067809 | | 9/2002 |
| WO | WO2003009794 | | 2/2003 |
| WO | WO2003039402 | | 5/2003 |
| WO | WO2003053297 | | 7/2003 |
| WO | WO03079946 | | 10/2003 |
| WO | WO03101622 | | 12/2003 |
| WO | WO2003105738 | | 12/2003 |
| WO | WO2004021946 | | 3/2004 |
| WO | WO2004049995 | | 6/2004 |
| WO | WO2004071539 | | 8/2004 |
| WO | WO2004084784 | | 10/2004 |
| WO | WO2004105664 | | 12/2004 |
| WO | WO2005/018694 | | 3/2005 |
| WO | WO2005087164 | | 9/2005 |
| WO | WO2005/102237 | | 11/2005 |
| WO | WO2006104024 | | 5/2006 |
| WO | WO2006059922 | | 6/2006 |
| WO | WO2006062258 | | 6/2006 |
| WO | WO2006066029 | | 6/2006 |
| WO | WO2006083584 | | 8/2006 |
| WO | WO2006134904 | | 12/2006 |
| WO | WO2006134906 | | 12/2006 |
| WO | WO2007000315 | | 1/2007 |
| WO | WO2007046052 | | 4/2007 |
| WO | WO2007047598 | | 4/2007 |
| WO | WO2007049725 | | 5/2007 |
| WO | WO2007061035 | | 5/2007 |
| WO | WO2007141744 | | 12/2007 |
| WO | WO2007142145 | | 12/2007 |
| WO | WO2007148502 | | 12/2007 |
| WO | WO2008018922 | | 2/2008 |
| WO | WO2008065945 | | 6/2008 |
| WO | WO2008146749 | | 12/2008 |
| WO | WO2008155699 | | 12/2008 |
| WO | WO2009004941 | | 1/2009 |
| WO | WO2009005431 | | 1/2009 |
| WO | WO2009139248 | | 1/2009 |
| WO | WO2009139255 | | 1/2009 |
| WO | WO2009041223 | | 4/2009 |
| WO | WO2009096108 | | 8/2009 |
| WO | WO2009107435 | | 9/2009 |

(56) References Cited

FOREIGN PATENT DOCUMENTS

| | | |
|---|---|---|
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2010118272 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO2012117764 | 9/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170783 | 12/2012 |
| WO | WO2012170808 | 12/2012 |
| WO | WO2012174026 | 12/2012 |
| WO | WO2012177400 | 12/2012 |
| WO | WO2013001788 | 1/2013 |
| WO | WO2013046701 | 4/2013 |
| WO | WO2013056978 | 4/2013 |
| WO | WO2013060733 | 5/2013 |
| WO | WO2013077074 | 5/2013 |
| WO | WO2014073636 | 5/2014 |
| WO | WO2014078247 | 5/2014 |
| WO | WO 2014093310 | 6/2014 |
| WO | 2015094734 A1 | 6/2015 |
| WO | WO2015095514 | 6/2015 |
| WO | WO2016040091 | 3/2016 |

OTHER PUBLICATIONS

Extended European Search Report and Search Opinion; U.S. Appl. No. 16/167,637; dated Jun. 10, 2016; 5 pages.

International Search Report and Written Opinion; Application Ser. No. PCTUS2017/024888; dated Jun. 27, 2017, 8 pages.

* cited by examiner

ABSORBENT CORE WITH PROFILED DISTRIBUTION OF ABSORBENT MATERIAL

FIELD OF THE INVENTION

The invention relates to absorbent cores for use in absorbent articles such as, but not limited to, baby diapers, training pants, feminine pads or adult incontinence products. The invention efficiently uses the absorbent material by improving its placement in the absorbent core.

BACKGROUND OF THE INVENTION

Absorbent articles for personal hygiene of the type indicated above are designed to absorb and contain body exudates, in particular large quantity of urine. These absorbent articles comprise several layers providing different functions, such as a topsheet, a backsheet and in-between an absorbent core, among other layers. The absorbent core should absorb and retain the exudates for a prolonged amount of time in order to keep the wearer dry and avoid soiling of clothes or bed sheets. At the same time, the absorbent core should make the most efficient use possible of the absorbent material to save material costs and keep the diapers as thin as possible.

The majority of currently marketed absorbent articles comprise as absorbent material a blend of cellulose fibers with superabsorbent polymers (SAP) particles, also called absorbent gelling materials (AGM), see for example U.S. Pat. No. 5,151,092 (Buell). Absorbent articles having a core consisting essentially of SAP without cellulose fibers as absorbent material (so called “airfelt-free” cores) have also been proposed. For example WO2008/155699 (Hundorf et al.) discloses absorbent cores with a patterned layer of SAP immobilized by a net of fibrous thermoplastic adhesive material deposited over the layer of SAP. The fibrous thermoplastic material helps maintaining the SAP in position within the absorbent core prior to and during use of the article, without substantially restricting the ability of the SAP to absorb large volumes of urine. More recently, WO2012/170783 (Hundorf et al.) discloses absorbent cores comprising absorbent material having a basis weight that varies across the absorbent core. WO2012/170778 (Rosati et al., see also WO2012/170779, WO2012/170781 and WO2012/170808) discloses absorbent structures that comprise superabsorbent polymers, optionally a cellulosic material, and at least a pair of substantially longitudinally-extending channels. The core wrap can be adhesively bonded through the channels to form a channel bond. The integrity of the channel bonds may be at least partially maintained in wet state.

While the absorbent cores of the prior art generally have good properties, there is a continuous need to improve comfort, fit and efficiency of the current cores and to reduce the usage of raw material, in particular the superabsorbent particles, while improving or at least maintaining key properties such as the speed of acquisition and retention of the fluid. The present invention addresses all these problems.

SUMMARY OF THE INVENTION

The invention is directed to absorbent cores and absorbent articles containing these absorbent cores as indicated in the claims. The absorbent core of the invention extends in a longitudinal direction parallel to a longitudinal axis and a transversal direction perpendicular to the longitudinal direction. In a first aspect, the absorbent core comprises:

- a core wrap having a top side and a bottom side;
- an absorbent material between the top side and bottom side of the core wrap;
- a first and second longitudinally-extending channel-forming areas substantially free of absorbent material, preferably through which the top side of the core wrap is attached to the bottom side of the core wrap, and wherein the first channel-forming area is disposed on one side of the longitudinal axis and the second channel-forming area on the other side of the longitudinal axis;
- a central absorbent zone comprising absorbent material and disposed between the first and the second channel-forming areas; and
- a first lateral absorbent zone and a second lateral absorbent zone comprising absorbent material and disposed laterally outwardly of the first and second channel-forming areas respectively.

The basis weight of the absorbent material in the central absorbent zone is higher than the basis weight of the absorbent material in each of the lateral absorbent zones for at least a first transversal section of the core having a first length in the longitudinal direction of at least 10 mm; and inversely in a second transversal section of the core having a second length in the longitudinal direction of at least 10 min, the basis weight of the absorbent material in the central absorbent zone is lower than the basis weight of the absorbent material in the lateral zones. The first and second channel-forming areas may be at least partially curved or angled so that the width of the central absorbent zone vary at least along a portion of the length of the core. Alternatively the first and second channel-forming areas may be straight and oriented parallel to the longitudinal axis. This and further aspects will now be further described in the following description.

DETAILED DESCRIPTION OF THE INVENTION

General Description of the Absorbent Core 28

As used herein, the term "absorbent core" or "core" refers to a component which is placed or is intended to be placed within an absorbent article, and which comprises an absorbent material contained in a core wrap. As used herein, the term "absorbent core" does not include the topsheet, the backsheet and (if present) an acquisition layer, a distribution layer or an acquisition-distribution multilayer system which is not integral part of the absorbent core. The absorbent core has typically the most absorbent capacity of all the components of the absorbent article, and comprises all or at least the majority of superabsorbent polymer (SAP). The core typically thus consists essentially of, or consists of, the core wrap, the absorbent material and optionally adhesives. The absorbent material may consist of SAP in particulate form as exemplified in the present description but it is not excluded that other absorbent materials may be used. The terms "absorbent core" and "core" are herein used interchangeably.

Figure 1:
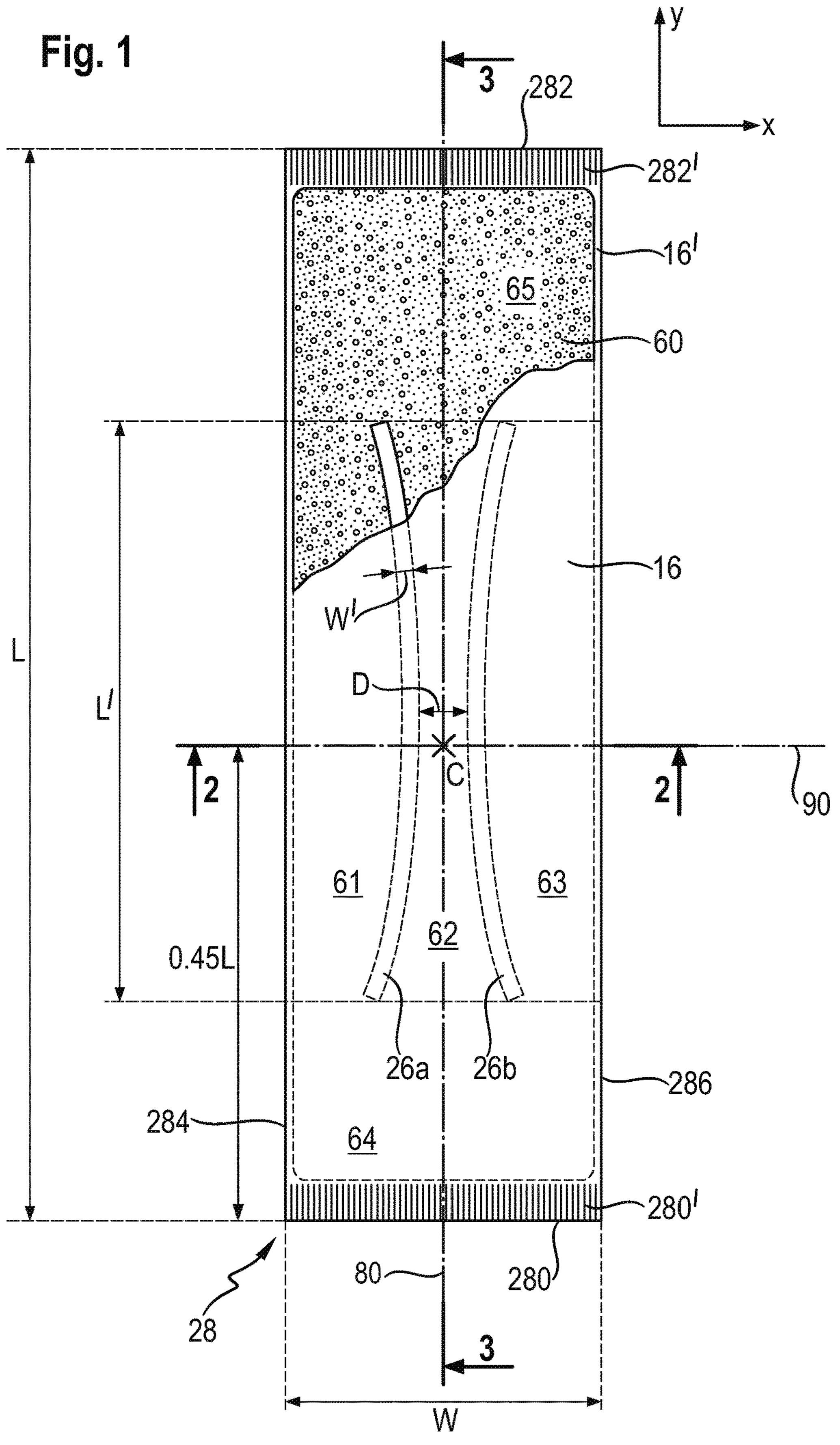
FIG. 1 is a top view of an absorbent core comprising two curved channel-forming areas, with the top layer of the core wrap partially removed.

The absorbent core may be substantially planar so that it can be laid flat on a surface. The absorbent core may also be typically thin and conformable, so that it can also be laid on a curved surface for example a drum during its making process or stored as a continuous roll of stock material before being converted into an absorbent article. FIGS. 1-4 schematically show an absorbent core as known from the prior art, e.g. as in WO2012/170,778. The absorbent cores of the invention may comprise the same basic features as the absorbent core of FIGS. 1-4. For ease of discussion, the exemplarily absorbent core of FIG. 1 is represented in a flat state and extending in a plane along a transversal direction (x) and a longitudinal direction (y). Unless otherwise indicated, dimensions and areas disclosed herein apply to the core in this flat-out configuration. The same applies to an absorbent article, as exemplarily represented in FIG. 9, in which the core can be integrated. For ease of discussion, the absorbent cores and articles of the invention will be discussed with reference to the Figures and the numerals referred to in these Figures, however these are not intended to limit the scope of the claims unless specifically indicated.

The outline of the absorbent core is typically defined by the core wrap. The core wrap may comprise two individual substrates 16, 16' as exemplified in the FIGS. 1-4, but it is also common and possible to have a single substrate forming the core wrap. The absorbent core typically comprises a front edge 280, a back edge 282 and two longitudinally-extending side edges 284, 286 joining the front edge and the back edge. The front edge is the edge of the core intended to be placed towards the front edge 10 of the absorbent article in which the core is or will be integrated. Typically the absorbent material 60 of the core may be advantageously distributed in somewhat higher amount towards the front edge than towards the back edge as more absorbency is typically required towards the front half of the article. Typically the front and back edges 280, 282 may be shorter than the longitudinally-extending side edges 284, 286. The absorbent core also comprises a top side 288 and a bottom side 290. The top side of the core is the side placed or intended to be placed towards the topsheet 24 of the article and the bottom side is the side placed or intended to be placed towards the backsheet 25 in the finished article. The top side of the core wrap may be typically treated to be more hydrophilic than the bottom side.

The absorbent core can notionally (i.e. virtually) comprise a longitudinal axis 80 extending from the front edge 280 to the back edge 282 and dividing the core in two substantially symmetrical halves relative to this axis, when viewing the core in the plane formed by the longitudinal and transversal direction (x, y). The absorbent core can typically be generally rectangular with a width W in the transversal direction and a length L in the longitudinal direction as measured from edge to edge, including the region of the core wrap which does not enclose the absorbent material, in particular at the front and back end seals 280', 282' when present. In case the core is not rectangular, the maximum dimension measured along the transversal direction and the longitudinal direction can be used to report the width and length of the core respectively. The width and length of the core may vary depending on the intended usage. For baby and infant diapers, the width W may for example in the range from 40 mm to 200 mm and the length L from 100 mm to 600 mm. Adult incontinence products may have higher maximum dimensions.

The transversal axis 90 of the core (also referred to as "crotch line") is defined as the virtual line perpendicular to the longitudinal axis 80 and bisecting the core at a distance of 0.45 of L from the front edge 280 of the absorbent core, L being the length of the core as measured from the front edge 280 in direction of the back edge 282, as shown on FIG. 1. The crotch point C is herein defined as the point of intersection of these two axis. The crotch region of the core is defined herein as the region of the core extending from the transversal axis 90, i.e. at the level of the crotch point C, towards the back edge and front edge of the core by a distance of a quarter of L (L/4) in both directions for a total length of L/2. The front region and back region of the core are the remaining regions of the core towards the front and back edges of the core respectively.

The absorbent material 60 may be any conventional absorbent material used in absorbent articles. In the examples provided further below, the absorbent material consists of SAP particles immobilized by an adhesive, but it is not excluded that any other types of absorbent material may be used, for example superabsorbent foam or a cellulose fibers/SAP mix. The absorbent core may thus be relatively thin, in particular thinner than conventional cores comprising cellulosic fibers. In particular, the caliper of the core (dry, i.e. before use) as measured at the crotch point (C) or at any other points of the surface of the core according to the Dry Core Caliper Test as described herein may be from 0.25 mm to 5.0 mm, in particular from 0.5 mm to 4.0 mm.

Figure 3:
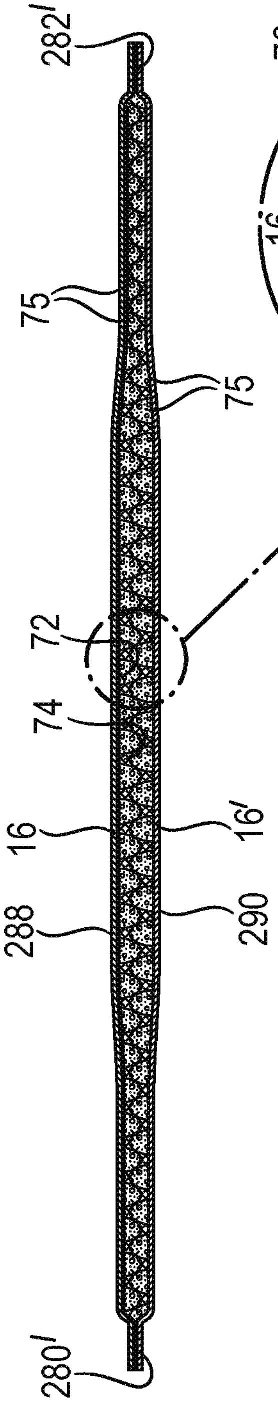
FIG. 3 is a schematic longitudinal cross-section of the core showing an optional dual absorbent layer construction.
Figure 4:
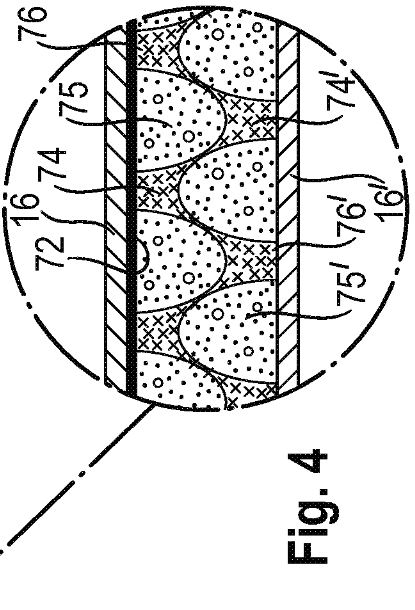
FIG. 4 is a schematic close-up view of a section of FIG. 3.

The absorbent material 60 may be deposited within the core wrap as one layer, or as represented in FIGS. 3-4 as two absorbent layers applied on the top substrate 16 and bottom substrate 16' respectively in a pattern of land areas 75,75' separated by junction areas 76,76', for example as generally disclosed in WO2008/155699. In particular, two absorbent layers having offset land 75,75' and junction areas 76, 76' may be combined to form an absorbent material deposition area in which the absorbent material is substantially continuous, as shown in FIG. 1. This dual layer printing process will be discussed further below with reference to the process illustrated in FIG. 12. If the absorbent core is made according to this process, it may further advantageously comprise a fibrous thermoplastic adhesive 74, 74' to further immobilize the absorbent material. However the absorbent cores of the present invention are not limited to a particular process for making them. As illustrated in FIG. 3, the absorbent core may have a profiled distribution of material in the longitudinal direction, especially having a higher basis weight in the crotch region than in the front region, and still higher in the front region than in the back region.

Figure 2:
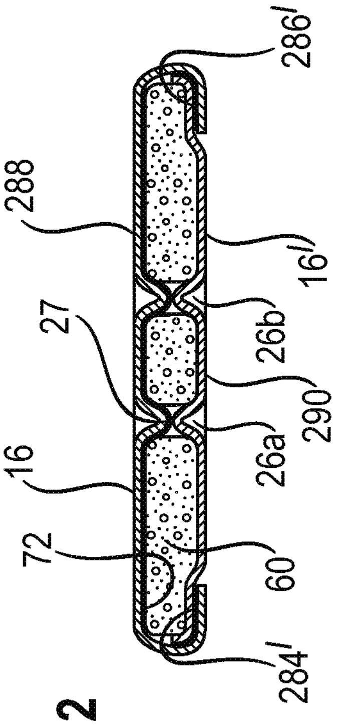
FIG. 2 is a schematic transversal cross-section of the core of FIG. 1.

The absorbent material 60 defines an absorbent material deposition area as seen from above within the plane of the core. The deposition area may be generally rectangular as shown in the FIG. 1, or may be shaped so that it has a tapered section in the crotch region, as is known in the art in so-called shaped cores. The absorbent core comprises within the deposition area at least a first and a second longitudinally-extending channel-forming areas 26*a*, 26*b* disposed on opposite sides of the longitudinal axis 80. The channel-forming areas may be typically mirror image of each other relative to the longitudinal axis. The top side 288 of the core wrap is preferably bonded to the bottom side 290 of the core wrap through these channel-forming areas 26 which are substantially free of absorbent material. The channel bonds 27 are typically encompassed within the areas substantially free of absorbent material. The bond 27 between the substrates 16, 16' in the channel-forming areas 26 may be provided by an auxiliary glue 72 applied directly to the inner surface of at least one of the substrate, as illustrated in FIG. 2, and/or by any other bonding means such as fusion bonding or ultrasonic bonding. Typically the bonds 27 may generally have the same outline and shape as the absorbent material free areas 26 in which they are contained, but may be slightly smaller to allow for a safety margin (e.g. by a few mm) as some deviations from the optimal registration may happen during high speed process. It is however not excluded that the channel bonds 27 may be provided in areas containing absorbent material, in those cases the bonds may however be substantially less strong and more easily delaminate when the absorbent material swells.

The two channel-forming areas 26*a,b* define a central absorbent zone 62 disposed between them, and a first and second lateral absorbent zones 61, 63 respectively disposed laterally outwardly of the first and second channel-forming areas. The central, first and second lateral absorbent zones comprise absorbent material. The first and second lateral absorbent zones typically extend laterally up to the longitudinal side edges 284, 286 of the absorbent core. As defined herein, the central absorbent zone 62 and the lateral absorbent zones 61, 63 do not extend beyond the longitudinal extremities of the channel-forming areas 26, and thus the central and the lateral zones typically all have the same length L' as the length of the channel-forming areas 26. The rest of the absorbent core comprising absorbent material may thus define a front absorbent zone 64 extending longitudinally forward of the front extremities of the channel-forming areas and up to the front end seal 280' and a back absorbent zone 65 extending longitudinally backward from the back extremities of the channel-forming areas to the back end seal 282' of the core.

Figure 9:
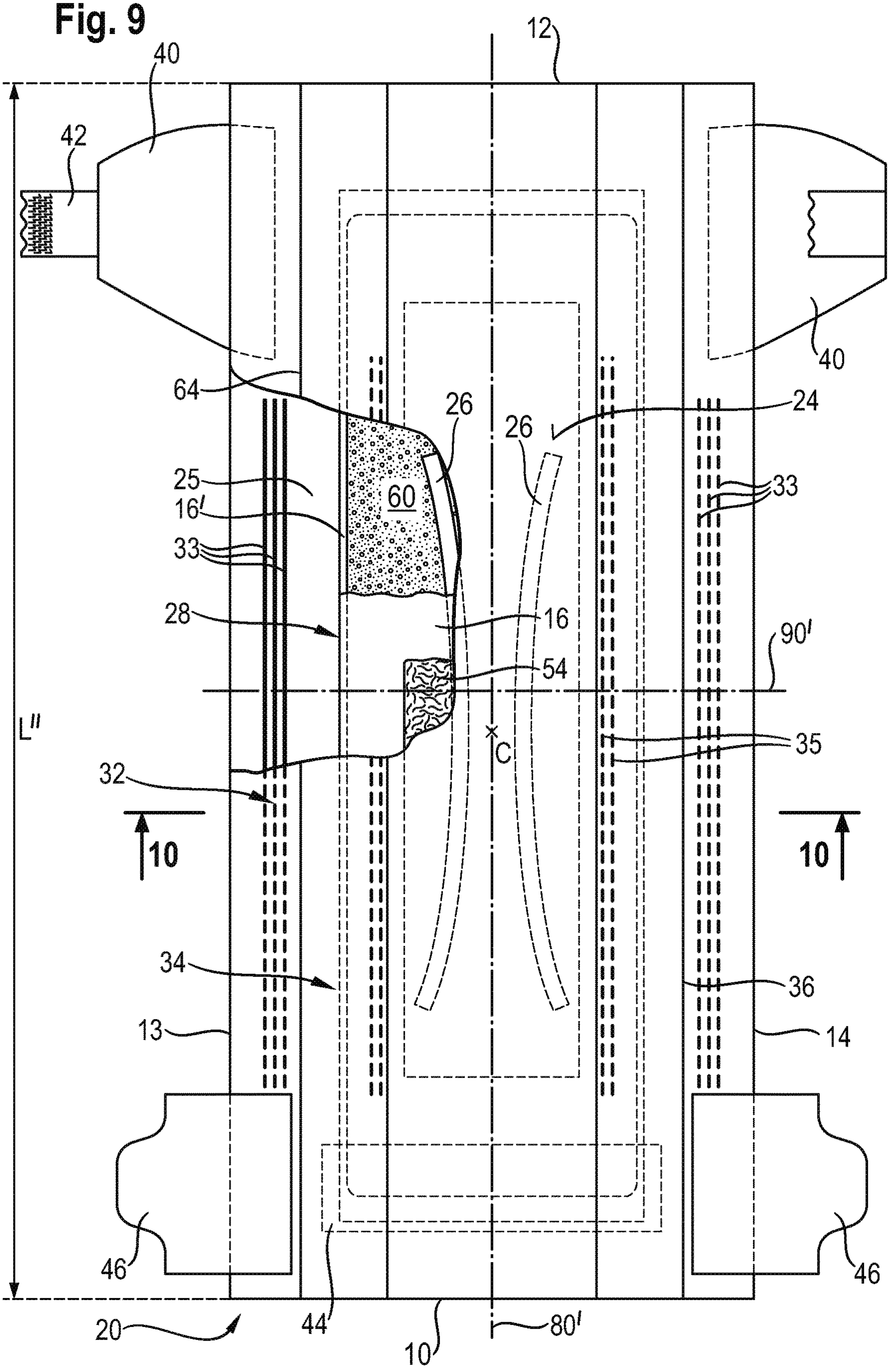
FIG. 9 is a top view of an exemplary taped diaper comprising an absorbent core of the invention with some layers partially removed.
Figure 11:
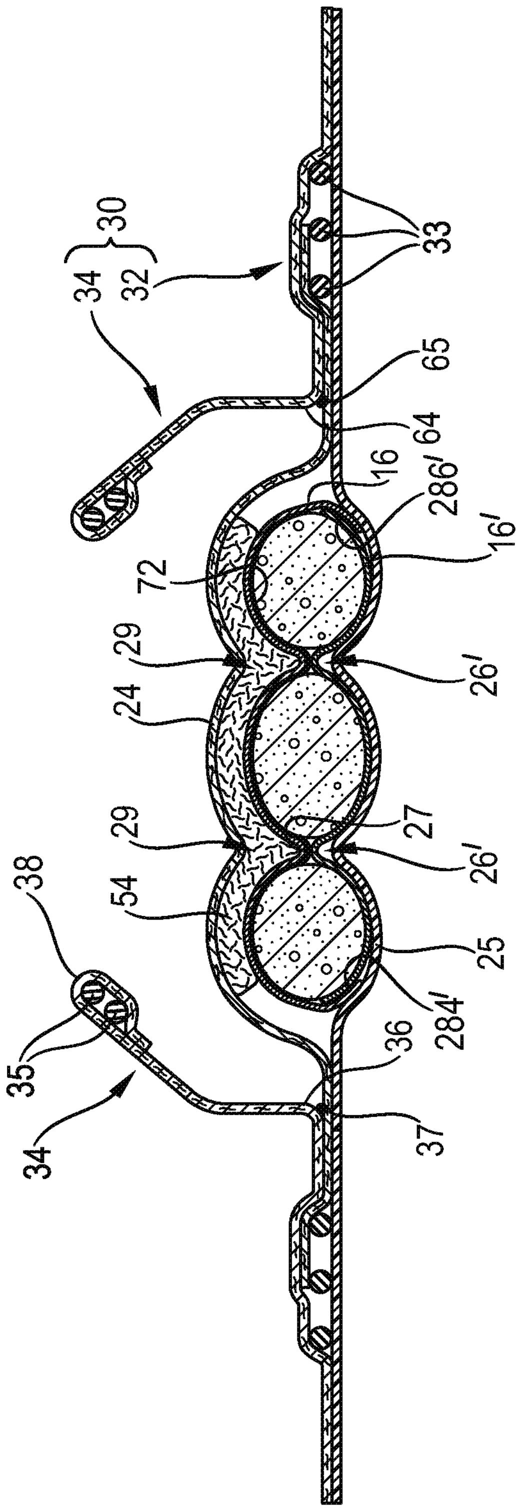
FIG. 11 shows a transversal cross-section as in FIG. 10 wherein the absorbent core has swollen after absorbing a fluid.

The absorbent cores of the invention will typically be used in an absorbent article 20, for example a taped diaper as shown on FIG. 9 in a flat-out state. The longitudinal axis 80 of the core may be superposed with the longitudinal axis 80' of the article. The absorbent article 20 typically comprises a liquid permeable topsheet 24 on the wearer-facing side of the article, a liquid impermeable backsheet 25 on the opposite, garment-facing side of the article, with the absorbent core 28 positioned between the topsheet and the backsheet. As the absorbent material 60 swells when it absorbs a liquid such as urine, the bond 27 in the channel-forming areas 26 remain at least initially in place between the top and bottom sides of the core wrap, so that the channel-forming areas 26 form three-dimensional channels 26' as illustrated in FIG. 11. An acquisition layer and/or a distribution layer 54 disposed above the absorbent core 28 may be deformed and form ditches 29 corresponding to the underlying three-dimensional channels 26'. The acquisition or distribution layer may also comprise channel areas free of acquisition/distribution material at least partially superposed to the channel-forming areas (as taught for example by Roe et al. in WO2015/31225, WO2015/31229, WO2015/31243 or WO2015/31256).

Absorbent Material Distribution

After having disclosed the general construction of an exemplary absorbent core in FIGS. 1-4, the improved distribution of absorbent material in the absorbent cores of the invention will be further generally described below, and by way of non-limiting illustrations with the embodiments shown in the FIGS. 5-8 and 14-15. Unless indicated otherwise, the features of the examples are not limiting the scope of the invention.

Figure 5:
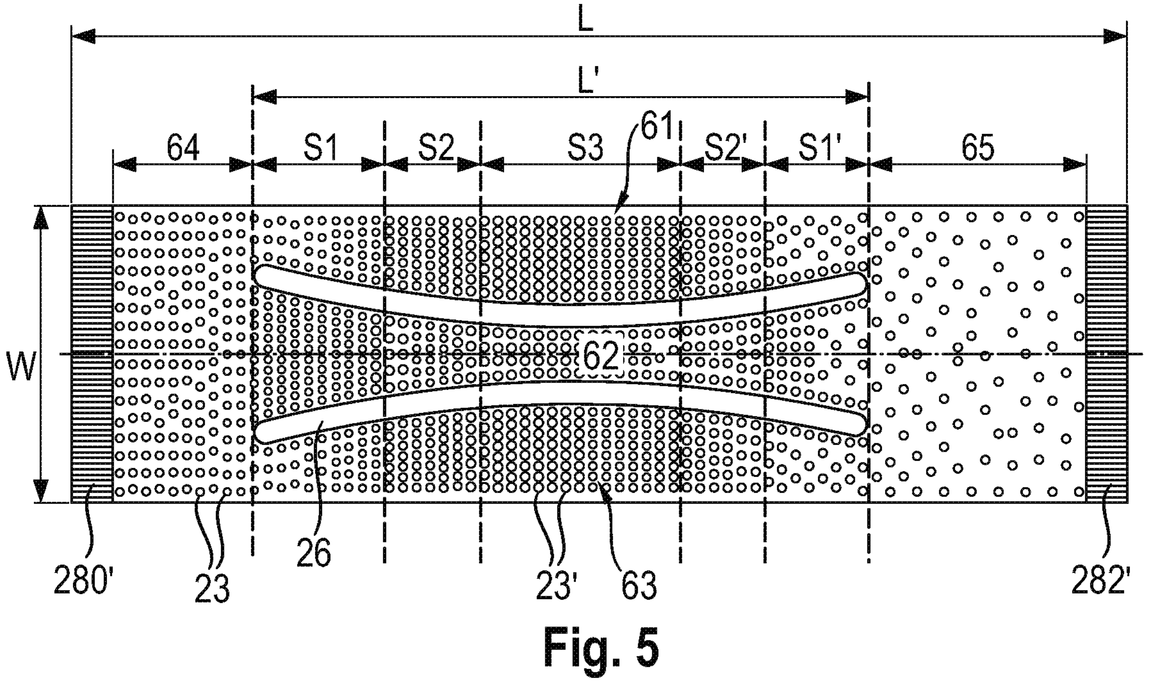
FIG. 5 shows an exemplary deposition pattern of SAP particles to provide a distribution of absorbent material according to the invention.
Figure 6:
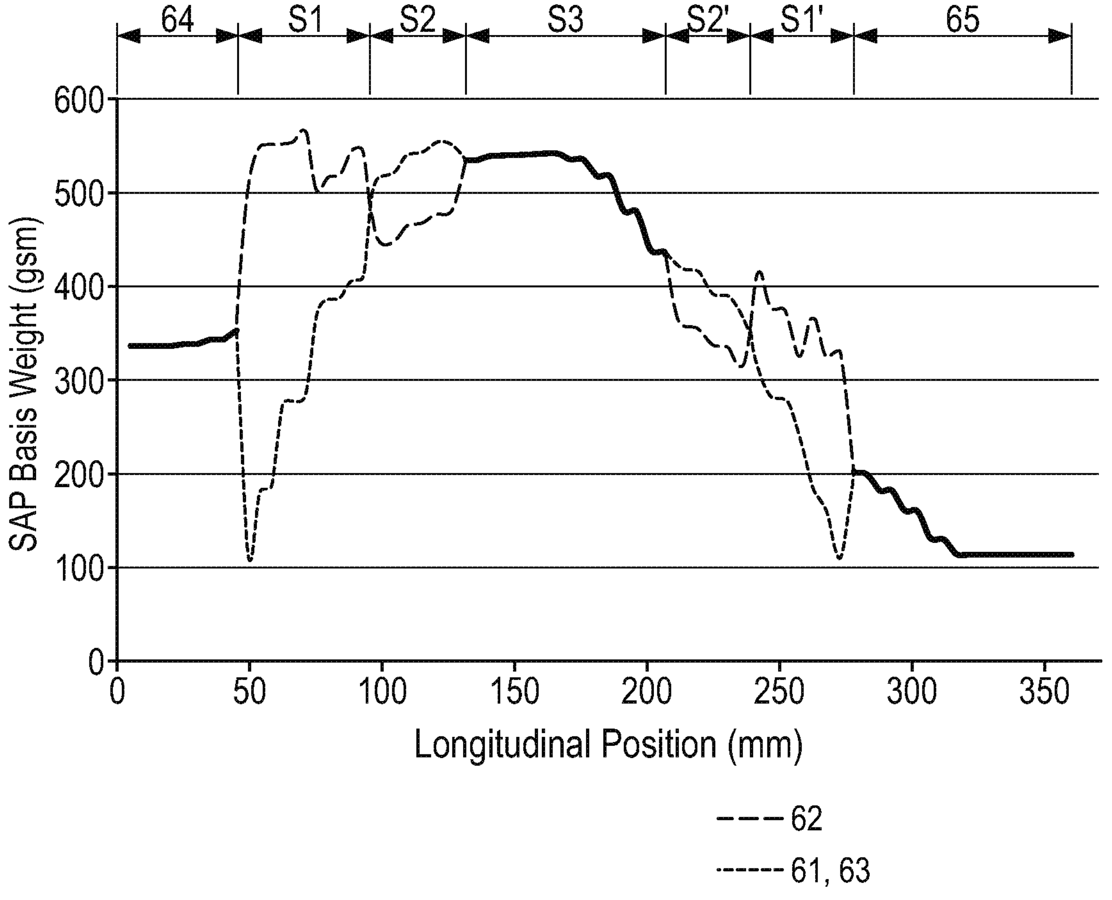
FIG. 6 shows the relation between the basis weight of the absorbent material and the position along the longitudinal axis in the core of FIG. 5.

FIGS. 5-6 disclose a first example of absorbent material distribution according to the invention. FIG. 5 shows a schematic top view of the absorbent core with the absorbent material distribution represented by the dots 23, 23'. Each of the dots 23, 23' represents a small quantity of SAP particles, which taken together make up the absorbent material 60 of the core. The amount and distribution of SAP in the absorbent core may be represented by the position and size of these dots, wherein the larger dots 23' represent larger amount of SAP and the smaller dots 23 lower amount. The distance between two dots may also be varied to influence the amount of SAP particles deposited. The larger and closer the dots are to each other, the higher the basis weight of the absorbent material will be in the area considered. The resulting basis weight distribution in the different absorbent zones is illustrated in the diagram of FIG. 6.

Figure 7:
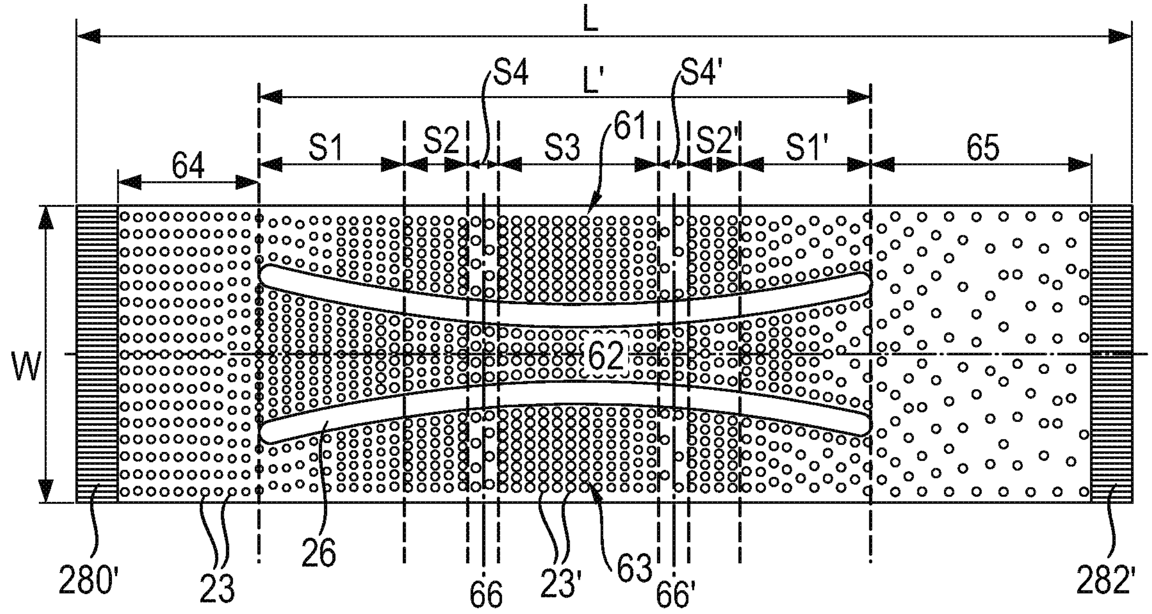
FIG. 7 shows another exemplary deposition pattern of SAP particles according to the invention.

The SAP particles are represented in FIG. 5 and FIG. 7 by dots 23 aligned in the transversal direction as this may reflect a non-limiting SAP printing process for depositing the SAP particles onto two substrates forming respectively the top and bottom side of the core wrap. This process is e.g. generally taught in Hundorf's WO2010/027719A2, which will be discussed further below in greater details with reference to the apparatus and process of FIGS. 12-13. It should however be understood that according to this process, directly after the dots of SAP particles are deposited on the substrate on the lay-on drum, the particles will spread to a larger area and form generally continuous land areas 75 separated by junction areas 76 for each absorbent layer. For example if the lay-on drum has transversally oriented bars 36 between which the substrate is depressed, the dots in each transversal depressions will merge to form transversally oriented land areas. Typically, each substrate 16, 16' may be printed with about half of the SAP dots. The substrates 16, 16' are then assembled in face-to-face relation with the respective land areas 75, 75' of each substrate being offset relative to each other so that the absorbent material form a substantially continuous absorbent area as illustrated in FIGS. 1-4.

Thus while the views of FIG. 5 and FIG. 7 with the discrete SAP dots are illustrative of one way to provide the claimed distribution of SAP particles, the resulting absorbent material deposition area may be typically substantially continuous in the area of the core comprising the absorbent material. Thus, typically, no individual dots 23 are recognizable in the finished core, except possibly in areas of low basis weight such as in the back absorbent zone 65 towards the back edge seal 282' where the dots may be deposited too far away from each other to merge into larger land areas 75. FIGS. 5, 7 are thus to be understood as an useful illustration of how the basis weight of the absorbent material may be varied in the different absorbent zones of the absorbent core to achieve an absorbent material distribution of the present invention. However these should not be considered in any way limiting the scope of the invention, as other processes may be used to make the absorbent core of the invention.

FIG. 6 shows the basis weight distribution in the different absorbent zones corresponding to the SAP deposition pattern shown in FIG. 5. The longitudinal position is indicated in mm on the horizontal axis and refers to the distance from the front edge of the absorbent core (disregarding the length of the front seal 280' which is substantially free of absorbent material). The absorbent material basis weight corresponding to the different longitudinal positions for each absorbent zone is indicated on the vertical axis. In short, starting from the front end seal 280', the front absorbent zone 64 which is disposed forward of the channel-forming areas has a basis weight that first slightly increases (in this example from about 340 g/m$^2$ (grams per square meter, or gsm) to about 360 g/m$^2$ for the first front 45 mm of the absorbent area of the core). The channel-forming areas 26 then start, and the absorbent material is present in the central absorbent zone 62 and the lateral absorbent zones 61, 63 at different basis weight in the sections S1 and S2. A third section S3 is provided in this example where the basis weight is about the same in the central and lateral zones. Two sections S1' and S2' are then provided where the basis weight relation between the central absorbent zone and lateral absorbent zones differs, until the end of the channel-forming areas. The back absorbent zone 65 of the core has a relatively low basis weight that gradually decreases to a minimum until the back end seal 282' is attained.

In the first transversal section S1 of the core, the basis weight of the absorbent material in the central absorbent zone 62 is higher than the basis weight of the absorbent material in each of the lateral absorbent zones 61, 63. The minimum value for the basis weight of each of the lateral zones is in this example about 100 g/m$^2$, and the maximum value for the basis weight of the central absorbent zone being about 560 g/m$^2$ (the difference between the maximum value and the minimum value thus being about 460 g/m$^2$). The length in the longitudinal direction of this first section S1 is about 60 mm in this example.

More generally, the first transversal section(s) S1 may have a first length in the longitudinal direction of at least 10 mm, in particular at least 15 mm, or at least 20 mm, or at least 25 mm, or at least 30 mm or more. Furthermore, the basis weight difference between the maximum basis weight value in the central absorbent zone and the minimum basis weight value in (any of) the lateral absorbent zones in the first transversal section(s) may be of at least 20 g/m$^2$, in particular of at least 30 g/m$^2$, or at least 40 g/m$^2$ or at least 50 g/m$^2$, or at least 100 g/m$^2$.

The second transversal section S2 of the absorbent core is in the example of FIGS. 5-6 directly adjacent the first transversal section S1. In the second transversal section, the basis weight of the absorbent material in the central absorbent zone is lower than the basis weight of the absorbent material in (each of) the lateral absorbent zones. The maximum value for the basis weight of each of the lateral zones is in this example about 550 g/m$^2$, and the minimum value for the basis weight of the central absorbent zone being about 440 g/m$^2$ (the difference between the maximum value and the minimum value thus being about 110 g/m$^2$). The length (in the longitudinal direction) of this second transversal section S2 is about 40 mm.

More generally, the second transversal section(s) S2 may have a length of at least 10 mm, in particular at least 15 mm, or at least 20 mm, or at least 25 mm, or at least 30 mm or more. Furthermore, the basis weight difference between the maximum basis weight value in the lateral absorbent zones and the minimum basis weight value in the central absorbent zone in the second transversal section(s) may be of at least 10 g/m$^2$, in particular of at least 20 g/m$^2$, or at least 30 g/m$^2$ or at least 40 g/m$^2$, or at least 50 g/m$^2$.

When, as in this example, the channel-forming areas 26 are concavely curved towards the longitudinal axis 80 when see from above, as in inverted brackets) (the width of the central absorbent zone 62 progressively narrows from the extremities of the channel-forming areas towards their middle, and, inversely, the width of the lateral absorbent zones 61, 63 increases until the channel-forming areas reach a minimum distance. Thus, the ratio of the width of the central absorbent zone to the width of each of the lateral absorbent zones may be higher in the first transversal section S1 than in the second transversal section S2 for the whole or at least a portion of these sections.

By varying the relative basis weight of the absorbent material across different transversal sections in the areas of the channel-forming areas, different effects can be obtained. First the absorbent material can be placed in the regions where most of the fluid will enter the absorbent core, that is typically along the central absorbent zone and in the crotch region of the core. Thus the placement of the absorbent material can be optimized by reducing the relative amount of the absorbent material in the lateral absorbent zones towards the front and back of the crotch region (corresponding to the sections S1 and S1' in the Figures).

Second, it was also found that when the channel-forming areas are curved (or more generally at least partially non-straight, such as angled relative to the longitudinal axis), the volume available for the absorbent material to swell varies disproportionally according the position of the absorbent zone on the longitudinal axis. This is because when the absorbent material swells, the absorbent zones will generally each form an approximate cylinder delimited by the core wrap. When the width of any of the absorbent zone varies by a factor of x, the volume available for the swollen absorbent material varies by a factor of the square of x. Thus, a much higher basis weight of absorbent material may be disposed in the portion of the absorbent zones having a larger width relative to the portion having a smaller width. Arranging the distribution of the absorbent material differently for the central absorbent zone and the lateral absorbent zones at different longitudinal positions thus allows to manage the fluid constraint inside the absorbent zones in an optimized way. This may in particular help avoiding that the absorbent zones become too stiff in the longitudinal direction in certain areas, while still keeping enough stiffness so that the absorbent core refrains from excessive sagging in the crotch region when wet. Excessive sagging may for example cause the barrier leg cuffs or the gasketing cuffs to lose contact with the skin of the users, thus raising the risk of side leakage outside of the article, and should be avoided.

Figure 14:
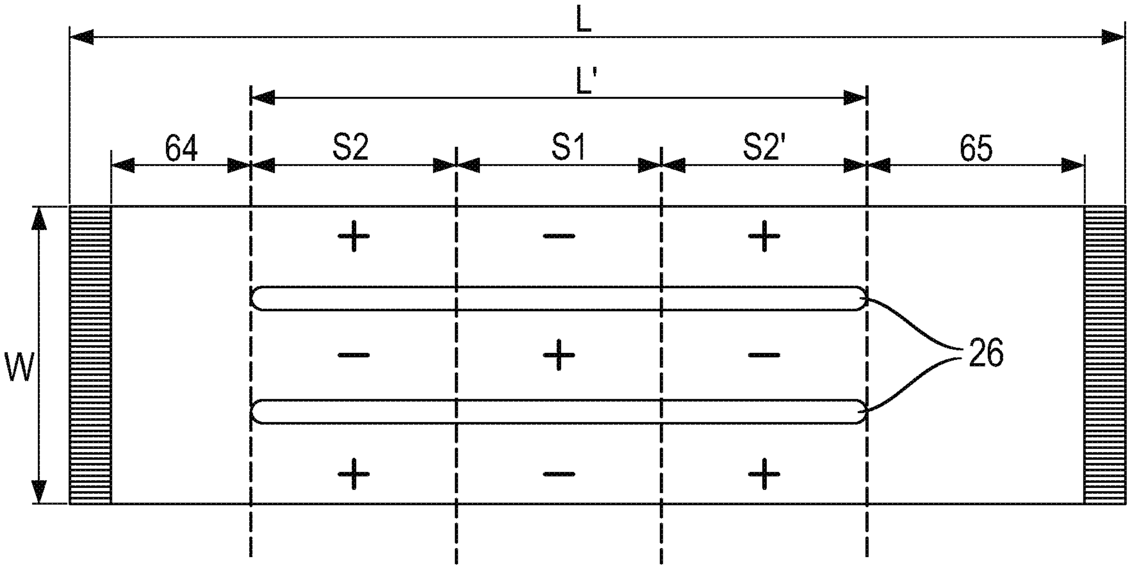
FIG. 14 shows an alternative distribution pattern for the SAP wherein the channel-forming areas are straight.
Figure 15:
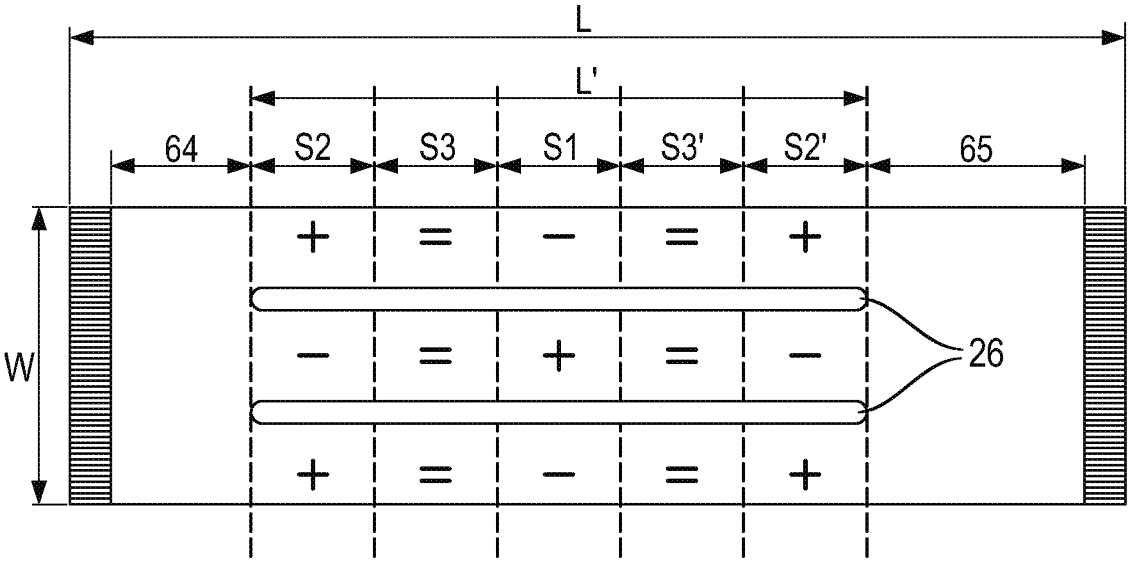
FIG. 15 shows an alternative distribution pattern for the SAP wherein the channel-forming areas are straight.

Alternatively, and as illustrated in FIGS. 14-15, the channel-forming areas may be straight, and in particular longitudinally oriented parallel to the longitudinal axis 80. In FIG. 14 and in FIG. 15, the zones of the absorbent core indicated with a plus "+" sign have a higher basis weight than the corresponding zones at the same position on the longitudinal axis which are marked with a minus "−" sign. Having a distribution of SAP according to the invention is also useful when the channel-forming areas 26 are straight and parallel to the longitudinal axis to provide zones in the absorbent core having different rigidities when the core has absorbed a fluid. Thus, as for the previously described examples, the absorbent core comprises at least one first transversal section S1 wherein the basis weight of the absorbent material in the central absorbent zone is higher than the basis weight of the absorbent material in the lateral absorbent zones, and at least one second transversal section S2, S2' wherein the basis weight of the absorbent material in the central absorbent zone is lower than the basis weight of the absorbent material in the lateral zones. However the relative longitudinal position of these sections may be different than in the previously described examples. The absorbent core may also have, as discussed before, a third type of transversal section S3 where the basis weight is about equal in the central and the lateral absorbent zones. Having such a distribution of SAP allows to provide an improved fit, or better flexibility or other improved characteristics. For example, by reducing the basis weight of the absorbent material in the lateral zones towards the middle of the crotch as illustrated in FIGS. 14 and 15, a more flexible crotch portion in the absorbent core is provided in this area. The absorbent article may be thus more comfortable because the lateral zones will absorb less fluid and thus be less rigid and more conformable as the thighs of the wearer press them. At the same time, having a higher basis weight in the lateral zones towards the front and the back of the absorbent core allows to maintain a good rigidity of the core in these areas (after fluid insult), and thus a better overall fit with the less sagging. FIGS. 14-15 are of course only exemplary, as other distributions of the SAP are possible within the scope of the invention.

Within the invention, various deposition patterns for the absorbent material may be executed. In the example of FIG. 5, a third transversal section S3 is provided in the crotch region of the absorbent core wherein the basis weight in the central and the lateral absorbent zones is about equal. The width of the absorbent zones in this third section leaves enough space for the absorbent material to swell without excessive constraint, even at the relatively have basis weight values in this example varying between about 400 g/m$^2$ and 550 g/m$^2$. In this example, the third section has a length of about 80 mm.

The absorbent cores of the invention, as illustrated in FIG. 5, may further comprise another second transversal section S2' wherein the basis weight in the lateral absorbent zones is higher than in the central absorbent zone, and another first transversal section S1' wherein the basis weight in the central absorbent zone 62 is higher than in the lateral absorbent zones 61,63. The length and basis weight differences in these zones may be as indicated before.

The remaining absorbent material is disposed beyond the back extremities of the channel-forming areas 26 in a back absorbent zone 65. The basis weight in the back absorbent zone 65 may be relatively low, for example below about 200 g/m$^2$. The rest of the absorbent core beyond the back absorbent zone 65 may be free of absorbent material, and a back end seal 282' may be formed therein, if such a seal is desired.

The numerical values indicated above with reference to FIG. 6 are exemplary of a core that may be used in a taped diaper or training pant for young children having a weight range of 8-15 kg, and comprise enough SAP to provide overnight dryness. In this example, the total amount of SAP in the core may be about 12 g, distributed as follows: 11.5% in the front absorbent zone, 28% in the central absorbent zone, 25% in each lateral absorbent zone, and 10.5% in the back absorbent zone (for a total of 100%). More generally, the amount of absorbent material may be for example distributed as indicated in the following Table, the percentage being reported by total weight of the absorbent material in the absorbent core:

| | Range in weight % | In particular |
|---|---|---|
| Front absorbent zone 64 | 0*-25 | 5-20 |
| Central absorbent zone 62 | 15-55 | 20-45 |
| Lateral absorbent zone 61, 63 (each) | 10-40 | 15-30 |
| Back absorbent zone 65 | 0*-25 | 5-15 |

*although not preferred, it is possible that the channel-forming areas extend up to the front and back edges of the absorbent core, so that the front and/or the back absorbent zones are not existent.

Of course, the lengths of the different zones, the total amount of absorbent material and the basis weight distribution will be adapted for the intended usages of the different absorbent articles. Keeping for example sake the same general absorbent material distribution as shown in FIGS. 5-6, the different absorbent zones may have the following non-limiting ranges of lengths and minimum and maximum basis weight, with the lowest values adapted for smaller sizes of diapers and the larger values adapted for larger sizes of absorbent diapers.

| Zones | Range length (mm) | Min/Max basis weight (g/m$^2$) |
|---|---|---|
| Front absorbent zone 64 | 42-62 | 200-400 |
| S1 | 35-70 | 50-500 (Zones 61, 63)<br>300-600 (Zone 62) |
| S2 | 20-40 | 300-600 (Zones 61, 63)<br>250-550 (Zone 62) |
| S3 | 55-105 | 300-650 (Zones 61, 63)<br>300-650 (Zone 62) |
| S2' | 15-35 | 200-450 (Zones 61, 63)<br>150-400 (Zone 62) |
| S1' | 20-45 | 50-400 (Zones 61, 63)<br>150-450 (Zone 62) |
| Back absorbent zone 65 | 81-134 | 50-250 |

The curved channel-forming areas may also be convexly curved, as in two brackets facing away ( ) instead of concavely curved as in two brackets facing each other) (so that the central absorbent zone is wider in the middle of the channel-forming areas than at their front and back extremities. In such a case, the order of appearance of the different transversal sections S1, S2, starting from the front edge of the core may be inverted. The channel-forming areas may also comprise a portion that is straight and oriented parallel to the longitudinal axis and another portion that is curved (not represented). For example the channel-forming areas may be curved as shown in FIG. 5 from the front zone of the core up to the middle of the channel-forming areas (at the closest point between the channel-forming areas) and then further extend longitudinally parallel towards the rear edge of the core. In this case, the third section S3 where the basis weight in the central and lateral absorbent zones is about the same may extend up to the back extremities of the channel-forming areas 26.

Figure 8:
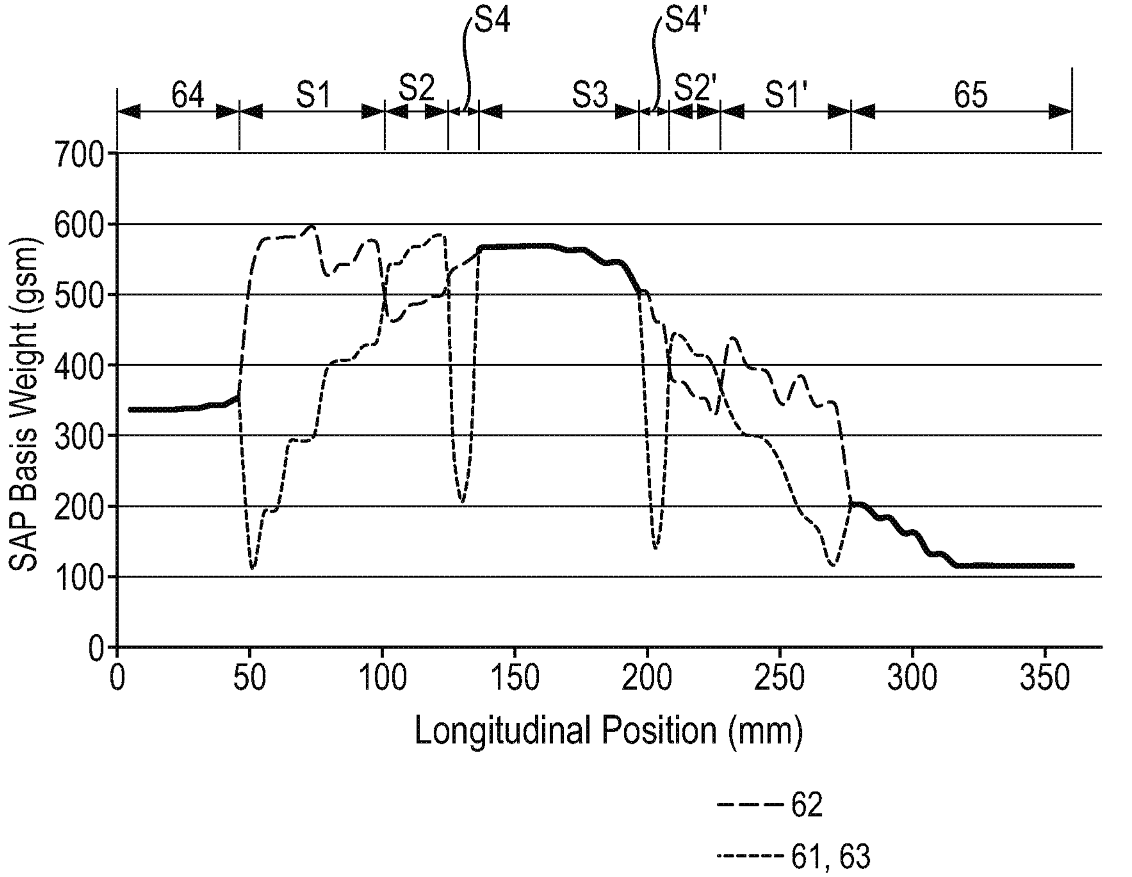
FIG. 8 shows the relationship between the basis weight of the absorbent material and the position along the longitudinal axis in the core of FIG. 7.

The absorbent cores of the invention may further comprise one, two or more transversally orientated folding lines 66, 66' that facilitate the folding of the core along these lines. FIGS. 7-8 show an example of an absorbent core with an SAP distribution similar to the core of FIGS. 5-6 with the difference that this absorbent core further comprises two transversal folding lines 66, 66' formed in transversal sections S4, S4'. Absorbent cores comprising at least one folding line, in particular two or more folding lines, can more easily fold along these folding lines thus increasing the flexibility of the absorbent core in the longitudinal direction. The folding lines may in particular be provided along transversal sections S4, S4' wherein the basis weight in the lateral absorbent zones reaches a minimum relative to the immediately adjacent regions of the lateral absorbent zones in longitudinal direction. These transversal sections S4, S4' are however advantageously not completely free of absorbent material so as not to compromise the absorbency of the core by creating routes for a fluid to escape towards the periphery of the core. The sections of minimum basis weight forming the folding lines may be advantageously relatively narrow (for example having a length of from 5 mm to 30 mm, e.g. as represented in FIG. 7 of about 15 mm) and can serve as hinges for the absorbent core, especially when the core has swollen. They can provide a more conformable absorbent core, even when the basis weight of the central absorbent zone remain relatively high. This can increase the wearing comfort of the article while keeping satisfactory absorbency properties. While not represented, it is also possible that the basis weight of the absorbent material in the central absorbent zone 62 reaches a minimum in the further sections S4, S4' as for the lateral absorbent zones.

The transversal folding lines may be advantageously be oriented completely parallel to the transversal direction as this may be easier to make, however it is not excluded that the transversal lines may also be present at an angle relative to this direction, for example of up to 60° in particular of up to 45°. In that case each folding line may still be typically symmetrically disposed relative to the longitudinal axis, similar to the shape of the comparison signs < or >. The folding lines are advantageously formed by regions or sections S4, S4' of the central and/or lateral absorbent zones that have a minimum basis weight relative to the immediately adjacent regions of the absorbent zone. However it is not excluded that the folding lines may be obtained by other known methods. For example if the absorbent material comprises a compressible material such as cellulose fibers, folding lines may be obtained by embossing the absorbent material in the position and the direction desired. However these other methods may not be as efficient as the one exemplified.

In the example illustrated in FIGS. 7-8, the total amount of SAP in the core may be about 12 g, distributed as follows: 11.5% in the front absorbent zone, 32% in the central absorbent zone, 23% in each lateral absorbent zone, and 10.5% in the back absorbent zone (for a total of 100%). The following table further provides non-limiting exemplary ranges for the dimensions (in the longitudinal direction) and the basis weight of the material in each section for a core as in FIGS. 7-8. As in the previous table, the lowest values indicated are adapted for smaller sizes of diapers and the larger values are adapted for larger sizes of absorbent diapers.

| Zones | Range length (mm) | Min/Max basis weight (g/m$^2$) |
|---|---|---|
| Front absorbent zone 64 | 42-62 | 200-400 |
| S1 | 35-70 | 50-500 (Zones 61, 63)<br>300-600 (Zone 62) |
| S2 | 20-40 | 300-600 (61, 63)<br>250-550 (62) |
| S4 | 10-20 | 100-300 (61, 63)<br>300-650 (62) |
| S3 | 35-65 | 300-650 (61, 63)<br>300-650 (62) |
| S4' | 10-20 | 100-300 (61, 63)<br>300-650 (62) |
| S2' | 15-35 | 200-450 (61, 63)<br>150-400 (62) |
| S1' | 20-45 | 50-400 (61, 63)<br>150-450 (62) |
| Back absorbent zone 65 | 81-134 | 50-250 |

Core Wrap 16, 16'

The absorbent core comprises a core wrap which encloses the absorbent material. The core wrap typically serves a substrate for receiving the absorbent material when the core is made. Various core wrap constructions are possible. The core wrap may in particular comprise as represented in the Figures two separate substrates 16, 16' forming the top side and the bottom side of the core wrap respectively. Having two different substrates for example allows to deposit about half of the absorbent material on each substrate separately before combining these to form the core wrap. The two substrates may be attached in a C-wrap configuration with two longitudinal seals 284', 286', and optionally a front seal 280' and a back seal 282' as will be detailed further below. However this core wrap construction is not limiting of the invention, as any conventional core wrap construction may also be used, for example a single substrate on a portion of which the absorbent material is deposited and then the rest of the substrate folded over the deposited absorbent material to form the other side of the core. This single substrate construction can then be sealed longitudinally with a single longitudinal edge seal. The core wrap may also comprise two substrates disposed flat in a face to face relation (sandwich).

The substrates may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven (“S”) or meltblown nonwoven (“M”), and laminates of any of these. For example spunmelt polypropylene nonwovens are suitable, in particular those having a laminate web SMS, or SMMS, or SSMMS, structure, and having a basis weight range of about 5 g/m$^2$ to 15 g/m$^2$. Suitable materials are for example disclosed in U.S. Pat. No. 7,744,576, US 2011/0268932 A1, US 2011/0319848 A1 and US 2011/0250413 A1. Nonwoven materials are typically made of synthetic fibers, such as PE, PET and in particular PP fibers. It is also possible that the core wrap may be at least partially formed from a component of the article having another function. For example, it is possible that the backsheet may form the bottom side of the core wrap and/or that a distribution layer or the topsheet may form the top side of the core wrap. However, typically the core wrap is made of one or more substrates whose only function is to receive and enclose the absorbent material, as indicated previously.

As used herein, the terms "nonwoven layer" or "nonwoven web" generally means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yam). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

As illustrated in FIG. 2, a first substrate 16 may substantially form the whole of the top surface 288 of the core wrap and a second substrate 16' substantially form the whole of the bottom surface 290 of the core wrap, but it is not excluded that this may be the other way round. By "substantially forming the whole of the surface", it is meant that the outwardly extending flaps of the other substrate that have been folded longitudinally may also form part of the surface considered. The substrates are typically substantially planar in the same plane as the absorbent core, and each comprises an external surface and an internal surface. The internal surface is orientated towards the absorbent material and the external surface is the opposite surface. At least one of the substrate comprises at least one, and advantageously two outwardly extending flaps, which are folded around the front, back or side edges of the absorbent core and then attached to the external surface of the other substrate to form at least one so-called C-wrap seal. As seen in FIG. 2, the first substrate 16 may comprise two side flaps laterally extending along the length of the core and which are folded inwardly over each side edge 284, 286 of the absorbent core. The flaps may be attached to the outer surface of the second substrate 16' for example by using an adhesive seal along each C-wrap seal 284', 286'. One or two continuous or semi-continuous lines of glue may be typically applied along the length of the flaps to bond the inner surface of the flaps to the external surface of the other substrate.

As exemplarily represented in FIG. 3, the core may also comprise so-called sandwich seals 280', 282' where the two substrates are bonded along one edge of the core to each other in face-to-face relationship with the inner surface of each substrate bonded to the inner surface of the other substrate. These sandwich seals can for example be formed using a hotmelt glue applied in a series of stripes in a direction perpendicular of the edge, as shown on the front edge 280 and back edge 282 of the core on FIG. 1 for example.

The substrates may typically be commercially supplied as rolls of material of several hundred meters of length. Each roll is then integrated in the converting line and unrolled at high speed while the auxiliary adhesive, the absorbent material and the fibrous thermoplastic adhesive layer if present are deposited or applied on the substrate and then further converted into an absorbent core when a core wrap enclosing the absorbent material is formed by the second substrate. Typically the machine direction (MD) of the converting line may correspond to the longitudinal direction (y) of the substrate/core and the cross-machine direction (CD) to the transversal direction (x) of the substrate/core. The substrates may be cut along the front and back edges of the core 280, 282 to individualize the core. This will be further exemplarily discussed in the process section further below.

Absorbent Material 60

The absorbent material may be any known absorbent material known in the art, but will typically comprise or consist of superabsorbent polymers (herein referred to as "SAP"). The SAP may be typically in particulate forms (superabsorbent polymer particles), optionally mixed with cellulose fibers, but it not excluded that other forms of SAP may be used such as a superabsorbent polymer foam for example. The SAP useful in the present invention includes a variety of water-insoluble, but water-swellable polymers capable of absorbing large quantities of fluids.

The term "superabsorbent polymer" refers herein to absorbent materials, which may be cross-linked polymeric materials, that can typically absorb at least 10 times their weight of an aqueous 0.9% saline solution as measured using the Centrifuge Retention Capacity (CRC) test (EDANA method WSP 241.2.R3 (12). The SAP may in particular have a CRC value of more than 20 g/g, or more than 24 g/g, or of from 20 to 50 g/g, or from 20 to 40 g/g, or 24 to 30 g/g.

The absorbent material may comprise a relative high amount of SAP, in particular the absorbent material may comprise at least 80%, in particular at least 85%, 90%, 95% and up to 100% of SAP by weight of the absorbent material. The absorbent material may in particular comprise no or only small amount of cellulose fibers, such as less than 20%, in particular less than 10%, 5% or even 0% of cellulose fibers by weight of the absorbent material. The absorbent material may thus consist or consist essentially of SAP. The core wrap is not considered as absorbent material for the purpose of calculating the percentage of SAP in the absorbent core. When the absorbent material comprises cellulose fibers, the content of SAP may typically range from 60% to 80% by weight of the absorbent material.

The superabsorbent polymers may be in particulate form so as to be flowable in the dry state and thus easily deposited on a substrate. Typical particulate absorbent polymer materials are made of poly(meth)acrylic acid polymers. However, starch-based particulate absorbent polymer materials may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in WO 07/047598, WO 07/046052, WO 2009/155265 and WO 2009/155264. Suitable superabsorbent polymer particles may be obtained by current state of the art production processes, for example as described in WO 2006/083584. The superabsorbent polymers are preferably internally cross-linked, i.e. the polymerization is carried out in the presence of compounds having two or more polymerizable groups which can be free-radically copolymerized into the polymer network. In some embodiments, the SAP are formed from polyacrylic acid polymers/polyacrylate polymers, for example having a neutralization degree of from 60% to 90%, or about 75%, having for example sodium counter ions.

The SAP particles may be relatively small (under 1 mm in their longest dimension) in their dry state and may be roughly circular in shape, but granules, fibers, flakes, spheres, powders, platelets and other shapes and forms are also known to persons skilled in the art. Typically, the SAP may be in the form of spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 μm, or from 50 μm to 850 μm, preferably from 100 μm to 710 μm, more preferably from 150 μm to 650 μm, as measured according to EDANA method WSP 220.2-05. SAP having a relatively low particle size help to increase the surface area of the absorbent material which is in contact with liquid exudates and therefore support fast absorption of liquid exudates.

The absorbent core will typically comprise only one type of SAP, but it is not excluded that a blend of different SAPs may be used. The fluid permeability of a superabsorbent polymer can be quantified using its Urine Permeability Measurement (UPM) value, as measured in the test disclosed in US patent application number US2014/005622A1. The UPM of the SAP may for example be of at least $10\times10^{-7}$ $cm^3$.sec/g, or at least $30\times10^{-7}$ $cm^3$.sec/g, or at least $50\times10^{-7}$ $cm^3$.sec/g, or more, e.g. at least 80 or $100\times10^{-7}$ $cm^3$.sec/g. The SAP particles may have a time to reach an uptake of 20 g/g (T20) of less than 240 s, preferably from 40 s to less than 240 s, more preferably from 65 s to 215 s, as measured according to the K(t) test method as described in WO2015/041784 (Peri et al).

Absorbent Material Deposition Area

The absorbent material 60 defines as seen from above as in FIG. 1 an absorbent material deposition area having a periphery that may generally follow the front, back and longitudinal side edges of the core. The absorbent material deposition area can be generally rectangular, for example as shown in FIG. 1, but other shapes can also be used such as a "T" or "Y" or "sand-hour" or "dog-bone" shape. In particular the deposition area may be tapered along its width towards the crotch region of the core. In this way, the absorbent material deposition area may have a relatively narrow width in an area of the core intended to be placed in the crotch region of the absorbent article. This may provide for example better wearing comfort. The absorbent material deposition area may for example have a width (as measured in the transversal direction x) at its narrowest point which is less than about 100 mm, 90 mm, 80 mm, 70 mm, 60 mm or even less than about 50 mm. This narrowest width may be for example at least 5 mm, or at least 10 mm, smaller than the width of the deposition area at its largest point in the front and/or back regions of the deposition area. The channel-forming areas 26 are typically encompassed within the absorbent material area, and are typically completely surrounded by absorbent material, i.e. the channel-forming areas do not extend to any edges of the absorbent material deposition area.

The absorbent material 60 may be deposited on any of the substrates using known techniques, which may allow relatively precise deposition of absorbent material at relatively high speed. In particular the SAP printing technology as disclosed for example in US2006/024433 (Blessing), US2008/0312617 and US2010/0051166A1 (both to Hundorf et al.) may be used. This technique uses a transfer device such as a printing roll to deposit SAP onto a substrate disposed on a grid of a support which may include a plurality of cross-bars 36 extending substantially parallel to each other and spaced apart from one another. The zones 26 substantially free of absorbent material through which the bonding 27 is executed can be formed for example by modifying the pattern of the grid and receiving drums so that no SAP is applied in the selected areas, as exemplary disclosed in US2012/0312491 (Jackels). This technology allows high-speed and precise deposition of SAP on a substrate in particular to provide one or more area(s) substantially free of absorbent material surrounded by absorbent material.

The absorbent material may be substantially continuously distributed in the deposition area. By "substantially continuous" it is meant that at least 50%, or at least to 70% and up to 100% of the deposition area comprises a continuous layer of absorbent material as seen from the top side of the core. The absorbent material may be for example applied as a single continuous layer on one of the substrate, the layer thus directly forming the material deposition area. A continuous layer of absorbent material, in particular of SAP, may also be obtained by combining two absorbent layers having matching (offset) discontinuous absorbent material application pattern wherein the resulting layer is substantially continuously distributed across the absorbent material deposition area, as exemplarily taught in US2008/0312622A1 (Hundorf), and as exemplarily shown on FIG. 3-4. Each individual absorbent material layer comprises a pattern having absorbent material land areas 75, 75' separated by absorbent material-free junction areas 76, 76'. The absorbent material areas 75 of the first layer correspond substantially to the absorbent material-free junction areas 76' of the second layer and vice versa. As exemplary shown in FIGS. 3-4, the absorbent core 28 may thus comprise a first absorbent layer and a second absorbent layer deposited respectively on the first substrate 16 and second substrate 16' and combined together. The first and second absorbent layers may be deposited as series of transversally oriented dots which immediately after deposition merge into transversal stripes or "land areas" having the desired width. Each absorbent layer may comprise for example between 5 and 50 of these generally transversally orientated land areas. These land areas may have for example a width ranging from 4 to 20 mm, in particular 10 mm, as measured in the longitudinal direction (y). The land areas 75 may be of uniform length in the transversal direction (x) but they may have different width, in particular towards the center or crotch section of the absorbent structure to form so called "dog bone" or "hour-glass" shape, which shows a tapering along its width at least in the crotch zone of the structure. The width of the junction areas 76 between the land areas 75 may typically be shorter than the width of the land areas, for example having a width exemplarily ranging from 0.5 to 6 mm, for example 1 to 2 mm. Of course other patterns of deposition for the absorbent material are possible, for example the absorbent material may be deposited as an array of circular or ovoid land areas, or combination of rectangular land areas with circular or ovoid land areas.

In many applications, the liquid discharge occurs predominantly in one area of the core. For diapers, the liquid may predominantly be released towards the crotch region of the core and to a lesser extent the front of the core. Relatively less liquid may be released towards the back of the core. Thus it may be beneficial to profile the amount of absorbent material along the longitudinal direction of the absorbent structure so that more absorbent material is present in the areas where the liquid is more likely to insult the core.

As indicated above, the junction areas 76 of an absorbent layer may advantageously be not directly recognizable in the absorbent core as they will be filled with the land area 75' of the opposed absorbent layer, as shown on FIG. 4. On the other hand, it is an object of the invention that the absorbent material deposition area encompasses at least two channel-forming areas 26. The channel-forming areas 26 may be advantageously substantially free of absorbent material so that the top and bottom sides of the core wrap can be efficiently bonded to another. These channel-forming areas will be exemplified in more details in the following paragraphs.

Channel-Forming Areas 26 and Channels 26'

The absorbent material deposition area of the core encompasses at least two channel-forming areas 26 which are substantially free of absorbent material and preferably through which core wrap bonds 27 are formed. By "substantially free" it is meant that zones do not comprise absorbent material except possibly for minimal amount such as involuntary contaminations with absorbent material particles that may occur during the core making process. The top side 288 of the core wrap is attached to the bottom side 290 of the core wrap by core wrap bonds 27 in the channel-forming areas, in particular through these areas substantially free of absorbent material. The channel-forming areas 26 are advantageously surrounded by absorbent material 60. As illustrated in FIG. 11, when the absorbent material 60 swells upon absorbing a liquid, the core wrap bonds 27 remain at least initially attached in the channel-forming areas 26. The absorbent material 60 swells in the rest of the core when it absorbs a liquid, so that the core wrap forms one or more channels 26' along the channel-forming areas 26 comprising the core wrap bond 27. These channels 26' are three dimensional and can serve to distribute an insulting fluid along their length to a wider area of the core. They may provide a quicker fluid acquisition speed and a better utilization of the absorbent capacity of the core. The channels 26' can also provide a deformation of an overlying layer such as a fibrous layer 54 and provide corresponding ditches 29 in the overlying layer. It is not excluded that the absorbent core may comprise area(s) substantially free of absorbent material without a core wrap bond, but these non-bonded areas will typically not form a channel when wet as effectively as when there is a core wrap bond.

The inner surface of the top side 288 and the inner surface of the bottom side 290 of the core wrap may be bonded together continuously along the channel-forming areas 26, but the core wrap bond 27 may also be discontinuous (intermittent) such as formed by series of point bonds. An auxiliary glue 72 may be used to at least partially form the substrates bond 27. In this case, some pressure may be applied on the substrates in the zones 26 to improve the adhesive bonds between the substrates. If an optional fibrous adhesive 74, 74' is present, it may also help forming the bond 27. If the auxiliary glue is applied as a series of longitudinally orientated continuous slots, the width and frequency of these slots may advantageously be such that at least one slot of auxiliary glue is present at any level of the channel-forming area 26 in the longitudinal direction. For example the slots may be 1 mm wide with a 1 mm distance between each slots, and the channel-forming areas have a width of about 8 mm. Such on average for 4 slots of auxiliary glue will be present in each of the channel-forming area 26. It is of course also possible to form the bonds 27 via other known attachment means, such as pressure bonding, ultrasonic bonding, heat bonding or combination thereof.

The following are non-limiting examples of shape and size of channel-forming areas 26 that are substantially free of absorbent material. In general, the core wrap bond 27 may have the same outline but be slightly smaller than the material free area of the channel-forming areas 26 due to the tolerance required for registration in the manufacturing process. The channel-forming areas are advantageously present at least within the crotch region of the core, in particular at least at the same longitudinal level as the crotch point C. The channel-forming areas 26 may comprise, as exemplified in FIG. 1, two longitudinally-extending areas substantially free of absorbent material. The channel-forming areas may be symmetrically arranged relative to the longitudinal axis 80. The absorbent core 28 may also comprise more than two channel-forming areas, for example at least 3, or at least 4 or at least 5 or at least 6. Shorter channel-forming areas substantially free of absorbent material may for example be present in the back region or the front region of the core as illustrated for example in the Figures of WO2012/170778.

The channel-forming areas 26 extend substantially longitudinally, meaning that each zone extends at least as much in the longitudinal direction (y) than in the transversal direction (x), and typically at least twice as much in the longitudinal direction than in the transverse direction (as measured after projection on the respective axis). The channel-forming areas 26 may have a length L' projected on the longitudinal axis 80 of the core that is at least 10% of the length L of the absorbent core, in particular from 20% to 80%. The absorbent material-free channel-forming areas may have a width W' along at least part of their length which is at least 2 mm, or at least 3 mm or at least 4 mm, up to for example 20 mm, or 16 mm or 12 mm. The width W' of each areas substantially free of absorbent material may be constant through substantially its whole length or may vary along its length.

As discussed before, the channel-forming areas may be at least partially curved. In particular the channel-forming areas present in the crotch region may be concave towards the longitudinal axis 80 as illustrated in FIG. 1. The radius of curvature may typically be at least equal to the average transverse dimension of the absorbent material deposition area (and in particular at least 1.5 or at least 2.0 times this average transverse dimension). The radius of curvature may be constant or may vary along the length of the channel-forming area. The channel-forming areas may alternatively be straight but under an angle of (e.g. from 5°) up to 30°, or for example up to 20°, or up to 10° with a line parallel to the longitudinal axis. Alternatively, and as illustrated in FIGS. 14-15, the channel-forming areas may be straight, and in particular longitudinally oriented parallel to the longitudinal axis 80.

The channel-forming areas are typically disposed as one or more symmetrical pair(s) relative to the longitudinal axis, and are spaced apart from one another over their whole longitudinal dimension. The shortest spacing distance between the channel-forming areas may be for example at least 5 mm, or at least 10 mm, or at least 16 mm. It is however not excluded that the channels may be joined together, for example at their front or back extremities. Furthermore, in order to reduce the risk of fluid leakages, the areas substantially free of absorbent material may advantageously not extend up to any of the edges of the absorbent material deposition area, and are therefore surrounded by and fully encompassed within the absorbent material deposition area of the core. The smallest distance between a channel-forming area and the closest edge of the absorbent material deposition area may be at least 5 mm.

The three dimensional channels 26' in the absorbent core start forming when the absorbent material absorbs a liquid such as urine and starts swelling. As the core absorbs more liquid, the depressions within the absorbent core formed by core wrap bond 27 between the two substrates will become deeper and more apparent to the eye and the touch. It is possible to create a sufficiently strong core wrap bond combined with a relatively low amount of SAP and/or a relatively extensible substrate material so that the channels remain permanent until complete saturation of the absorbent material. On the other hand, the core wrap bonds may in some cases also restrict the swelling of the absorbent material when the core is substantially loaded. The core wrap bond 27 may also be designed to gradually open in a controlled manner when exposed to a large amount of fluid. The bonds may thus remain substantially intact at least during a first phase as the absorbent material absorbs a moderate quantity of fluid, as shown on FIG. 11. In a second phase the core wrap bonds 27 in the channels can start opening to provide more space for the absorbent material to swell while keeping most of the benefits of the channels such as increased flexibility of the core in transversal direction and fluid management. In a third phase, corresponding to a very high saturation of the absorbent core, a more substantial part of the channel bonds can open to provide even more space for the swelling absorbent material to expand. The strength of core wrap bond 27 within the channels can be controlled for example by varying the amount and nature of the glue used for the attaching the two sides of the core wrap, the pressure used to make the core wrap bond and/or the distribution of the absorbent material, as more absorbent material will usually causes more swelling and will put more pressure on the bond. The extensibility of the material of the core wrap may also play a role.

Auxiliary Glue 72

The auxiliary glue 72 is optional. When present, the auxiliary glue 72 may be applied directly over the inner surface of one or both of the top side and bottom side of the core wrap. The auxiliary glue may at least partially form the bonds 27 between the inner surface of the first substrate 16 and the inner surface of the second substrate 16' through areas substantially free of absorbent material. The auxiliary glue 72 may also be useful to improve the adhesion between the first substrate 16 and both the absorbent material (in the absorbent material land areas 75) and the fibrous thermoplastic material 74 (in the absorbent material-free junction areas 76).

The auxiliary glue may comprise or consist of any kind of thermoplastic hot-melt adhesives used in the field of absorbent core making. Such an adhesive generally includes one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.), a resin or analogous material (sometimes called a tackifier) to provide adhesive strength (e.g., hydrocarbons distilled from petroleum distillates; rosins and/or rosin esters; terpenes derived, for example, from wood or citrus, etc.); and optional waxes, plasticizers or other materials to modify viscosity (e.g., mineral oil, polybutene, paraffin oils, ester oils, and the like), and/or other additives including, but not limited to, antioxidants or other stabilizers. Exemplary suitable commercial adhesives are available from Fuller under reference number 1358LO and from Henkel under reference numbers DM3800 and DM526. Further information about hotmelt adhesive chemistry is discussed below for the fibrous thermoplastic adhesive layer. The auxiliary glue can be applied by any adhesive applicator known in the field, in particular bead, slot or spray nozzles.

The auxiliary glue 72 was discussed above with reference to the first absorbent substrate 16 which forms the upper side 288 of the absorbent core, and which is placed towards the topsheet 24 in the finished absorbent article 20. This is however not limiting, as the first substrate may alternatively form the bottom side 290 of the absorbent core which is placed towards the backsheet 25 of the article 20. It is also considered that a second auxiliary glue may be applied directly on the second substrate 16' in addition to the first auxiliary glue applied directly on the first substrate 16, in particular in any of the configurations discussed above. This may be particular useful when the absorbent material within the core wrap is formed by two absorbent layers 61, 62 as discussed above.

Microfiber Glue 74, 74'

The absorbent core may also comprise a fibrous thermoplastic adhesive material 74, to further immobilize the absorbent material 60 during the making process of the core and usage of the article. The fibrous thermoplastic adhesive material 74, 74' may be in particular useful to immobilize the layers of absorbent material onto their respective substrate 16, 16' where they have been deposited. These absorbent layers may comprise land areas 75, 75' separated by junction areas 76, 76' as discussed above and the fibrous thermoplastic adhesive material 74 may then be at least partially in contact with the absorbent material in the land areas and at least partially in contact with the substrate layer 16, 16' in the junction areas. This imparts an essentially three-dimensional net-like structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material. The fibrous adhesive may be for example sprayed on an absorbent layer after it has been deposited on its substrate during the core making process.

The fibrous thermoplastic adhesive material may have a molecular weight (Mw) of more than 10,000 and a glass transition temperature (Tg) usually below room temperature or $-6°$ C.<Tg<16° C. Typical concentrations of the polymer in a hotmelt are in the range of about 20% to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%. Exemplary commercial suitable adhesives are NW1151 ex. HB Fuller and H2898 ex. Bostik.

The thermoplastic adhesive used for the fibrous layer preferably has elastomeric properties, such that the web formed by the fibers on the SAP layer is able to be stretched as the SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. 4,81,066 (Korpman).

The thermoplastic adhesive material fibers may exemplarily have an average thickness of about 1 to about 50 micrometers or about 1 to about 35 micrometers and an average length of about 5 mm to about 50 mm or about 5 mm to about 30 mm. The auxiliary glue may improve the adhesion of the thermoplastic adhesive material to the substrate. The fibers adhere to each other to form a fibrous layer, which can also be described as a mesh.

Exemplary Method and Apparatus for Making the Absorbent Core

The absorbent cores of the invention may be made by any conventional methods known in the art that allow a relative precise and controlled deposition of absorbent material. The articles may be hand-made or industrially produced at high speed on a modern converting line. As mentioned above, the absorbent core of the invention can in particular be made industrially by combining two absorbent structures 70 and 70' using the SAP printing method first disclosed in WO2008/155699 (Hundorf et al.) and further developed in WO2012/170798A1 (Jackels et al.), with the adaptations required to obtain the specific SAP distribution of the invention. Such a method and apparatus is schematically disclosed in FIG. 12.

Figure 12:
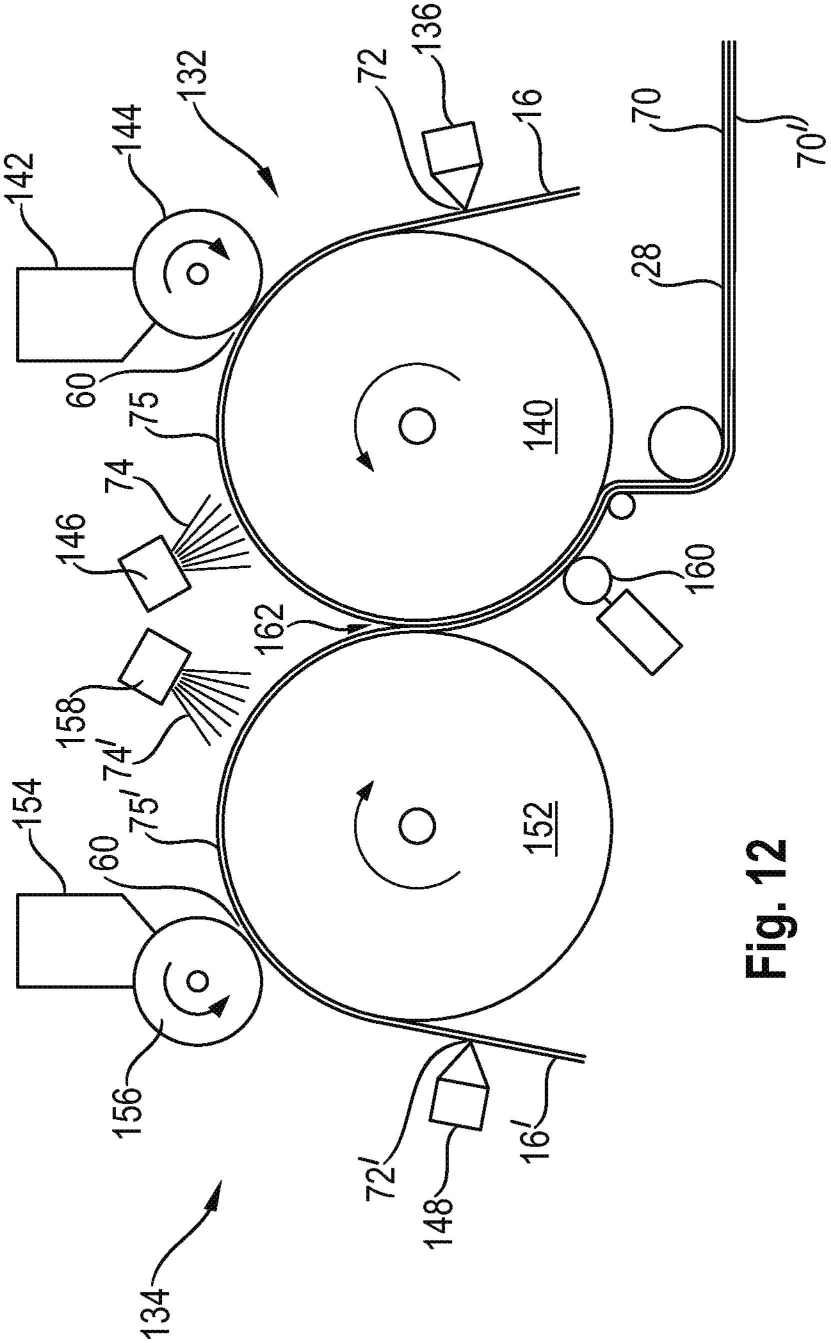
FIG. 12 schematically shows an process for making the absorbent core of the invention.

A first printing unit 132 for making an absorbent structure comprising a substrate 16 and SAP particles 60 is illustrated on the right side of FIG. 12. The first printing unit 132 comprise an auxiliary glue applicator 136 for applying the auxiliary glue 72 to the substrate 16, a first rotatable support roll 140 for receiving the first substrate 16, a first hopper 142 for holding and dispensing an absorbent particulate polymer material 60, a first printing roll 144 for collecting the SAP particles in a predetermined pattern from the hopper 142 and depositing the absorbent particulate polymer onto the support roll 140 to a deposition area on the substrate, and a first thermoplastic adhesive material applicator 146 for applying the fibrous thermoplastic adhesive material 74. The auxiliary glue applicator 136 may be a nozzle system which can provide a relatively thin but wide curtain of thermoplastic adhesive material as suggested in WO2008/155699, but may also alternatively and advantageously comprise a slot coater for applying simultaneously several slots of auxiliary glue 72 longitudinally along a desired width of the substrate.

Figure 13:
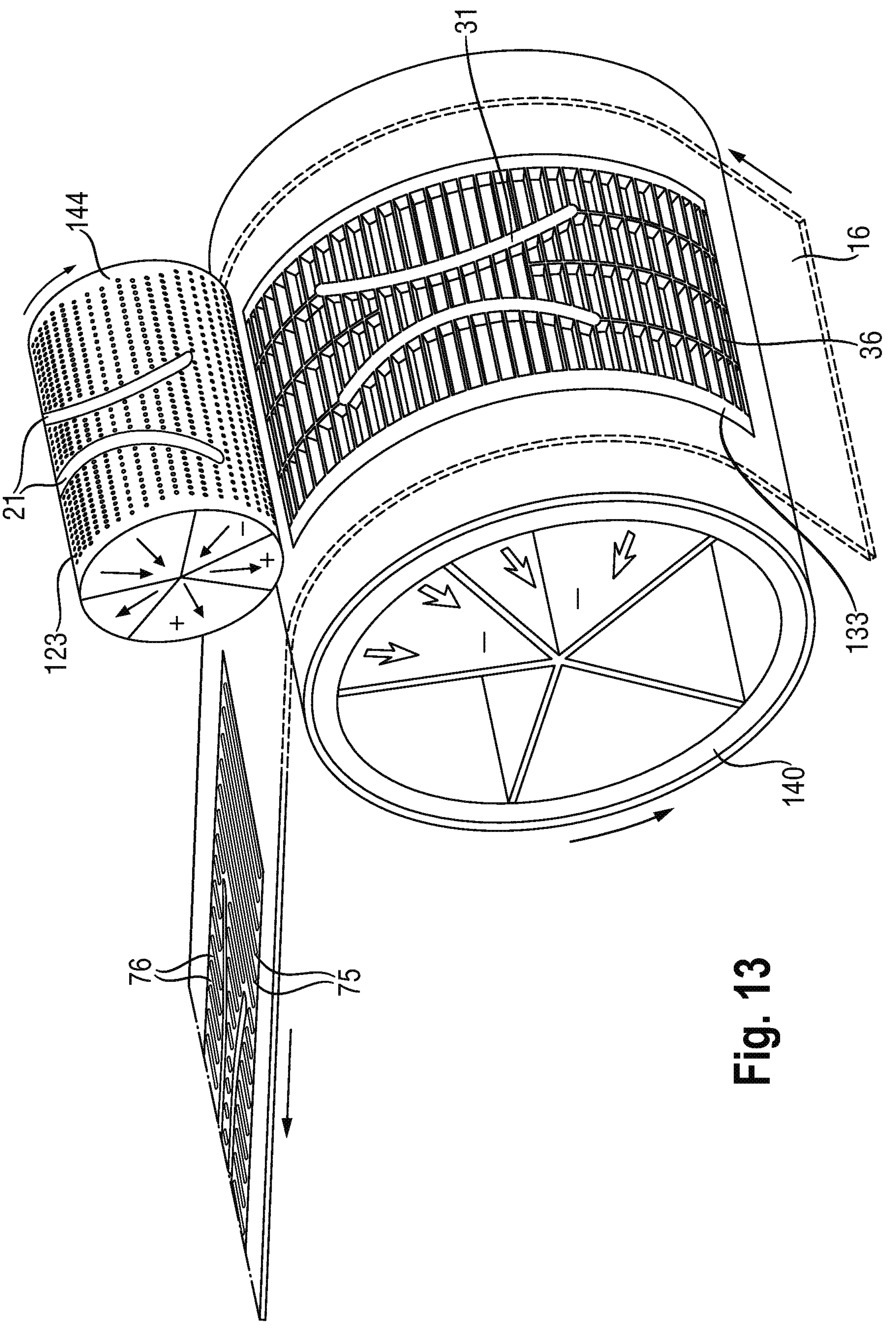
FIG. 13 shows an apparatus for depositing superabsorbent particles that can be used in the process of FIG. 12.

The SAP printing rolls 144, 156 and the support rolls 140, 152 may be as generally taught in WO2012/170798A1, with the printing rolls further modified to provide the desired SAP deposition pattern of the invention. The absorbent material deposition step, or printing step, is schematically illustrated in FIG. 13, which shows separately how the printing roll 144 and the lay-on drum 140 cooperate to precisely deposit the SAP onto the substrate. The printing roll 144 comprises on its periphery a plurality of cavities 123 that can be filled with SAP particles. The cavities 123 have a pre-determined volume so that the amount of SAP filled is precisely controlled. The cavities may have any kind of shape, for example they may generally have an inverted dome-shape. These cavities may be arranged in a series of transversal rows but other arrangements are possible. The size, shape and spacing between adjacent cavities 123 corresponds to the size, shape and spacing between adjacent dots 23, 23' as represented in FIGS. 5 and 7. Thus the cavities 123 will comprise larger cavities and smaller cavities corresponding to the larger and smaller SAP dots respectively that are to be deposited on the substrate. Each printing roll 144 and 156 may each deposit about half of the rows of SAP to provide the offset double layer structure discussed before.

The printing roll 144 shown further comprises a pair of areas 21 free of cavities and surrounded by the cavities 123. These areas 21 correspond to the absorbent material-free areas through which the channel-forming areas 26 will be formed. The areas 21 may be flush with the surface of the printing roll or may be raised. The cavities may be connected to a vacuum (shown by the minus sign "–" in the Figures through a grid (not shown) in the fill area of the drum, typically at the upper region of drum (corresponding ca. to the angle between ca. 11 to 3 o'clock in FIG. 13 as indicated by the inward pointing arrow and the minus "–" sign), the vacuum being also present in an absorbent material retention area (ca. 3 to 5 o'clock) to ensure that the material does not escape the cavities before being deposited. When the cavities approaches the meeting point, the vacuum is switched off and may be replaced by overpressure (represented by the plus signs + for "high" pressure area between ca. 5 and 7 o'clock) to completely blow the SAP out of the cavities onto the substrate. Another internal printing roll chamber with some overpressure (e.g from 7 to 10 'clock) may be provided to clean up the cavities from any remaining SAP before these are filled again for another printing cycle.

The printing-roll 144 comes in close proximity of the lay-on drum 140 at a meeting point so that the SAP can be accurately transferred to the substrate 16 supported on the lay-on drum. The lay-on drum is generally circular and comprises on its periphery at least one and, typically, a plurality of receptacles 133, each receptacle being substantially identical to the preceding and each receptacle providing a deposition area for one absorbent structure. A lay-on drum 140 may for example comprise about four such receptacles 133 for absorbent cores suitable in baby diapers having a size 4. For a given size of the drum, more receptacles may be present if the cores to be made are smaller. The diameter of the printing roll 144 may be as shown smaller than the lay-on drum 140, so that a complete turn of the lay-on drum corresponds to several turns of the printing rolls, e.g. in a relation of 4 to 1 for a medium sized absorbent core as exemplified above (size 4 diapers).

Each receptacle 133 comprises on its surface a pattern of depressions that may be designated by their usual term "air-slots" formed between transversally-oriented rods 36 (also called "CD bars"). The depressions are connected to a vacuum (represented by the minus sign "–" in FIG. 13) as they approach the SAP deposition area at the meeting point. This vacuum helps maintaining the substrate 16 taut on the lay-on drum. Furthermore, this vacuum somewhat pulls the substrate inwards of the surface of the lay-on drum through the depressions. In this way, small undulations are formed at the surface of the substrate matching the outline of the underlying depressions. A grid may be present at the bottom of the depressions. These undulations generally define the shape of the deposited absorbent material area, as the vacuum will also help sucking and directing the SAP from the print roll 144 at the meeting point onto the undulations. The vacuum exerted through each depressions combined by the over-blow pressure on the print roll will bring the deposited SAP to generally follow the shape of the depressions to form continuous areas, and this even if the cavities 122 have another shape such as discrete circular cavities. After passing the meeting point, a lower vacuum may be used to keep the substrate and the SAP in place while the microfiber glue 74 is applied (as shown in FIG. 12 but not shown on FIG. 13).

The receptacle 133 on the lay-on drum may comprise a pair of mating strips 31 that corresponds to the cavity-free areas 21 on the lay-on drum. The mating strips 31 may be flush with the surface of the lay-on drum but may be advantageously slightly raised by a few mm. Such mating strips/cavity-free areas combinations 21, 31 are exemplarily disclosed in further details in US2012/0312491 (Jackels). Of course the number and shape of the cavity-free areas 21/mating strips 31 combination can be adapted to obtain any desired number and shape of material free areas.

The absorbent structures 70, 70' obtained by each printing unit 132, 134 may be combined in a face to face relationship so that the land areas 75, 75' are offset relative to each other to form an absorbent core as illustrated in FIG. 3. The second printing unit 134 as shown on the left side of FIG. 12 may be generally identical to the first printing unit 132. The second printing unit 134 may comprise a second auxiliary glue applicator 148 which may be a slot coater for optionally applying a second auxiliary glue 72' to the substrate 16', a second rotatable support roll 152 for receiving the substrate 16', a second hopper 154 for holding absorbent particulate polymer material, a second printing roll 156 for transferring the absorbent particulate polymer material to the substrate 16', and a thermoplastic adhesive material applicator 158 for applying a thermoplastic fibrous adhesive material 74' to the substrate 16' and the SAP layer 75' thereon.

The absorbent structures may be combined by applying pressure in the nip 162 between the two support rolls 140, 152, forming at the same time the core wrap bond 27 between the two substrates. The core wrap bonds may be alternatively formed further down the line by other methods such as ultrasonic bonding. The longitudinal side seals are formed as a C-wrap in the seal forming guide roller 160 by continuously folding the laterally extending flaps of one of the substrate. The absorbent cores 28 can then be individualized by forming the front and back seals and cutting the web of the core material at the required interval. The continuous flow of absorbent cores can then be integrated into a converting process for making an absorbent article.

General Description of the Absorbent Article 20

Figure 10:
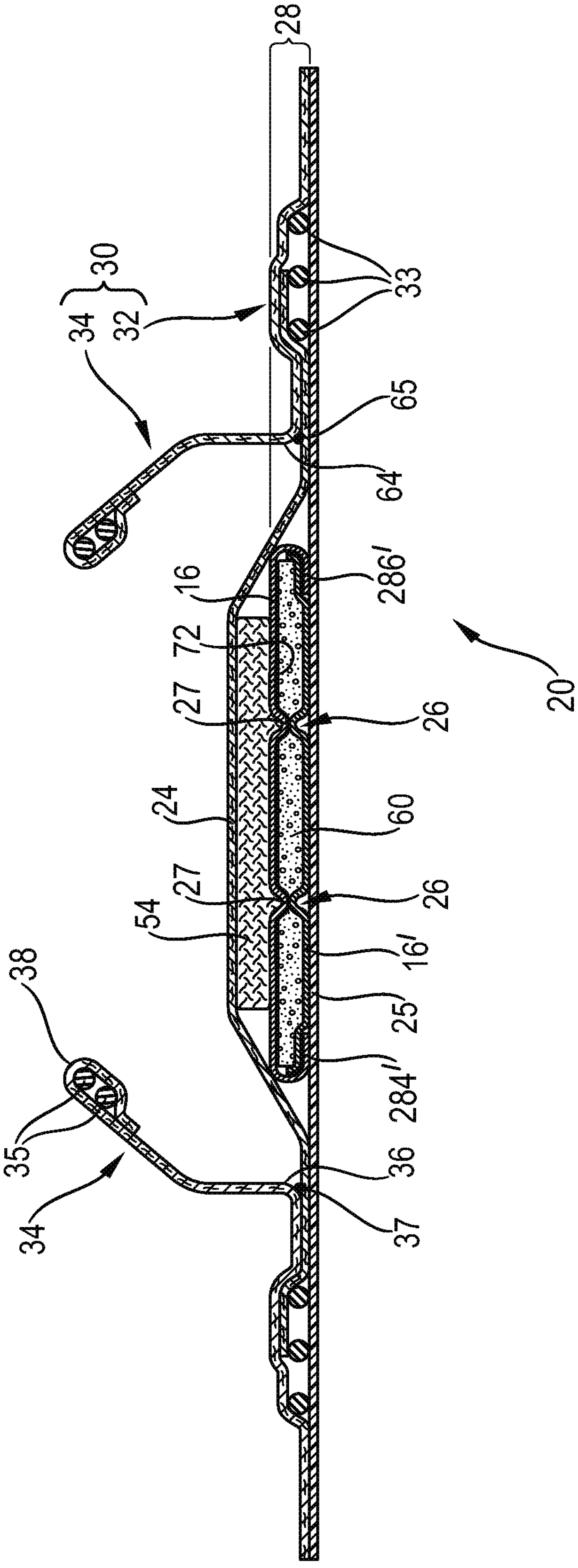
FIG. 10 shows a transversal cross-section of FIG. 9.

An exemplary absorbent article according to the invention in the form of a baby taped diaper 20 is represented in FIGS. 9 and 10. FIG. 9 is a top plan view of the exemplary diaper 20, in a flat-out state, with portions of the structure being cut-away to more clearly show the construction of the diaper 20. FIG. 10 is transversal cross-sectional view of the diaper 20 taken along line 10-10 in FIG. 9. This diaper 20 is shown for illustration purpose only as the invention may be used for making a wide variety of diapers or other absorbent articles such as training pants, adult incontinence pants or feminine sanitary pads.

The absorbent article 20 comprises a liquid permeable topsheet 24, a liquid impermeable backsheet 25 and an absorbent core 28 according to the invention between the topsheet and the backsheet. The absorbent article may also comprise further typical components such as an acquisition layer and/or a distribution layer (collectively referred to as acquisition-distribution system "ADS", designated as 54), and elasticized gasketing cuffs 32 present between topsheet and backsheet and upstanding barrier leg cuffs 34, which will be further detailed in the following. The Figures also show other typical taped diaper components such as a fastening system comprising fastening tabs 42 attached towards the back edge 12 of the article and cooperating with a landing zone 44 towards the front edge 10 of the article. The absorbent article may also comprise other typical components, which are not represented in the Figures, such as a back elastic waist feature, a front elastic waist feature, transverse barrier cuffs, a lotion application, etc.

The absorbent article 20 comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The absorbent article may be notionally divided by a longitudinal axis 80' extending from the front edge to the back edge of the article and dividing the article in two substantially symmetrical halves relative to this axis, when viewing the article from the wearer facing side in a flat out configuration, as exemplarily shown in FIG. 9. This axis 80' may typically be concomitant with the longitudinal axis 80 of the core. If some part of the article is under tension due to elasticized components, the article may be typically flattened using clamps along the periphery of the article and/or a sticky surface, so that the topsheet and backsheet can be pulled taut so as to be substantially flat. Closed articles such as training pant may be cut open along the side seams to apply them on a flat surface. Unless otherwise indicated, dimensions and areas disclosed herein apply to the article in this flat-out configuration. The article has a length L" as measured along the axis 80' from the back edge to the front edge. The absorbent article 20 can also be notionally divided by a transversal axis 90' into a front region and a back region of equal length measured on the longitudinal axis, when the article is in such a flat state. This article's transversal axis 90' is perpendicular to the longitudinal axis 80' and placed at half the length of the article.

The topsheet 24, the backsheet 25, the absorbent core 28 and the other article components may be assembled in a variety of well-known configurations, in particular by gluing and/or heat embossing. Exemplary diaper assemblies are for example generally described in U.S. Pat. Nos. 3,860,003, 5,221,274, 5,554,145, 5,569,234, 5,580,411, and 6,004,306. The absorbent article is preferably thin. The article may be advantageously thin at the intersection of the longitudinal and transversal axes, for example with a caliper of from 1.0 mm to 8.0 mm, in particular from 1.5 mm to 6.0 mm, as measured using the Absorbent Article Caliper Test described below.

Topsheet 24

The topsheet 24 typically forms the majority of the wearer-contacting surface of the article and is the first layer that the body exudates contact. The topsheet is preferably compliant, soft-feeling, and non-irritating to the wearer's skin. Further, at least a portion of the topsheet is liquid permeable, permitting liquids to readily penetrate through its thickness. Any known topsheet may be used in the present invention. A suitable topsheet may be manufactured from a wide range of materials. Most topsheets are nonwoven materials or apertured formed films, but other material are possible such as porous foams, reticulated foams, woven materials. Typical diaper topsheets have a basis weight of from about 10 g/m$^2$ to about 28 g/m$^2$, in particular between from about 12 g/m$^2$ to about 18 g/m$^2$ but higher basis weights are possible if it is desired to provide a very soft feeling wearer-contacting surface for example.

Nonwoven topsheets may be made of natural fibers (e.g., wood or cotton fibers), synthetic fibers or filaments (e.g. polyester or polypropylene or bicomponent PE/PP fibers or mixtures thereof), or a combination of natural and synthetic fibers. If the topsheet includes nonwoven fibers, the fibers may be spunbond, carded, wet-laid, meltblown, hydroentangled, or otherwise processed as is known in the art. In particular the topsheet may be a spunbond PP nonwoven. A suitable topsheet comprising a web of staple-length polypropylene fibers is manufactured by Veratec, Inc., a Division of International Paper Company, of Walpole, MA under the designation P-8.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, VA, as "CLIFF-T". The topsheet may also have a three-dimensional appearance and feel, or there may be an additional, smaller, three-dimensional layer placed on top of the topsheet. Such three-dimensional additional layers may be for example particularly useful to receive low viscous exudates such as the stool of young babies Examples of such fluid entangled dual layered three-dimensional materials and processes to obtain them have been disclosed for example in US2014/0121623A1, US2014/0121621A1, US2014/0121624A1, US2014/0121625A1.

The topsheet may also be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US2003/148684 and US2005/008839 (Cramer et al.) and U.S. Pat. No. 7,112,621 (Rohrbaugh et al). Any portion of the topsheet may also coated with a lotion as is known in the art. Examples of suitable lotions include those described in U.S. Pat. Nos. 5,607,760, 5,609,587, 5,643,588, 5,968,025 and 6,716,441. The topsheet 24 may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 cm$^2$ and about 50 cm$^2$, in particular between about 15 cm$^2$ and 35 cm$^2$. Examples of apertured topsheet are disclosed in U.S. Pat. No. 6,632,504. WO 2011/163582 also discloses suitable colored topsheet having a basis weight of from 12 g/m$^2$ to 18 g/m$^2$ and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet.

Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g., urine). The backsheet may, for example, be or comprise a thin plastic film such as a thermoplastic film having a thickness of about 0.012 mm to about 0.051 mm. The basis weight of those films is usually as low as possible to save material costs, typically from 10 gsm to 30 gsm, in particular below 20 gsm. A covering low basis weight nonwoven may be attached to the external surface of the film to provide for a softer touch.

Suitable backsheet materials include breathable materials which permit vapors to escape from the absorbent article while still preventing, or at least inhibiting, exudates from passing through the backsheet. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, VA, and sold under the designation EXAIRE, and monolithic films such as manufactured by Clopay Corporation, Cincinnati, OH under the name HYTREL blend P18-3097.

The film may include at least about 20 weight percent filler particles, for example filler particles that include calcium carbonate, so that wherein the film has been stretched in the machine direction, e.g. to at least about 150 percent, fractures are formed where said filler particles are located. The films may be biaxially stretched at least about 150 percent in the machine direction and a transverse direction to cause fractures to form where said filler particles are located. Breathable films may generally have Water Vapor Transmission Rates (WVTR) in excess of 300 grams per square meter per 24 hours. The WVTR may be measured by the Desiccant Method as indicated in ASTM E96/E96M-14.

U.S. Pat. No. 6,075,179 for example discloses a suitable multilayer film comprising: a core layer made from an extrudable thermoplastic polymer, the core layer having a first exterior surface and a second exterior surface, a first skin layer attached to the first exterior surface of said core layer to form the multilayer film, the multilayer film defining an overall thickness. The first skin layer defines a first skin thickness, and comprising less than about ten percent of said overall thickness. The overall thickness is not exceeding about 30 micrometers and the multilayer film is a liquid barrier and has a WVTR of at least 300 g/m$^2$/24 hours.

The backsheet may further typically comprise a nonwoven on its most external side to improve softness. Exemplary laminates comprising a breathable film and a nonwoven layer are for example disclosed in WO2014/022,362A1, WO2014/022,652A1 and U.S. Pat. No. 5,837,352. The nonwoven web may in particular comprise a spunbond nonwoven web and/or a laminate of a spunbond nonwoven web and a meltblown nonwoven web. The laminate may also have a water vapor transmission rate of at least 300 $g/m^2/24$ hours. U.S. Pat. No. 5,843,056 for example discloses substantially liquid impermeable, vapor permeable composite backsheet.

Acquisition-Distribution System 54

The absorbent articles of the invention may comprise an acquisition layer, a distribution layer, or a combination of both (herein collectively referred to as acquisition-distribution system "ADS"). The function of the ADS is typically to quickly acquire the fluid and distribute it to the absorbent core in an efficient manner. The ADS may comprise one, two or more layers, which may form a unitary layer or remain discrete layers which may be attached to each other. For the benefit of simplicity, the ADS is represented in FIGS. 9-11 as a single layer 54. The ADS may however comprise in particular two layers: a distribution layer directly under the topsheet and an acquisition layer disposed between the distribution layer and the absorbent core, but the invention is not restricted to this example. Typically, the ADS will not comprise SAP as this may slow the acquisition and distribution of the fluid. The prior art discloses many type of acquisition-distribution system, see for example WO2000/59430 (Daley), WO95/10996 (Richards), U.S. Pat. No. 5,700,254 (McDowall), WO 02/067809 (Graef).

Any of the acquisition layer and/or in particular the distribution layer may be profiled in the longitudinal direction and/or the transversal direction, as exemplary disclosed in WO2014/93323 (Bianchi et al.), so that more material of these layers is present towards the front of the article rather than the back. Any of the acquisition layer and/or in particular the distribution layer may also comprise material free-areas disposed within the acquisition or distribution layer. These material free areas can generally match the shape and position of the channel-forming areas 26 of the absorbent core to provide a channel for the fluid to directly quickly reach a large area of the absorbent core. The topsheet may be bonded through these material areas directly or indirectly to the zones of the core wrap corresponding to the channel-forming areas. These material free areas in the distribution layer (and/or the acquisition layer) may be smaller than the channel-forming areas, as typically the acquisition and distribution layers are smaller than the absorbent core. Examples of such distribution layers having material-free channels matching the channel-forming areas of the absorbent core are disclosed for example in WO2015/31225, WO2015/31229, WO2015/31243, WO 2015/031256 (Roe et al.).

Examples of materials that can be used as distribution layer and acquisition layer are exemplified in more detail in the following sections.

Acquisition Layer

The absorbent article 20 may comprise an acquisition layer, whose function is to quickly acquire the fluid away from the topsheet so as to provide a good dryness for the wearer. The acquisition layer is typically placed directly under the topsheet. If present, the distribution layer may be at least partially disposed under the acquisition layer. The acquisition layer may typically be or comprise a non-woven material, for example a SMS or SMMS material, comprising a spunbonded, a melt-blown and a further spunbonded layer, or a spunlaced nonwoven, or alternatively a carded chemical-bonded nonwoven. The non-woven material may in particular be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US2003/148684 (Cramer et al.) and US2005/008839 (Cramer et al.). The acquisition layer may be stabilized by a latex binder, for example a styrene-butadiene latex binder (SB latex). Processes for obtaining such latices are known, for example, from EP 149880 (Kwok) and US 2003/0105190 (Diehl et al.). The binder may typically be present in the acquisition layer in amount ranging from about 12% to about 50%, for example about 30%, by total weight of the acquisition layer. SB latex is available under the trade name GENFLO™ 3160 (OMNOVA Solutions Inc.; Akron, Ohio).

Another typical acquisition layer, sometimes referred to as secondary topsheet, may for example be a through-air bonded carded web ("TABCW") but many other alternatives material are known in the art and may be used instead. "Bonded carded web" refers to webs that are made from staple fibers that are sent through a combing or carding unit, which breaks apart and aligns the staple fibers in the machine direction to form a generally machine direction-oriented fibrous nonwoven web. This web is then drawn through a heated drum, creating bonds throughout the fabric without applying specific pressure (thru air bonding process). The TABCW material provides a low density, lofty through-air bonded carded web. The web may for example have a specific weight basis level at about 15 gsm to about 120 gsm (gram per $m^2$), in particular about 30 gsm to about 80 gsm. The TABCW material can for example comprise about 3 to about 10 denier staple fibers. Examples of such TABCW are disclosed in WO2000/71067 (KIM DOO-HONG et al.). TABCW are available directly from all usual suppliers of nonwoven webs for use in absorbent articles, for example Fitesa Ltd or Fiberweb Technical Nonwovens.

A further acquisition layer (not shown) may be used in addition to the first acquisition layer described above. For example a tissue layer may be placed between the first acquisition layer and the distribution layer. The tissue may have enhanced capillarity distribution properties compared to the acquisition layers described above. The tissue and the first acquisition layer may be of the same size or may be of different size, for example the tissue layer may extend further in the back of the absorbent article than the first acquisition layer. An example of a hydrophilic tissue is a 13 to 15 gsm high wet strength tissue made of cellulose fibers from supplier Havix.

Distribution Layer

The absorbent article 20 may also comprise a distribution layer, whose function is to spread the insulting fluid liquid over a larger surface within the article so that the absorbent capacity of the core can be more efficiently used. Typically the distribution layer is made of a nonwoven material based on synthetic or cellulosic fibers and having a relatively low density. The density of the distribution layer may vary depending on the compression of the article, but may typically range from 0.03 $g/cm^3$ to 0.25 $g/cm^3$, in particular from 0.05 g/cm$^3$ to 0.15 g/cm$^3$ measured at 0.30 psi (2.07 kPa). The material used to make the distribution layer may have a Water Retention Value of from 2 to 60, in particular from 3 to 40, more particularly from 4 to 20, measured as indicated in Water Retention Value Measurement Procedure below. The distribution layer may typically have an average basis weight of from 30 g/m$^2$ to 400 g/m$^2$, in particular from 100 g/m$^2$ to 300 g/m$^2$. When a nonwoven acquisition layer is present, the distribution layer may be first deposited on the acquisition layer as substrate before being further joined to absorbent core as is known in the art.

The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance against the compression in the product packaging or in use conditions, e.g. under baby weight.

Exemplary chemically cross-linked cellulosic fibers suitable for a distribution layer are disclosed in U.S. Pat. Nos. 5,549,791, 5,137,537, WO95/34329 or US2007/118087. Exemplary cross-linking agents include polycarboxylic acids such as citric acid and/or polyacrylic acids such as acrylic acid and maleic acid copolymers. For example, the cross-linked cellulosic fibers may have between about 0.5 mole % and about 10.0 mole % of a C2-C9 polycarboxylic acid cross-linking agent, calculated on a cellulose anhydroglucose molar basis, reacted with said fibers in an intrafiber ester crosslink bond form. The C2-C9 polycarboxylic acid cross-linking agent may be selected from the group consisting of:

- aliphatic and alicyclic C2-C9 polycarboxylic acids having at least three carboxyl groups per molecule; and
- aliphatic and alicyclic C2-C9 polycarboxylic acids having two carboxyl groups per molecule and having a carbon-carbon double bond located alpha, beta to one or both of the carboxyl groups, wherein one carboxyl group in said C2-C9 polycarboxylic acid cross-linking agent is separated from a second carboxyl group by either two or three carbon atoms. The fibers may have in particular between about 1.5 mole % and about 6.0 mole % cross-linking agent, calculated on a cellulose anhydroglucose molar basis, reacted therewith in the form of intrafiber ester crosslink bonds. The cross-linking agent may be selected from the group consisting of citric acid, 1, 2, 3, 4 butane tetracarboxylic acid, and 1, 2, 3 propane tricarboxylic acid, in particular citric acid.

Polyacrylic acid cross-linking agents may also be selected from polyacrylic acid homopolymers, copolymers of acrylic acid, and mixtures thereof. The fibers may have between 1.0 weight % and 10.0 weight %, preferably between 3 weight % and 7 weight %, of these cross-linking agents, calculated on a dry fiber weight basis, reacted therewith in the form of intra-fiber crosslink bonds. The cross-linking agent may be a polyacrylic acid polymer having a molecular weight of from 500 to 40,000, preferably from 1,000 to 20,000. The polymeric polyacrylic acid cross-linking agent may be a copolymer of acrylic acid and maleic acid, in particular wherein the weight ratio of acrylic acid to maleic acid is from 10:1 to 1:1, preferably from 5:1 to 1.5:1. An effective amount of citric acid may be further mixed with said polymeric polyacrylic acid cross-linking agent.

The distribution layer comprising cross-linked cellulose fibers may comprise other fibers, but this layer may advantageously comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

Fastening System 42, 44

The absorbent article may include a fastening system, especially when the article is a taped diaper as exemplified in FIG. 9. The fastening system can be used to provide lateral tensions about the circumference of the absorbent article to hold the absorbent article on the wearer. Such a fastening system is not necessary for training pant articles since the waist region of these articles is already bonded and elasticized. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,86, and 5,591,152.

Front and Back Ears 46, 40

The absorbent article may comprise front ears 46 and back ears 40 as is known in the art in taped diapers. Training pants which are already sealed along the waist edges typically do not require front ears and back ears. The ears can be integral part of the chassis, for example formed from the topsheet and/or backsheet as side panel. Alternatively, as represented in FIG. 9, they may be separate elements attached by gluing and/or heat embossing. The back ears 40 are optionally stretchable to facilitate the attachment of the tabs 42 on the landing zone 44 and maintain the taped diapers in place around the wearer's waist. The front ears 46 may also be optionally elastic or extensible to provide a more comfortable and contouring fit.

Barrier Leg Cuffs 34 and Gasketing Cuffs 32

Absorbent articles such as taped diapers, training pants or adult incontinence pants may typically further comprise cuff components 30 that improve the fit of the article around the legs of the wearer, in particular the cuffs typically comprise barrier leg cuffs 34 and gasketing cuffs 32. The cuffs 30 may comprise a piece of material, typically a nonwoven, which is one side partially bonded to the article and on the other side can be partially raised away from the topsheet and thus stand up from the plane defined by the topsheet as shown for example in FIG. 10. Both part of the cuffs may be advantageously elasticized. The raised part of the cuff components is referred to herein as barrier leg cuffs 34 and can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the crotch point (C).

For example, U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

The barrier leg cuffs 34 may be delimited by a proximal edge 36 joined to the rest of the article, typically the topsheet, and a free terminal edge 38 intended to contact and form a seal with the wearer's skin. The barrier leg cuffs 34 may be joined at the proximal edge 36 with the chassis of the article by a bond 37 which may be made for example by adhesive bonding, fusion bonding or combination of known bonding means, for example as disclosed in WO2014/168810A1 (Bianchi et al.). The bond 37 at the proximal edge 36 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to its free terminal edge 38 to provide a better seal.

In addition to the barrier leg cuffs 34, the article may comprise gasketing cuffs 32, which are formed in the same plane as the chassis of the absorbent article, in particular may be at least partially enclosed between the topsheet and the backsheet, and typically placed further laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings. Typically the barrier leg cuffs 34 are disposed more internally than the gasketing cuffs 32. The barrier leg cuffs are thus also referred to as inner cuffs and the gasketing cuffs as outer cuffs.

Other Components

The absorbent articles of the invention can further comprise any other typical components known for the intended purpose of the article that are not illustrated in the Figures, such as a transverse barrier element extending across the topsheet to form a receptacle for bowel movement, a lotion application on the topsheet, a wetness indicator comprising a pH indicator disposed between the absorbent core and the backsheet, etc. These components are well-known in the art and will not be further discussed herein. Reference is made to WO2014/093310 where several examples of these components are disclosed in more details.

The absorbent article may also comprise at least one elastic waist band (also called elastic waist feature) disposed parallel to and along the back edge of the article and less commonly parallel to and along the front edge of the article. Such waistbands help providing improved fit and containment at the back and/or front edge of the article. The elastic waist feature is generally intended to elastically expand and contract to dynamically fit the wearer's waist. The elastic waist feature may be constructed in a number of different configurations. Non-limiting examples of back and front waistbands can be found in WO2012/177400 and WO2012/177401 (Lawson), and U.S. Pat. Nos. 4,515,595, 4,710,189, 5,221,274 and 6,336,922 (VanGompel et al.).

Packages

A plurality of articles according to the invention may be packaged in a package for transport and sale. At least 50% of the articles in the package may be according to the invention, and preferably substantially all the articles. The articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution and inventory savings to manufacturers owing to the size of the packages.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression may be typically sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For each of the values indicated in the previous sentence, it may be desirable to have an In-Bag Stack Height of greater than 60, or greater than 70 mm, or greater than 75 mm, or greater than 80 mm. Alternatively, packages of the absorbent articles of the present disclosure may have an In-Bag Stack Height of from 60 mm to 110 mm, from 75 mm to 110 mm, from 80 mm to 110 mm, from 80 mm to 105 mm, or from 80 mm to 100 mm, specifically reciting all 0.1 mm increments within the specified ranges and all ranges formed therein or thereby, according to the In-Back Stack Height Test described herein.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art. The individual components may be converted into an absorbent article according to any process as is known in the art.

Test Procedures

The values indicated herein are measured according to the methods indicated herein below, unless specified otherwise. All measurements are performed at 21° C.±2° C. and 50%±5% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2.R3 (12).

Dry Absorbent Core Caliper Test

This test may be used to measure the caliper of the absorbent core (before use i.e. without fluid loading) in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The core is conditioned at least 24 hours as indicated above.

Measurement procedure: The core is laid flat with the bottom side, i.e. the side intended to be placed towards the backsheet in the finished article facing down. The point of measurement (e.g. the crotch point C) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10±1 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as for the Dry Absorbent Core Caliper Test with the difference that the caliper of the finished absorbent article is measured instead of the caliper of the core. The point of measurement may be the intersection of the longitudinal axis 80' and transversal axis 90' of the absorbent article. If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the area of measurement.

Water Retention Value Measurement Procedure

The following procedure is utilized to determine the water retention value of fibers using a centrifugal method. A sample of 0.35±0.05 grams of fibers is soaked in a covered container with 100 mL distilled water at 23±2° C. for 17 hours. The soaked fibers are collected on a filter and transferred to a US standard 80-mesh wire basket supported 40 mm above a 60-mesh screened bottom of a centrifuge tube. The tube is covered with a plastic cover and the sample is centrifuged at a relative centrifuge acceleration of 1600±100 gravities (15.7±1.0 km/s$^2$) for 20 minutes. The centrifuged fibers are then removed from the basket and weighed. The weighed fibers are dried to a constant weight at 105° C. in a forced-air oven located in a controlled temperature and humidity environment at 23±2° C. and 50±5% RH. The water retention value (WRV) is calculated as follows:

$$WRV = \frac{(W-D)}{D} \times 100$$

where

W=wet weight of centrifuged fibers

D=dry weight of centrifuged fibers, and

W−D=weight of absorbed water

In-Bag Stack Height Test

The In-Bag stack height of a package of absorbent articles is determined as follows:

Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams. Such a testing apparatus is for example illustrated on FIG. 19 of US2008/0312624A1.

Test Procedure: Absorbent article packages are equilibrated at 21±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Determination of the Basis Weight of the Absorbent Material

The basis weight distribution of the absorbent material in the central and the lateral absorbent zones of the absorbent core is determined by the manufacturer based on the desired product specification. For example, if a SAP printing process as exemplified in FIGS. 12-13 is used, the SAP distribution will be determined by the distribution of the cavities 123 on the printing roll and the size of the depressions between the bars 36. If an air-laid core making process is used, for example to deposit a mix of cellulose fibers and SAP particles as absorbent material, the absorbent material distribution will be determined by the shape of the core mold on which the fibers and SAP particles are deposited. The local basis weight of the absorbent material in the different areas of the absorbent core can be thus directly determined from the manufacturer's specification for the absorbent core's manufacturing tool. For the purpose of calculating the basis weight in the different absorbent zones of the core, any absorbent material-free areas in the plane of the absorbent core such as in the channel-forming areas or any material free recesses at the longitudinal sides of the core (in a profiled core, not represented) are disregarded. The distribution of material can be displayed in a diagram as shown on FIG. 6 and FIG. 8, which clearly shows the repartition of the different transversal sections.

If the manufacturer specifications are not known for a given absorbent core, in particular if the absorbent core was made by a third party, the basis weight of the absorbent material in different sections of the different absorbent zones can be determined in the following manner. The absorbent core is carefully separated from the other components of the article (topsheet, backsheet, . . . ) so as not to damage the absorbent core or modify the distribution of the absorbent material. Then a particular area of interest of the core can be cut out using a die or another suitable means to avoid loss of material, and the area weighted. The absorbent material basis weight in the cut-out area is calculated by dividing the weight of the area (minus the weight of the core wrap) by the size of the area. The basis weight of the core wrap can be determined by taking a sample in an area of the core wrap not comprising the absorbent material and weighing this sample. This procedure can further be repeated on a sufficient amount of similar articles to obtain a good approximation of the basis weight distribution across different sections of the absorbent zones and to smooth out any small variations between individual articles due to process variability.

Misc

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core extending in a longitudinal direction parallel to a longitudinal axis and a transversal direction perpendicular to the longitudinal direction, wherein the absorbent core comprises:

a core wrap comprising a top side and a bottom side;

an absorbent material between the top side and the bottom side of the core wrap;

a first and second longitudinally-extending channel-forming areas substantially free of absorbent material, and wherein the first channel-forming area is on one side of the longitudinal axis and the second channel-forming area is on another side of the longitudinal axis;

a central absorbent zone comprising absorbent material and disposed between the first and the second channel-forming areas; and a first lateral absorbent zone and a second lateral absorbent zone comprising absorbent material and disposed laterally outwardly of the first channel-forming area and the second channel-forming area respectively;

wherein:

a basis weight of the absorbent material in the central absorbent zone is higher than a basis weight of the absorbent material in each of the lateral absorbent zones for at least a first transversal section (S1) of the core having a first length in the longitudinal direction of at least 10 mm;

the basis weight of the absorbent material in the central absorbent zone is lower than the basis weight of the absorbent material in each of the lateral absorbent zones for at least a second transversal section (S2) of the core having a second length in the longitudinal direction of at least 10 mm; and wherein at least one transversal folding line is formed in a transversal section (S4) of the core, wherein the transversal section (S4) comprises a minimum basis weight in the lateral absorbent zones relative to the neighboring regions of the lateral absorbent zones, so that the transversal section (S4) of minimum basis weight acts as a folding line, wherein the transversal section (S4) is oriented parallel to the transversal direction, wherein the transversal section (S4) comprises a longitudinal length of 5 mm to 30 mm, and wherein the transversal section (S4) extends laterally up to longitudinal side edges of the absorbent core.

2. The absorbent core of claim 1, wherein the at least one transversal folding line is disposed in a crotch region of the absorbent core.

3. The absorbent core of claim 1, wherein the basis weight of the absorbent material in the central absorbent zone is about equal to the basis weight of the absorbent material in the lateral absorbent zones along a third transversal sections (S3) of the core having a length of at least 10 mm in the longitudinal direction.

4. The absorbent core of claim 1, wherein:

the basis weight difference between a maximum basis weight value in the central absorbent zone and a minimum basis weight value in any of the lateral absorbent zones in the first transversal section (S1) is of at least 20 $g/m^2$; and the basis weight difference between a maximum basis weight value in any of the lateral absorbent zones and a minimum basis weight value in the central absorbent zone in the second transversal section (S2) is of at least 10 $g/m^2$.

5. The absorbent core of claim 4, wherein the basis weight difference between the maximum basis weight value in the central absorbent zone and the minimum basis weight value in any of the lateral absorbent zones in the first transversal section (S1) is of at least 50 $g/m^2$.

6. The absorbent core of claim 4, wherein the basis weight difference between the maximum basis weight value in any of the lateral absorbent zones and the minimum basis weight value in the central absorbent zone in the second transversal section (S2) is of at least 30 $g/m^2$.

7. The absorbent core of claim 1, wherein the first and second channel-forming areas are at least partially curved or angled so that the width of the central absorbent zone varies along at least a portion of the length of the core.

8. The absorbent core of claim 1, wherein the top side of the core wrap is attached to the bottom side of the core wrap in the channel-forming areas by at least one selected from ultrasonic bonding, fusion bonding, and adhesive bonding.

9. An absorbent core extending in a longitudinal direction parallel to a longitudinal axis and a transversal direction perpendicular to the longitudinal axis, the absorbent core comprising:

a. a first substrate;

b. a second substrate;

c. absorbent material disposed between the first substrate and the second substrate to define an absorbent material deposition area, the absorbent material comprising a mix of particulate superabsorbent polymer and cellulose fibers;

d. first and second channel-forming areas disposed within the absorbent material deposition area; and e. a central absorbent zone disposed between the first and second channel-forming areas, a first lateral absorbent zone disposed transversally outwardly from the first channel-forming area, a second lateral absorbent zone disposed transversally outwardly from the second channel-forming area, an optional front absorbent zone disposed longitudinally outwardly from the first and second channel-forming areas to a first end of the absorbent core, and an optional back absorbent zone disposed longitudinally outwardly from the first and second channel-forming areas to an opposing second end of the absorbent core;

f. wherein a weight percentage of absorbent material within the central absorbent zone is from 15-55;

g. wherein a weight percentage of absorbent material within each of the first lateral absorbent zone and the second lateral absorbent zone is 10-40;

h. wherein a weight percentage of absorbent material within each of the optional front absorbent zone and the optional back absorbent zone is 0-25, and i. wherein at least one transversal folding line is formed in a transversal section (S4) of the core, wherein the transversal section (S4) comprises a minimum basis weight in the lateral absorbent zones relative to the neighboring regions of the lateral absorbent zones, so that the transversal section (S4) of minimum basis weight is configured to be a folding line to allow increased flexibility of the absorbent core in the longitudinal direction, wherein the transversal section (S4) comprises a longitudinal length of 5 mm to 30 mm, and wherein the transversal section (S4) is oriented parallel to the transversal direction and extends laterally up to longitudinal side edges of the absorbent core.

10. The absorbent core of claim 9, wherein the first substrate is bonded to the second substrate within the first and second channel-forming areas.

11. The absorbent core of claim 10, wherein the wherein the first substrate is adhesively bonded to the second substrate within the first and second channel-forming areas.

12. The absorbent core of claim 10, wherein the wherein the first substrate is ultrasonically bonded to the second substrate within the first and second channel-forming areas.

13. The absorbent core of claim 10, wherein the wherein the first substrate is heat bonded to the second substrate within the first and second channel-forming areas.

14. The absorbent core of claim 9, wherein the first substrate is at least partially wrapped around the second substrate.

* * * * *